(12) United States Patent
Liu

(10) Patent No.: US 7,626,068 B2
(45) Date of Patent: Dec. 1, 2009

(54) NI CATALYSTS AND METHODS FOR ALKANE DEHYDROGENATION

(75) Inventor: Yumin Liu, Santa Clara, CA (US)

(73) Assignee: Celanese International Corporation, Dallas, TX (US)

(*) Notice: Subject to any disclaimer, the term of this patent is extended or adjusted under 35 U.S.C. 154(b) by 159 days.

(21) Appl. No.: 11/786,489

(22) Filed: Apr. 11, 2007

(65) Prior Publication Data
US 2007/0191665 A1 Aug. 16, 2007

Related U.S. Application Data

(60) Division of application No. 10/719,441, filed on Nov. 20, 2003, now Pat. No. 7,227,049, which is a continuation of application No. 09/849,378, filed on May 4, 2001, now Pat. No. 6,777,371, which is a division of application No. 09/510,458, filed on Feb. 22, 2000, now Pat. No. 6,417,422, which is a continuation-in-part of application No. 09/255,371, filed on Feb. 22, 1999, now Pat. No. 6,355,854, and a continuation-in-part of application No. 09/255,384, filed on Feb. 22, 1999, now Pat. No. 6,436,871.

(51) Int. Cl.
C07C 5/327 (2006.01)

(52) U.S. Cl. ............ 585/654; 585/658; 585/616; 585/629; 585/631

(58) Field of Classification Search ............ 585/654, 585/658, 616, 629, 631
See application file for complete search history.

(56) References Cited

U.S. PATENT DOCUMENTS

| | | | |
|---|---|---|---|
| 3,502,737 A | 3/1970 | Ghublikian | |
| 3,670,044 A | 6/1972 | Drehman et al. | |
| 3,678,124 A | 7/1972 | Stepanov et al. | |
| 3,764,632 A * | 10/1973 | Takenaka et al. | 585/622 |
| 3,832,205 A | 8/1974 | Lowery | |
| 3,862,256 A | 1/1975 | Isailingold et al. | |
| 3,901,828 A | 8/1975 | Mai et al. | |
| 3,907,834 A | 9/1975 | Milberger et al. | |
| 3,929,670 A | 12/1975 | Kudo et al. | |
| 4,003,978 A | 1/1977 | Shiraishi et al. | |
| 4,059,664 A | 11/1977 | Nicolas et al. | |
| 4,070,413 A | 1/1978 | Imai | |
| 4,115,441 A | 9/1978 | Shaw et al. | |
| 4,176,140 A | 11/1979 | Bertus et al. | |
| 4,180,690 A | 12/1979 | Imai | |
| 4,246,421 A * | 1/1981 | Bartek et al. | 546/352 |
| 4,250,346 A | 2/1981 | Young et al. | |
| 4,251,394 A | 2/1981 | Carter et al. | |
| 4,283,307 A | 8/1981 | Barone et al. | |
| 4,296,607 A | 10/1981 | Lawless | |
| 4,374,758 A | 2/1983 | Sasaki et al. | |
| 4,408,067 A | 10/1983 | Nakamura et al. | |
| 4,418,007 A | 11/1983 | Derrien | |
| 4,435,607 A | 3/1984 | Imai | |
| 4,524,236 A | 6/1985 | McCain | |
| 4,565,898 A | 1/1986 | O'Hara et al. | |
| 4,568,790 A | 2/1986 | McCain | |
| 4,613,715 A | 9/1986 | Haskell | |
| 4,657,653 A | 4/1987 | Bouet | |
| 4,672,146 A | 6/1987 | Abrevaya et al. | |
| 4,709,071 A | 11/1987 | Sasaki et al. | |
| 4,717,694 A | 1/1988 | Tamura et al. | |
| 4,769,357 A | 9/1988 | Sarumar et al. | |
| 4,788,371 A | 11/1988 | Imai et al. | |
| 4,940,826 A | 7/1990 | Font Freide et al. | |
| 4,996,387 A | 2/1991 | Gerhold et al. | |
| 5,043,461 A | 8/1991 | Ramachandran et al. | |
| 5,053,084 A | 10/1991 | Masumoto et al. | |
| 5,053,577 A | 10/1991 | Teller et al. | |
| 5,086,032 A | 2/1992 | Mazzocchia et al. | |
| 5,094,990 A | 3/1992 | Sasaki et al. | |
| 5,132,269 A | 7/1992 | Sasaki et al. | |
| 5,136,104 A | 8/1992 | Saito et al. | |
| 5,162,578 A | 11/1992 | McCain, Jr. et al. | |
| 5,210,293 A * | 5/1993 | Kitson | 562/512.2 |

(Continued)

FOREIGN PATENT DOCUMENTS

| | | |
|---|---|---|
| EP | 544 372 A1 | 6/1993 |
| EP | 573 713 A1 | 12/1993 |
| EP | 661 254 A2 | 7/1995 |
| WO | WO 96/33149 | 10/1996 |
| WO | WO 99/42404 | 8/1999 |
| WO | WO 99/64160 | 12/1999 |

OTHER PUBLICATIONS

Baiker, Alfons, "Recent Developments in Heterogeneous Catalytic Oxidation for Fine Chemicals Synthesis," 5th International Symposium on Heterogeneous Catalysis and Fine Chemicals, Lyon, France, Aug. 30-Sep. 3, 1999, PLl1.

(Continued)

*Primary Examiner*—Tam M Nguyen
(74) *Attorney, Agent, or Firm*—Michael W. Ferrell

(57) ABSTRACT

Catalysts and methods for alkane oxydehydrogenation are disclosed. The catalysts of the invention generally comprise (i) nickel or a nickel-containing compound and (ii) at least one or more of titanium (Ti), tantalum (Ta), niobium (Nb), hafnium (Hf), tungsten (W), yttrium (Y), zinc (Zn), zirconium (Zr), or aluminum (Al), or a compound containing one or more of such element(s). In preferred embodiments, the catalyst is a supported catalyst, the alkane is selected from the group consisting of ethane, propane, isobutane, n-butane and ethyl chloride, molecular oxygen is co-fed with the alkane to a reaction zone maintained at a temperature ranging from about 250° C. to about 350° C., and the ethane is oxidatively dehydrogenated to form the corresponding alkene with an alkane conversion of at least about 10% and an alkene selectivity of at least about 70%.

2 Claims, 3 Drawing Sheets

U.S. PATENT DOCUMENTS

| | | | |
|---|---|---|---|
| 5,219,816 | A | 6/1993 | Zhou et al. |
| 5,376,613 | A | 12/1994 | Dellinger et al. |
| 5,380,692 | A | 1/1995 | Nakatsuji et al. |
| 5,393,622 | A | 2/1995 | Nitta et al. |
| 5,414,209 | A | 5/1995 | Morita |
| 5,430,209 | A | 7/1995 | Agaskar et al. |
| 5,439,859 | A | 8/1995 | Durante et al. |
| 5,447,705 | A | 9/1995 | Petit et al. |
| 5,563,314 | A | 10/1996 | Agaskar et al. |
| 5,593,935 | A | 1/1997 | Golunski et al. |
| 5,639,929 | A | 6/1997 | Bharadwaj et al. |
| 5,723,707 | A | 3/1998 | Heyse et al. |
| 5,733,518 | A | 3/1998 | Durante et al. |
| 5,759,946 | A | 6/1998 | Hoang et al. |
| 5,780,700 | A | 7/1998 | Hagenmeyer et al. |
| 6,156,695 | A | 12/2000 | Soled et al. |
| 6,156,928 | A * | 12/2000 | Karim et al. ............... 562/548 |
| 6,235,678 | B1 | 5/2001 | Mamedov et al. |
| 6,239,325 | B1 | 5/2001 | Kishimoto et al. |
| 6,350,716 | B1 * | 2/2002 | Cook et al. ............... 502/300 |
| 6,355,854 | B1 | 3/2002 | Liu |
| 6,417,422 | B1 | 7/2002 | Liu |
| 6,436,871 | B1 | 8/2002 | Liu |
| 6,548,697 | B1 | 4/2003 | Ellis et al. |
| 6,566,573 | B1 | 5/2003 | Bharadwaj et al. |
| 6,677,497 | B2 | 1/2004 | Liu |
| 6,777,371 | B2 | 8/2004 | Liu |
| 6,891,075 | B2 | 5/2005 | Liu |
| 7,227,049 | B2 | 6/2007 | Liu |
| 2005/0085678 | A1 * | 4/2005 | Lopez Nieto et al. ....... 585/658 |
| 2006/0025628 | A1 * | 2/2006 | Zerella et al. ............... 562/542 |
| 2006/0281942 | A1 * | 12/2006 | Ferguson et al. ......... 560/241.1 |
| 2007/0197378 | A1 | 8/2007 | Liu |
| 2007/0197847 | A1 | 8/2007 | Liu |

OTHER PUBLICATIONS

Dalmon, et al., "Hydrogenolysis of $C_2H_6$, $C_3H_8$, and $n$-$C_4H_{10}$ over Silica-Supported Nickel-Copper Catalysts," Journal of Catalysis, 66, 214-221, (1980).

Ducarme, et al., "Low Temperature Oxidative Dehydrogenation of Ethane over Ni-based Catalysts", 23 *Catalysis* Letters 97-101 (1994).

Ducarme, V., et al., "Low Temperature Oxidative Dehydrogenation of Ethane Over New Catalysts Based on Group VIII Metals," Symposium on Heterogeneous Hydrocarbon Oxidation Presented before the Division of Petroleum Chemistry, Inc., 211th National Meeting, American Chemical Society, New Orleans, LA, Mar. 24-29, 1996, pp. 153-156.

Ji, Lang., et al., "Effect of Group VIII Elements on the Behavior of Li/CaO Catalyst in the Oxidative Dehydrogenation of Ethane," React. Kinet. Catal. Lett., vol. 62, No. 1, 121-128 (1997).

Juarez, Lopez R. et al., "Oxidative Dehydrogenation of Ethane on Supported Vanadium-Containing Oxides," 124 Applied Catalysis A: General 281-96 (1995).

Lin, Manhua, et al., "Reaction Intermediates in the Selective Oxidation of Propane Over a Mixed Metal Oxide Catalyst," Proceedings ISO'99, Rimini (Italy), Sep. 10-11, 1999, G. Centi and S. Perahoner Ed., SCi Pub. 1999, pp. 143-144.

Liu, Yumin, et al., "High-Throughput Synthesis and Screening of Mixed Metal Oxides for Ethane Oxidative Dehydrogenation to Ethylene," 4th European Congress on Catalysis, Rimini, Italy, Sep. 5-10, 1999, Book of Abstracts, p. 41.

Liu, Yumin, et al., "High-Throughput Synthesis and Screening of V-Al-Nb and Cr-Al-Nb Oxide Libraries for Ethane Oxidative Dehydrogenation to Ethylene," Proceedings ISO'99, Rimini (Italy), Sep. 10-11, 1999, G. Centi and S. Perahoner. Ed., SCi Pub. 1999, pp. 117-118.

Nazimek, D., "Influence of Added Copper on the Activity of $Ni/Al_2O_3$ Catalysts in the Hydrogenolysis of n-Butane," React. Kinet. Catal. Lett., vol. 13, No. 4, 331-337 (1980).

Popova, et al., "Characterization of Nickel Loaded Mordenite Catalysts by Temperature Programmed Reduction," React. Kinet. Catal. Lett., vol. 39, No. 1,27-32 (1989).

Richardson, J.T., et al., "Characterization and Deactivation of $NiO$-$ThO_2$ Catalysts," Applied Catalysis, 48, (1989) 159-176.

Schuurman, Y. et al., "Low Temperature Oxidative Dehydrogenation of Ethane over Catalyst Based on Group VIII Metals," 163 Applied Catalysis A: General 227-35 (1997).

Sinfelt, et al., "Catalytic Hydrogenolysis and Dehydration Over Copper-Nickel Alloys," Journal of Catalysis, 24, 283-296 (1972).

Thorsteinson, E. M. et al., "The Oxidative Dehydrogenation of Ethane over Catalyst Containing Mixed Oxide of Molybdenum and Vanadium," 52 J. Catalysis 116-32 (1978).

Zhang, Mingqian, et al., "Calcium-Nickel-Lithium Oxide: a High Selectivity Catalyst for the Oxidative Dehydrogenation of Ethane to Ethylene," J. Chem. Soc., Chem. Commun., 1993, pp. 1480-1481.

Notice of Allowance dated Oct. 9, 2008 in U.S. Appl. No. 11/786,799.

Office Action dated Mar. 27, 2008 in U.S. Appl. No. 11/786,799, filed Apr. 11, 2007 and published as US 2007-0197378 A1.

* cited by examiner

Figure 2A: Ethane conversion and ethylene selectivity over 400 hours for $Ni_{0.75}Ta_{0.28}Sn_{0.03}O_x$ over at 275°C Figure 2B: Ethane conversion and ethylene selectivity over 400 hours for $Ni_{0.71}Nb_{0.27}Co_{0.02}O_x$ over at 275°C

NI CATALYSTS AND METHODS FOR ALKANE DEHYDROGENATION

BACKGROUND OF INVENTION

The present invention generally relates to catalysts and methods for alkane or alkene dehydrogenation and specifically, to Ni-containing catalysts and methods for oxidative dehydrogenation of alkanes or alkenes. The invention particularly relates, in preferred embodiments, to Ni oxide/mixed-metal oxide catalysts and methods for oxidative dehydrogenation of alkanes or alkenes, and especially of $C_2$ to $C_4$ alkanes, and particularly, for oxidative dehydrogenation of ethane to ethylene.

Ethylene can be produced by thermal cracking of hydrocarbons, by non-oxidative dehydrogenation of ethane, or by oxidative dehydrogenation of ethane (ODHE). The latter process is attractive for many reasons. For example, compared to thermal cracking, high ethane conversion can be achieved at relatively low temperatures (about 400° C. or below). Unlike thermal cracking, catalytic ODHE is exothermic, requiring no additional heat to sustain the reaction. In contrast to catalytic non-oxidative dehydrogenation, catalyst deactivation by coke formation is relatively minimal in ODHE because of the presence of oxidant (e.g., molecular oxygen) in the reactor feed. Other alkanes can be similarly oxidatively dehydrogenated to the corresponding alkene.

Thorsteinson and coworkers have disclosed useful low-temperature ODHE catalysts comprising mixed oxides of molybdenum, vanadium, and a third transition metal. E. M. Thorsteinson et al., "The Oxidative Dehydrogenation of Ethane over Catalyst Containing Mixed Oxide of Molybdenum and Vanadium," 52 *J. Catalysis* 116-32 (1978). More recent studies examined families of alumina-supported vanadium-containing oxide catalysts, MV and MVSb, where M is Ni, Co, Bi, and Sn. R. Juarez Lopez et al., "Oxidative Dehydrogenation of Ethane on Supported Vanadium-Containing Oxides," 124 *Applied Catalysis A: General* 281-96 (1995). Baharadwa; et al. disclose oxidative dehydrogenation of ethane and other alkanes using a catalysts of Pt, Rh, Ni or Pt/Au supported on alumina or zirconia. See PCT Patent Application WO 96/33149. U.S. Pat. No. 5,439,859 to Durante et al. discloses the use of reduced, sulfided nickel crystallites on siliceous supports for dehydrogenation and successive oxidation of alkanes. Schuurman and coworkers describe unsupported iron, cobalt and nickel oxide catalysts that are active in ODHE. Y. Schuurman et al., "Low Temperature Oxidative Dehydrogenation of Ethane over Catalysts Based on Group VIII Metals," 163 *Applied Catalysis A: General* 227-35 (1997). Other investigators have also considered the use of nickel or nickel oxide as catalysts or catalyst components for oxidative dehydrogenation. See, for example, Ducarme et al., "Low Temperature Oxidative Dehydrogenation of Ethane over Ni-based Catalysts", 23 *Catalysis Letters* 97-101 (1994); U.S. Pat. No. 3,670,044 to Drehman et al.; U.S. Pat. No. 4,613,715 to Haskell; U.S. Pat. No. 5,723,707 to Heyse et al.; U.S. Pat. No. 5,376,613 to Dellinger et al.; U.S. Pat. No. 4,070,413 to Imai et al.; U.S. Pat. No. 4,250,346 to Young et al.; and U.S. Pat. No. 5,162,578 to McCain et al.

Although nickel-containing catalysts are known in the art for alkane dehydrogenation reactions, none of the known nickel-containing catalysts have been particularly attractive for commercial applications—primarily due to relatively low conversion and/or selectivity. Hence, a need exists for new, industrially suitable catalysts and methods having improved performance characteristics (e.g., conversion and selectivity) for the oxidative dehydrogenation of alkanes.

SUMMARY OF INVENTION

It is therefore an object of the present invention to provide for new, industrially suitable catalysts for oxidative dehydrogenation of alkanes to the corresponding alkenes.

Briefly, therefore, the invention is directed to methods for preparing an alkene, and preferably a $C_2$ to $C_4$ alkene, such as ethylene, from the corresponding alkane, such as ethane. In general, the method comprises providing the alkane (or substituted alkane), and preferably the $C_2$ to $C_4$ alkane (or substituted $C_2$ to $C_4$ alkane) and an oxidant to a reaction zone containing a catalyst, and dehydrogenating the alkane to form the corresponding alkene. The oxidant is preferably a gaseous oxidant such as molecular oxygen, and is preferably provided, for example, as oxygen gas, air, diluted air or enriched air. The alkane is preferably oxidatively dehydrogenated. The reaction temperature is preferably controlled, during the dehydrogenation reaction, to be less than about 325° C., and preferably less than about 300° C.

The catalyst comprises, in one embodiment, (i) a major component consisting essentially of Ni, a Ni oxide, a Ni salt, or mixtures thereof, and (ii) one or more minor components consisting essentially of an element or compound selected from the group consisting of Ti, Ta, Nb, Co, Hf, W, Y, Zn, Zr, Al, oxides thereof and salts thereof, or mixtures of such elements or compounds. The catalyst preferably comprises Ni oxide and one or more of Ti oxide, Nb oxide, Ta oxide, Co oxide or Zr oxide.

In another embodiment, the catalyst comprises a compound having the formula I,

$$Ni_xA_aB_bC_cO_d \qquad (I),$$

where

A is an element selected from the group consisting of Ti, Ta, Nb, Hf, W, Y, Zn, Zr, Al, and mixtures of two or more thereof, B is an element selected from the group consisting of a lanthanide element, a group IIIA element, a group VA element, a group VIA element, a group IIIB element, a group IVB element, a group VB element, a group VIB element, and mixtures of two or more thereof, C is an alkali metal, an alkaline earth metal or mixtures thereof, x is a number ranging from about 0.1 to about 0.96, a is a number ranging from about 0.04 to about 0.8, b is a number ranging from 0 to about 0.5, c is a number ranging from 0 to about 0.5, and d is a number that satisfies valence requirements.

In a further embodiment, the catalyst comprises a compound having the formula (II)

$$Ni_xTi_jTa_kNb_lLa^*{}_mSb_nSn_sBi_tCa_uK_vMg_wO_d \qquad (II),$$

where

La* is one or more lanthanide series elements selected from the group consisting of $La_m$, $Ce_n$, $Pr_o$, $Nd_p$, $Sm_q$, x is a number ranging from about 0.1 to about 0.96, j, k and l are each numbers ranging from 0 to about 0.8 and the sum of (j+k+l) is at least about 0.04, m, n, o, p, q, r, s and t are each numbers ranging from 0 to about 0.1, and the sum of (m+n+o+p+q+r+s+t) is at least about 0.005, u, v and w are each numbers ranging from 0 to about 0.1, and d is a number that satisfies valence requirements.

In still another embodiment, the catalyst comprises (i) a Ni oxide, and (ii) an oxide of an element selected from the group consisting of Ti, Ta, Nb, Co, Hf, W, Y, Zn, Zr, and Al, and the alkane is dehydrogenated to form the corresponding alkene with an alkane conversion of at least about 10% and an alkene selectivity of at least about 70%. Ethane conversion is preferably at least about 15% and more preferably at least about 20%. Ethylene selectivity is, in combination with any of the preferred conversion values, preferably at least about 80%, and more preferably at least about 90%.

In one embodiment, the catalyst is a calcination product of a catalyst precursor composition comprising (i) Ni, a Ni oxide, a Ni salt or mixtures thereof, and (ii) an element or compound selected from the group consisting of Ti, Ta, Nb, Co, Hf, W, Y, Zn, Zr, Al, oxides thereof and salts thereof, or mixtures of such elements or compounds.

In yet another embodiment, the alkane is co-fed to a reaction zone with the corresponding alkene, such that the alkane is dehydrogenated to form the alkene in a reaction zone comprising the corresponding alkene in a molar concentration of at least about 5%, relative to total moles of hydrocarbon. The alkane conversion in such embodiment is preferably at least about 5%, and the alkene selectivity is preferably at least about 50%. In a preferred approach, the alkane dehydrogenation is effected in a multi-stage reactor, such that the alkane (or substituted $C_2$ to $C_4$ alkane) and gaseous oxidant are fed to a first reaction zone containing the catalyst, the alkane is dehydrogenated therein to form the corresponding alkene, the product stream comprising the corresponding alkene and unreacted alkane are exhausted from the first reaction zone and then fed to a second reaction zone, together with additional, supplemental gaseous oxidant, and the alkane is dehydrogenated to form the corresponding alkene in the second reaction zone.

The invention also directed to nickel-containing mixed-metal oxide compositions and catalysts, as characterized above, and to methods for preparing the same.

Such catalysts and methods have advantageous performance characteristics for oxidative dehydrogenation of alkanes to their corresponding alkene, and particularly for dehydrogenation of unsubstituted or substituted $C_2$ to $C_4$ alkanes to the corresponding alkene(s). The conversion, selectivity, space velocity, catalyst stability and reaction temperature for oxydehydrogenation of ethane to ethylene are particularly attractive.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

DETAILED DESCRIPTION OF THE INVENTION

Figure 1A:
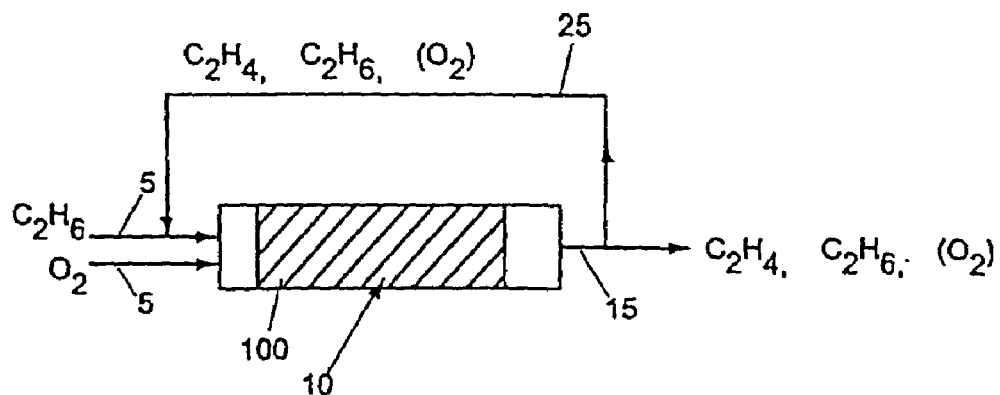
FIG. 1A and FIG. 1B are schematic representations of exemplary reaction system configurations, specifically involving product stream recycle (FIG. 1A) and multi-stage reaction zones (FIG. 1B).

According to the present invention, an alkane or alkene is oxidatively dehydrogenated over a nickel catalyst to form one or more corresponding alkene(s) or dialkene, respectively, and water. The oxidative dehydrogenation reaction can be represented (for alkane reactants) as:

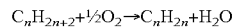

$$C_nH_{2n+2} + \tfrac{1}{2}O_2 \rightarrow C_nH_{2n} + H_2O$$

The catalysts of the invention generally comprise (i) nickel or a nickel-containing compound and (ii) at least one or more of titanium (Ti), tantalum (Ta), niobium (Nb), cobalt (Co), hafnium (Hf), tungsten (W), yttrium (Y), zinc (Zn), zirconium (Zr), or aluminum (Al), or a compound containing one or more of such element(s).

In one embodiment of the invention, the nickel catalyst comprises (i) Ni, a Ni oxide, a Ni salt, or mixtures thereof as a major component, and (ii) an element or compound selected from the group consisting of Ti, Ta, Nb, Co, Hf, W, Y, Zn, Zr, Al, oxides thereof and salts thereof, or mixtures of such elements or compounds as one or more minor components. As used herein, the "major component" is the component of the catalytically active compound or composition having the highest concentration on an atomic basis. "Minor components" are components of the catalytically active compound or composition that do not have the highest concentration on an atomic basis. In general, one of the aforementioned metal components may present as in elemental form, as an oxide, and/or as a salt depending on the nature and extent of calcination.

The major component of the catalyst preferably consists essentially of a Ni oxide. The major component of the catalyst can, however, also include various amounts of elemental Ni and/or Ni-containing compounds, such as Ni salts. The Ni oxide is an oxide of nickel where nickel is in an oxidation state other than the fully-reduced, elemental Ni° state, including oxides of nickel where nickel has an oxidation state of $Ni^{+2}$, $Ni^{+3}$, or a partially reduced oxidation state. The Ni salts can include any stable salt of nickel, including, for example, nitrates, carbonates and acetates, among others. The amount of nickel oxide (NiO) present in the major component is at least about 10%, preferably at least about 20%, more preferably at least about 35%, more preferably yet at least about 50% and most preferable at least about 60%, in each case by moles relative to total moles of the major component. Without being bound by theory not specifically recited in the claims, the Ni and/or Ni oxide acts as a redox-active metal center for the oxydehydrogenation reaction.

The one or more minor component(s) of the catalyst preferably consist essentially of an element or compound selected from the group consisting of Ti, Ta, Nb, Co, Hf, W, Y, Zn, Zr, Al, oxides thereof and salts thereof, or mixtures of such elements or compounds. The minor component(s) more preferably consist essentially of one or more of the following groupings of elements, oxides thereof, salts thereof, or mixtures of the same: (i) Ti, Ta, Nb, Hf, W, Y, Zn, Zr, Al, (ii) Ti, Ta, Nb, Hf, W and Y; (iii) Ti, Ta, Nb, Hf and W; (iv) Ti, Ta, Nb, Co and Zr (v) Ti, Ta, Nb and Co, (vi) Ti, Ta, Nb and Zr, and (vii) Ti, Ta and Nb. The minor component can likewise consist essentially of each of the aforementioned minor-component elements (Ti, Ta, Nb, Co Hf, W, Y, Zn, Zr or Al) individually, oxides thereof, salts thereof, or mixtures of the same. With respect to each of the aforementioned groupings of elements or individual elements, the minor component(s) preferably consist essentially of oxides of one or more of the minor-component elements, but can, however, also include various amounts of such elements and/or other compounds (e.g., salts) containing such elements. An oxide of such minor-component elements is an oxide thereof where the respective element is in an oxidation state other than the fully-reduced state, and includes oxides having an oxidation states corresponding to known stable valence numbers, as well as to oxides in partially reduced oxidation states. Salts of such minor-component elements can be any stable salt thereof, including, for example, nitrates, carbonates and acetates, among others. The amount of the oxide form of the particular recited elements present in one or more of the minor component(s) is at least about 5%, preferably at least about 10%, preferably still at least about 20%, more preferably at least about 35%, more preferably yet at least about 50% and most preferable at least about 60%, in each case by moles relative to total moles of the particular minor component. Without being bound by theory not specifically recited in the claims, the one or more first minor components provide a matrix environment for the Ni/Ni oxide active metal center and help maintain the active metal center well dispersed. Although the first minor components can themselves be redox inactive under reaction conditions, particularly to oxygen and hydrocarbons, they are nonetheless considered to be a component of the catalytically active compound or composition. As noted below, the first minor component can also have a support or carrier functionality.

In another, preferred embodiment, the nickel catalyst can comprise (i) a major component consisting essentially of Ni oxide; and (ii) a minor component consisting essentially of one or more of the following oxides, considered individually or collectively in the various permutations: Ti oxide, Ta oxide, and/or Nb oxide, optionally together with one or more of Hf oxide, W oxide, and/or Y oxide, optionally together with one or more of Zn oxide, Zr oxide and/or Al oxide.

In addition to the aforementioned minor component(s) of the catalyst (generally referred to hereinafter as "first minor components"), the catalyst can additionally comprise one or more second minor components. The second minor component(s) can consist essentially of an element or compound selected from the group consisting of a lanthanide element, a group IIIA element, a group VA element, a group VIA element, a group IIIB element, a group IVB element, a group VB element, a group VIB element, oxides thereof and salts thereof, or mixtures of such elements or compounds. The second minor component preferably consists essentially of an element or compound selected from the group consisting of La, Ce, Pr, Nd, Sm, Sb, Sn, Bi, Pb, Tl, In, Te, Cr, V, Mn, Mo, Fe, Co, Cu, Ru, Rh, Pd, Pt, Ag, Cd, Os, Re, Ir, Au, Hg, oxides thereof and salts thereof, or mixtures of such elements or compounds. More preferably, the second minor component consists essentially of an element or compound selected from the group consisting of La, Ce, Pr, Nd, Sm, Sb, Sn, Bi, Co, Ag, Cr, oxides thereof and salts thereof, or mixtures of such elements or compounds. If Co is considered within the group of first minor components, it can be excluded from the aforementioned groups of second minor components. The second minor component is preferably an oxide of one of the aforementioned second-minor-component elements. The oxides and salts can be as described above in connection with the first-minor components. Without being bound by theory not specifically recited in the claims, the second minor component can be redox active components with respect to enhancing the redox potential of the Ni/Ni oxide active metal centers.

The catalyst can also include, as yet a further (third) minor component(s), one or more of an element or compound selected from the group consisting of the alkali metals, the alkaline earth metals, oxides thereof, and salts thereof, or mixtures of such elements or compounds. Preferably, the third minor component consists essentially of an element or compound selected from the group consisting of Ca, K, Mg, Sr, Ba, Li and Na, most preferably Ca, K and Mg, and in either case, oxides thereof and salts thereof, or mixtures of such elements or compounds. The third minor component is preferably an oxide of one of the aforementioned third-minor-component elements. The oxides and salts can be as described above in connection with the first-minor components. Without being bound by theory not specifically recited in the claims, the third minor components are preferably basic metal oxides, and as such, can be employed to optimize the acidity or basicity, in particular with respect to selectivity.

The catalyst can include other components as well, and can be part of a composition that includes other components or agents (e.g., diluents, binders and/or fillers, as discussed below) as desired in connection with the reaction system of interest.

In a further embodiment, the nickel catalyst of the invention can be a material comprising a mixed-metal oxide compound having the formula (I):

$$Ni_xA_aB_bC_cO_d \quad (I),$$

where, A, B, C, x, a, b, c and d are described below, and can be grouped in any of the various combinations and permutations of preferences, some of which are specifically set forth herein.

In formula I, "x" represents a number ranging from about 0.1 to about 0.96. The number x preferably ranges from about 0.3 to about 0.85, more preferably from about 0.5 to about 0.9, and even more preferably from about 0.6 to about 0.8.

In formula I, "A" represents an element selected from the group consisting of Ti, Ta, Nb, Hf, W, Y, Zn, Zr and Al, or mixtures of two or more thereof. A is preferably Ti, Ta, Nb, Hf, W or Y, even more preferably Ti, Ta, Nb, Hf or W, and still more preferably Ti, Ta or Nb, or, in each case, mixtures thereof. The letter "a" represents a number ranging from about 0.04 to about 0.9, preferably from about 0.04 to about 0.8, more preferably from about 0.04 to about 0.5, even more preferably from about 0.1 to about 0.5, still more preferably from about 0.15 to about 0.5 and most preferably from about 0.3 to about 0.4.

In formula I, "B" represents an element selected from the group consisting of a lanthanide element, a group IIIA element, a group VA element, a group VIA element, a group VIIA element, a group VIIIA element, a group IB element, a group IIB element, a group IIIB element, a group IVB element, a group VB element, a group VIB element, and mixtures of two or more thereof. As used herein, periodic table subgroup designations are those recommended by the International Union of Pure and Applied Chemistry (IUPAC), such as shown on the Periodic Table of the Elements, Learning Laboratories, Inc. (1996). B is preferably an element selected from the group consisting of La, Ce, Pr, Nd, Sm, Sb, Sn, Bi, Pb, Tl, In, Te, Cr, V, Mn, Mo, Fe, Co, Cu, Ru, Rh, Pd, Pt, Ag, Cd, Os, Re, Ir, Au, and Hg. B is more preferably an element selected from the group consisting of La, Ce, Pr, Nd, Sm, Sb, Sn, Bi, Co, Cr and Ag. The letter "b" represents a number ranging from 0 to about 0.5, more preferably from 0 to about 0.4, even more preferably from 0 to about 0.2, still more preferably from 0 to about 0.1, and most preferably from 0 to about 0.05.

In formula I, C is an alkali metal, an alkaline earth metal or mixtures thereof. C is preferably an element selected from the group consisting of Ca, K, Mg, Li, Na, Sr, Ba, Cs and Rb, and is more preferably an element selected from the group consisting of Ca, K and Mg. The letter "c" represents a number ranging from 0 to about 0.5, more preferably from 0 to about 0.4, even more preferably from 0 to about 0.1, and most preferably from 0 to about 0.05.

In formula I, "O" represents oxygen, and "d" represents a number that satisfies valence requirements. In general, "d" is based on the oxidation states and the relative atomic fractions of the various metal atoms of the compound of formula I (e.g., calculated as one-half of the sum of the products of oxidation state and atomic fraction for each of the metal oxide components).

In one preferred mixed-metal oxide embodiment, where, with reference to formula I, "b" and "c" are each zero, the catalyst material can comprise a compound having the formula I-A:

$$Ni_xA_aO_d \quad \text{(I-A)},$$

where Ni is nickel, O is oxygen, and where "x", "A", "a" and "d" are as defined above.

In another preferred mixed-metal oxide embodiment, with reference to formula I, the sum of (a+b+c) is preferably less than or not more than about 0.9, is preferably not more than about 0.7, and is even more preferably not more than about 0.5, and moreover, this sum preferably ranges from about 0.04 to about 0.6, more preferably from about 0.1 to about 0.5 and most preferably from about 0.1 to about 0.4.

In still another preferred mixed-metal oxide embodiment, with reference to formula I, the sum of (a+b+c) is preferably less than or not more than about 0.5, is preferably not more than about 0.4, and is even more preferably not more than about 0.3, and moreover, this sum preferably ranges from about 0.04 to about 0.5, more preferably from about 0.1 to about 0.4 and most preferably from about 0.1 to about 0.3.

In an additional preferred mixed-metal oxide embodiment, with reference to formula I: A is Ti, Ta, Nb or Zr, or preferably, Ti, Ta or Nb; B is La, Ce, Pr, Nd, Sm, Sb, Sn, Bi, Cr, Co or Ag, or preferably, La, Ce, Pr, Nd, Sm, Sb, Sn or Bi; and C is Ca, K or Mg. In this embodiment, x ranges from about 0.1 to about 0.96, and preferably from about 0.5 to about 0.96, a ranges from about 0.3 to about 0.5, c ranges from about 0.01 to about 0.09, and preferably from about 0.01 to about 0.05, and d is a number that satisfies valence requirements.

In a further preferred mixed-metal oxide embodiment, with reference to formula I, A is Ti and Ta in combination, Ti and Nb in combination, or Ta and Nb in combination, B is La, Ce, Pr, Nd, Sm, Sb, Sn, Bi, Co, Cr and Ag, and C is Ca, K or Mg. In this embodiment, x ranges from about 0.1 to about 0.96, and preferably from about 0.5 to about 0.96, a ranges from about 0.3 to about 0.5, c ranges from about 0.01 to about 0.09, and preferably from about 0.01 to about 0.05, and d is a number that satisfies valence requirements.

In a particularly preferred mixed-metal oxide embodiment, with reference to formula I, A is Ti, B is Sb, Sn, Bi, Co, Ag or Ce and C is Sr, Ca, Mg or Li. In this embodiment, x ranges from about 0.5 to about 0.9, a ranges from about 0.15 to about 0.4, c ranges from 0 to about 0.05, and d is a number that satisfies valence requirements.

In another particularly preferred mixed-metal oxide embodiment, with reference to formula I, A is Ta, B is Sb, Sn, Bi, Co, Ag or Ce and C is Sr, Ca, Mg or Li. In this embodiment, x ranges from about 0.5 to about 0.9, a ranges from about 0.15 to about 0.4, c ranges from 0 to about 0.05, and d is a number that satisfies valence requirements.

In a further particularly preferred mixed-metal oxide embodiment, with reference to formula I, A is Nb, B is Sb, Sn, Bi, Co, Ag or Ce and C is Sr, Ca, Mg or Li. In this embodiment, x ranges from about 0.5 to about 0.9, a ranges from about 0.15 to about 0.4, c ranges from 0 to about 0.05, and d is a number that satisfies valence requirements.

In still a further preferred embodiment, the nickel catalyst of the invention can be a material comprising a mixed-metal oxide compound having the formula II:

$$Ni_xTi_jTa_kNb_lLa^*_rSb_sSn_tBi_uCa_vK_wMg_yO_d \quad \text{(II)},$$

where "x" and "d" are as described above, and La*, j, k, l, r, s, t, u, v and w are described below, together with preferred relationships between respective elements. The various recited elements of formula II can be grouped in any of the various combinations and permutations of preferences, some of which are specifically set forth herein.

In formula II, each of "j", "k" and "l" represent a number ranging from 0 to about 0.8, preferably from 0 to about 0.5, and more preferably from 0 to about 0.4. The sum of (j+k+l) is at least about 0.04, preferably at least about 0.15, and more preferably at least about 0.3.

In formula II, La refers to one or more lanthanide series elements selected from the group consisting of $La_m$, $Ce_n$, $Pr_o$, $Nd_p$, $Sm_q$, and preferably. Each of "m", "n", "o", "p", "q", "r", "s" and "t" refer to numbers ranging from 0 to about 0.2, preferably from zero to about 0.1, and more preferably from zero to about 0.05. The sum of (m+n+o+p+q+r+s+t) is preferably at least about 0.005, more preferably at least about 0.01, and can, in some embodiments, be at least about 0.05.

In formula II, each of "u", "v" and "w" refer to numbers ranging from 0 to about 0.4, preferably from 0 to about 0.1 and more preferably from 0 to about 0.05.

The nickel catalyst of the invention is preferably a supported catalyst. The catalyst can therefore further comprise, in addition to one or more of the aforementioned compounds or compositions, a solid support or carrier. The support is preferably a porous support, with a pore size typically ranging, without limitation, from about 2 nm to about 100 nm and with a surface area typically ranging, without limitation, from about 5 m²/g to about 300 m²/g. The particular support or carrier material is not narrowly critical, and can include, for example, a material selected from the group consisting of silica, alumina, zeolite, activated carbon, titania, zirconia, magnesia, zeolites and clays, among others, or mixtures thereof. Preferred support materials include titania, zirconia, alumina or silica. In some cases, where the support material itself is the same as one of the preferred components (e.g., $Al_2O_3$ for Al as a minor component), the support material itself may effectively form a part of the catalytically active material. In other cases, the support can be entirely inert to the dehydrogenation reaction of interest. Titania is a particularly preferred support, and can be obtained, for example, from commercial vendors such as Norton, Degussa or Engelhardt.

General approaches for preparing the nickel catalysts of the present invention—as supported or unsupported catalysts—are well known in the art. Exemplary approaches include, for example, sol-gel, freeze drying, spray drying, precipitation, impregnation, incipient wetness, spray impregnation, ion exchange, wet mix/evaporation, dry mix/compacting, high coating, fluid bed coating, bead coating, spin coating, physical vapor deposition (sputtering, electron beam evaporation, laser ablation) and chemical vapor deposition, among others. The particular technical or non-technical technique employed is not narrowly critical. Preferred approaches, include, for example, impregnation techniques, precipitation techniques, sol-gel, evaporation, incipient wetness and spray drying, among others. The catalyst may take any suitable forms (e.g., granular, tablets, etc.), as discussed in greater detail below.

According to one exemplary approach for preparing a supported mixed-metal oxide catalyst of the invention, a composition comprising each of the desired elements of the active oxide components of the catalyst (i.e., the major component and one or more minor components) can be formed, and then optionally calcined to form the corresponding mixed-metal oxide. The pre-calcination composition can be formed, in the first instance for example, in a liquid state as a solution, dispersion, slurry or sol, by combining the major component, the first minor component(s), and optionally, the second and/or third minor component(s). The pre-calcination composition can then be formed as a solid having the same relative ratios of the various components, for example, by being impregnated into, situated on, or formed in-situ with the support or carrier (e.g., via precipitation or sol-gel approaches). For example, a pre-calcination composition formed as a solution or dispersion can be impregnated into or onto the support, and then dried. Alternatively, pre-calcination solution or dispersion can be precipitated, recovered and then dried. A pre-calcination sol can be cured (gelled) to form the corresponding solid composition. In any case, pre-calcination compositions can be otherwise treated (e.g., heated) as desired (e.g., to drive off solvents).

Preferred pre-calcination compositions of the invention can comprise, or alternatively consist essentially of, a compound represented by Formula I-B:

$$Ni_xA_aB_bC_c \quad \text{(I-B)},$$

or salts thereof, where "x", "A", "B", "C", "a", "b" and "c" are each as defined above in connection with the preferred mixed-oxide catalyst. A particularly preferred pre-calcination composition can comprise, or alternatively consist essentially of, a compound represented by Formula II-B:

$$Ni_xTi_jTa_kNb_lLa^*{}_sSb_rSn_sBi_tCa_uK_vMg_w \quad \text{(II-B)},$$

or salts thereof, where "x", "j", "k", "La*", "r", "s", "t", "u", "v" and "w" are each as defined above in connection with the preferred mixed-oxide catalyst. The preferred pre-calcination compositions can be in a liquid state (e.g. solution, dispersion, slurry or sol) or a solid state.

According to one method for forming the preferred pre-calcination composition, salts of the various elements are combined to form a solution or liquid dispersion thereof, ("precursor solutions"). The metal salt precursor solutions are preferably aqueous solutions, and can typically include metal cations with counterions selected from nitrates, acetates, oxalates, and halides, among others. The metal salt precursor solutions can also be organic solutions or sol-gels comprising such metal cations and counterions, as well as other counterions (e.g., alkoxides). When halides are used as a counterion, the resulting catalyst is preferably subsequently rinsed extensively (e.g., with water) to remove halide. Particularly preferred salts for Ni, Ti, Nb, Ta and Zr include, for example, nickel nitrate, titanium oxalate, niobium oxalate, tantalum oxalate, and zirconium oxalate. The mixed-metal salt solutions can then be impregnated into a support, preferably a titania support. The volume of mixed-metal salt solutions used for impregnating the catalyst will depend on the pore volume of the support, and can typically range from about 0.1 to about 2, preferably from about 0.1 to about 1 times the pore volume thereof. The pH is preferably maintained at about 2 to about 6. The catalyst-impregnated support can then be dried, preferably at reduced pressure (i.e., under vacuum), at a temperature ranging from about 20° C. to about 100° C. for a period of time ranging from about 5 minutes to about 2 hours to form a semi-solid or solid pre-calcination composition.

According to an alternative approach, various aqueous solutions comprised of water-soluble metal precursors can be combined in proper volumetric ratios to obtain combined solutions (or mixtures) having desired metal compositions. Water can be separated from the metal-salt components of the combined solutions (or mixtures) by lyophilization, precipitation and/or evaporation. Lyophilization refers to freezing the resulting mixture (e.g., under liquid nitrogen), and then placing the mixture in a high vacuum so that the water (ice) sublimes, leaving behind mixtures of dry metal precursors. Precipitation refers to separating dissolved metal ions by adding one or more chemical reagents that will precipitate sparingly soluble salts of the metal ions. Such chemical reagents may provide ions that shift ionic equilibrium to favor formation of insoluble metal salts (common ion effect), or may bind with metal ions to form uncharged, insoluble coordination compounds (complexation). In addition, such reagents may oxidize or reduce metal ions to form ionic species that produce insoluble salts. Other precipitation mechanisms include hydrolysis, in which metal ions react with water in the presence of a weak base to form insoluble metal salts, or the addition of agents (e.g., alcohols) that affect the polarity of the solvent. Regardless of the particular mechanism, the precipitate can be separated from the remaining solution by first centrifuging the solutions and then decanting the supernatant; residual water can be removed by evaporation of water from the precipitates to form a semi-solid or solid pre-calcination composition. Evaporation refers to removing water by heating and/or under vacuum to form a semi-sold or solid pre-calcination composition.

The solid pre-calcination composition can be calcined according to methods known in the art. Calcination conditions can affect the activity of the catalyst, and can be optimized by a person of skill in the art, particularly in connection with a particular catalyst composition and/or dehydrogenation reaction conditions. Calcination is, without limitation, preferably effected at temperatures ranging from about 250° C. to about 600° C., and more preferably from about 275° C. to about 400° C. The calcination is preferably effected for period of time, and at a temperature sufficient to provide the desired metal oxide catalyst composition. Typically, calcination is effected for a total, cumulative period of time of at least about 0.1 hour, and typically at least about 1 hour, with actual calcination times depending on temperature according to approaches known in the art. The calcination environment is preferably an oxidizing environment (e.g., comprising air or other source of molecular oxygen), but can also be an inert environment. In the case of inert calcination, oxidation of the metal components of the catalyst can be effected in situ during the reaction, by oxidizing under reaction conditions. Hence, calcination can be effected prior to loading the catalyst into a reaction zone, or alternatively, can be effected in situ in the reaction zone prior to the reaction.

Finally, regardless of the particular approach used to form the catalyst, the solid pre-calcination composition or the calcination product (catalyst) can be ground, pelletized, pressed and/or sieved to ensure a consistent bulk density among samples and/or to ensure a consistent pressure drop across a catalyst bed in a reactor. Further processing can also occur, as discussed below.

The active catalyst of the invention can be included in a catalyst composition comprising other, inactive components. The catalyst may, for example, be diluted (e.g., have its concentration reduced) with binders and/or inert fillers, which are known to those of skill in the art, including for example quartz chips, sand or cement. Diluents may be added to the catalyst in the range of from about 0 to about 30% by volume, preferably in the range of from about 10 to about 25% by volume. Preferred diluents can improve the heat removal or heat transfer of the catalyst to help avoid hot spots or to modify hot spots. Binders generally provide mechanical strength to the catalyst and may be added in the range of from about 0-30% by volume, preferably in the range of from about 5 to about 25% by volume. Useful binders include silica sol, silica, alumina, diamataceous earth, hydrated zirconia, silica aluminas, alumina phosphates, naturally occurring materials and cement and combinations thereof. See, e.g., the discussion of supports, shapes, binders and fillers in U.S. Pat. Nos. 5,376, 613, 5,780,700 and 4,250,346, each of which is incorporated herein by reference for all purposes. The percentages or amounts of binders, fillers or organics referred to herein relate to the starting ingredients prior to calcination. Thus, the above is not intended to imply statements on the actual bonding ratios, to which the invention is not restricted; for example during calcination other phases may form.

The catalyst or catalyst composition is provided to a reaction zone of a reactor. The reactor is preferably a fixed-bed flow reactor, but other suitable reactor designs—including batch reactors and flow reactors (e.g., fluidized bed reactors)—can also be employed. The catalyst is preferably provided in the reaction zone (e.g., in a fixed-bed) as a supported catalyst, but may also be provided as an unsupported catalyst (e.g., bulk, pelletized catalyst). The catalyst may take any form, including powder, split, granular, pellets or a shaped catalyst, such as tablets, rings, cylinders, stars, ripped bodies, extrudates, etc., each of which are known to those of skill in the art. For example, the shaping of the mixture of starting composition may be carried out by compaction (for example tableting or extrusion) with or without a prior kneading step, if necessary with addition of conventional auxiliaries (e.g., graphite or stearic acid or its salts as lubricants). In the case of unsupported catalysts, the compaction gives the desired catalyst geometry directly. Hollow cylinders may have an external diameter and length of from 2 to 10 mm and a wall thickness of from 1 to 3 mm. Generally, the mixture of starting composition metal may be shaped either before or after the calcination. This can be carried out, for example, by comminuting or grinding the mixture before or after calcination and applying it to inert supports to produce coated catalysts.

As discussed in greater detail below, co-catalysts can also be provided to the reaction zone, together with the catalyst of the present invention (in separate phases or as an integrated catalyst composition).

An alkane or other reactant to be dehydrogenated is provided to the reaction zone of the reactor containing the catalyst. Typically and preferably, the dehydrogenation substrate reactant is provided to the reaction zone as a gas or in a gaseous state. Liquid reactants can be vaporized by methods and devices known in the art and entrained in a moving stream of gaseous fluid.

The alkane can be substituted or unsubstituted. The alkane is preferably an alkane having from 2 to 6 carbon atoms (a "$C_2$ to $C_6$ alkane") or a substituted $C_2$ to $C_6$ alkane, and preferably an alkane having from 2 to 4 carbon atoms (a "$C_2$ to $C_4$ alkane") or a substituted $C_2$ to $C_4$ alkane. Preferred $C_2$ to $C_6$ alkane reactants include ethane, propane, isopropanol, n-butane, isobutane, and isopentane, with ethane being particularly preferred. The oxidative dehydrogenation reaction for conversion of ethane to ethylene is representative:

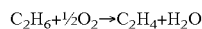

$$C_2H_6 + \tfrac{1}{2}O_2 \rightarrow C_2H_4 + H_2O$$

The corresponding alkenes for other preferred $C_2$ to $C_4$ alkanes include propylene (from propane), acetone (from isopropanol), 1-butene and/or 2-butene (from n-butane), isobutene (from isobutane), isoamylenes (from isopentane), and isoprene. Preferred substituted $C_2$ to $C_4$ alkanes include halide-substituted $C_2$ to $C_4$. For example, ethyl chloride can be oxidatively dehydrogenated using the catalysts and methods described herein to form the vinyl chloride.

Although the present invention is described and exemplified primarily in connection with dehydrogenation of the aforementioned alkanes, dehydrogenation of other alkanes using the catalysts and methods disclosed herein is also contemplated, and is within the scope of the invention. For example, cyclohexane can be oxidatively dehydrogenated over the nickel catalysts of the invention to form benzene. Moreover, the nickel catalysts of the invention can also be used for dehydrogenating other hydrocarbon substrates, such as alkenes, to one or more dehydrogenation product(s). The dehydrogenation of butene to form a butadiene, and the dehydrogenation of isoamylenes to form isoprene are exemplary.

An oxidant is also provided to the reaction zone of the reactor containing the catalyst. The oxidant is preferably a gaseous oxidant, but can also include a liquid oxidant or a solid-state oxidant. The gaseous oxidant is preferably molecular oxygen, and can be provided as oxygen gas or as an oxygen-containing gas. The oxygen containing gas can be air, or oxygen or air that has been diluted with one or more inert gases such as nitrogen. Other gaseous oxidants, such as $N_2O$ or $NO_x$ can also be used in the oxidative dehydrogenation reaction. In cases in which the alkane is oxidatively dehydrogenated in the substantial absence of a gaseous oxidant during the reaction (e.g., using a solid oxidant), the oxidant may be periodically regenerated—either by periodically withdrawing the catalyst from the reaction zone or by regenerating the catalyst in situ in the reaction zone (during or in-between reaction runs).

The sequence of providing the catalyst, reactant and oxidant to the reaction zone is not critical. Typically, the catalyst is provided in advance (or as noted above, even formed in situ in the reaction vessel from a pre-calcination composition), and the alkane gas and oxidant gas are provided subsequently—either together as a mixed gas through a common feed line, or alternatively, separately, but simultaneously, through different feed lines. In general, the simultaneous supply of alkane and gaseous oxidant to the reaction zone is referred to as "co-feed" regardless of the particular feed configuration employed.

The amount of catalyst loaded to the reaction zone of the reactor, together with the relative amounts of alkane (or other reactant) and oxidant provided to the reaction zone, can vary, and are preferably controlled—together with reaction conditions, as discussed below—to effect the dehydrogenation reaction with favorable and industrially attractive performance characteristics. In general, the catalyst loading to the reaction zone will vary depending on the type of reactor, the size of the reaction zone, the form of the catalyst, required contact times, and/or the desired amount or flow-rates of reactants and/or products. The absolute amount of alkane or other reactant and oxidant can likewise vary, depending primarily on the aforementioned factors, and can be optimized by persons of skill in the art to achieve the best performance. In general, lower oxidant concentration tends to limit the extent of over-oxidation, and therefore, favor higher alkene selectivity. Such lower oxidant concentrations, however, can also adversely affect the alkane conversion. For conversion of ethane to ethylene using molecular oxygen, for example, the molar ratio of ethane to molecular oxygen, $C_2H_6:O_2$, in the reaction zone (or being fed to the reaction zone) can range from about 1:1 to about 40:1, preferably from about 2:1 to about 40:1, more preferably from about 66:34 to about 20:1, and most preferably from about 5:1 to about 20:1. In some particularly preferred embodiments—such as where multi-stage reactors are employed, as discussed below—the $C_2H_6:O_2$ ratio can preferably range from about 5:1 to about 40:1, and preferably from about 5:1 to about 15:1, or alternatively, from about 10:1 to about 20:1. For the conversion of gaseous alkanes such as ethane with molecular oxygen, for example, the relative amounts of reactant and oxidant can alternatively be expressed in terms of volume percentages in reactor feed (for mixed-feed co-feed configuration) or in the reaction zone (regardless of co-feed configuration), with molecular oxygen preferably ranging from about 0.01% to about 34% by volume and the alkane preferably ranging from about 66% to about 99% by volume. The amount of molecular oxygen more preferably ranges from about 0.01% to about 20% by volume, and the amount of alkane more preferably ranges from about 80% to about 99% by volume. Flammability limits should be observed for safety reasons.

Other materials may also be provided to the reaction zone. For example, the reactor feed can also include diluents such as nitrogen, argon or carbon dioxide. For some reactions, and/or for some embodiments, discussed in greater detail below, the reactor feed may comprise water vapor, or amounts of various reaction products (e.g., alkenes such as ethylene, propylene or butenes).

The alkane and the gaseous oxidant contact the catalyst in a reaction zone of a reactor under controlled reaction conditions, and the alkane is dehydrogenated to form the corresponding alkene(s). Without being bound by theory, the alkane contacts the catalyst in the presence of the oxidant and is dehydrogenated; the hydrogen atoms combine with an oxygen from the oxidant to form the corresponding alkene(s) and water as reaction products. Contact between the reactant substrate, gaseous oxidant and catalyst can occur, for example, as a mixture of the feed gasses passes through or around the interstices of the fixed-bed catalyst and/or over an exposed surface of the catalyst. The contact time (or residence time) can vary, and can be optimized by persons of skill in the art. Generally, and without limitation, contact times can range from about 0.1 seconds to about 10 seconds, and preferably from about 0.5 seconds to about 5 seconds. Without limitation, the gas space velocity SV in the vapor phase reaction can range from about 100/hr to about 10,000/hr, preferably from about 300/hr to about 6,000/hr, and more preferably from about 300/hr to about 2,000/hr. Inert gas(es) can be used, if desired, as a diluting gas to adjust the space velocity. The temperature and pressure of the reaction zone can likewise vary, and can likewise be optimized by persons of skill in the art. Without limitation, the temperature preferably ranges from about 200° C. to about 500° C., more preferably from about 200° C. to about 400° C., even more preferably from about 250° C. to about 400° C., still more preferably from about 250° C. to about 350° C., and yet more preferably from about 275° C. to about 325° C., and most preferably from about 275° C. to about 300° C. In one embodiment of the invention, the temperature of the reaction zone during the dehydrogenation reaction is preferably controlled to be less than about 300° C. Alkane oxidative dehydrogenation is an exothermic reaction, and adequate heat transfer (cooling) can be achieved using methods known in the art, including for example, cooling with steam. Without limitation, the reaction pressure can range from atmospheric pressure to about 20 bar, and preferably ranges from about 1 bar to about 10 bar.

The relative alkane and oxidant feeds, catalyst loading, and reaction conditions are preferably controlled, individually and collectively among the various possible permutations, to achieve a reaction performance that is suitable for industrial applications. More specifically, the alkane and oxidant feeds, catalyst loading and reaction conditions are controlled such that the alkane is dehydrogenated to its corresponding alkene(s) with an alkane conversion of at least about 5%, preferably at least about 10%, and an alkene selectivity of at least about 70%, and preferably at least about 75%. Using the catalysts and process disclosed herein, the aforementioned reaction parameters can be controlled to achieve a conversion of at least about or greater than 15%, and more preferably at least about 20% or higher, and to achieve a selectivity for the alkene of at least about or greater than about 80%, preferably at least about or greater than about 85%, and most preferably at least about or greater than about 90%. Within experimental error, selectivity is substantially independent of conversion.

As used herein, "conversion" refers to the percentage of the amount of alkane provided to the reaction zone that is converted to carbon products, and can be expressed as follows:

$$\% \text{ conversion} = 100 \times \frac{\text{The molar alkane-equivalent sum (carbon basis) of all carbon-containing products, excluding the alkane in the effluent}}{\text{Moles of alkane in the reaction mixture which is fed to the catalyst in the reactor}}$$

As used herein, "selectivity" (also known as efficiency), or equivalently, "alkene selectivity" refers to the percentage of the amount of converted alkane (i.e., total carbon products) that is converted to the specifically desired alkene product, and can be expressed as follows:

$$\% \text{ selectivity} = 100 \times \frac{\text{Moles of desired alkene produced}}{\text{The molar alkene-equivalent sum (carbon basis) of all carbon-containing products, excluding the alkane in the effluent}}$$

These expressions are the theoretical expressions for selectivity and conversion. Simplified formulas have been used in the examples herein, and may be used by those of skill in the art for alkane oxydehydrogenation reactions where $CO_2$ is the primary side product—for example, where the only products observed in the ethane oxidative dehydrogenation (using an ethane and molecular oxygen gas feed) are ethylene and carbon dioxide. In such cases, the simplified formula for % conversion is % conversion=100×[(moles of alkene+((moles of carbon dioxide)/2))/(moles of alkane)]. The simplified formula for % selectivity is % selectivity=100×[(moles of alkene)/(moles of alkene+((moles of carbon dioxide)/2))]. When the alkane is ethane or propane, only one dehydrogenation product is possible, and the calculations are straightforward. When butane is the alkane, however, the dehydrogenation product can be one or more of 1-butene, 2-butene or 1,3-butadiene. Thus, for butane dehydrogenation reactions, the percentages for selectivity and conversion may be based on one or more of these butane dehydrogenation products.

The nickel oxide/mixed-metal oxide catalysts of the present invention offer significant performance advantages as compared to current industrially-important (V—Mo) catalysts. For example, the catalysts of the invention can result in about a 20% conversion with about a 90% selectivity, as compared to about a 5% conversion with a 90% selectivity of the current industrially-important alternative. Moreover, the space-time yield achieved based on bulk-scale testing of the invention catalysts in laboratory-scale equipment is about 300 kg ethylene produced per m³ of catalyst per hour—an improvement of a factor of about ten (10) as compared to known MoV-based catalysts.

The nickel oxide/mixed-metal oxide catalysts of the present invention are stable with respect to dehydrogenation activity and performance characteristics. Stability of the catalyst is demonstrated by lifetime testing, in which a $C_2$ to $C_4$ alkane or a substituted $C_2$ to $C_4$ alkane and a gaseous oxidant are co-fed to a reaction zone containing the catalyst while maintaining the reaction zone (and the catalyst) at temperature ranging from about 200° C. to about 500° C., preferably from about 250° C. to about 350° C., and more preferably from about 250° C. to about 300° C. The alkane is contacted with the catalyst in the presence of the gaseous oxidant to dehydrogenate the alkane and to form the corresponding alkene. The alkene, unreacted alkane and unreacted gaseous oxidant are exhausted or otherwise removed from the reaction zone. The steps of co-feeding the reactants, dehydrogenating the alkane, and exhausting the alkene and unreacted reactants are effected for a cumulative reaction period of not less than about 200 hours, preferably not less than about 400 hours, more preferably not less than about 600 hours, even more preferably not less than about 1000 hours, and most preferably not less than about 2000 hours. In commercial industrial-scale applications, the catalyst is preferably stable for at least about 5000 hours, and more preferably at least about 8000 hours.

Significantly, the nickel-containing mixed-metal oxide catalyst of the present invention has activity for selectively converting alkane to the corresponding alkene/olefin (e.g., ethane to ethylene) even in the presence of substantial amounts of alkene/olefin (e.g., ethylene) in the reaction zone. Specifically, the alkane can be oxidatively dehydrogenated to form the corresponding alkene in the reaction zone—even when the reaction zone comprises the corresponding alkene in a molar concentration of at least about 5%, relative to total moles of hydrocarbon, during the oxydehydrogenation—with an alkane conversion of at least about 5% and an alkene selectivity of at least about 50%. A conversion of at least about 5% and a selectivity of at least about 50% can likewise be achieved where the molar concentration of the corresponding alkene in the reaction zone ranges from about 5% to about 50%, or where the molar concentration thereof is at least about 10%, at least about 20%, at least about 30%, at least about 40% or at least about 50%, relative to total moles of hydrocarbon. Moreover, alkane conversions as high as 10% with alkene selectivity as high as 70% can be achieved where the molar concentration the corresponding alkene in the reaction zone is at least about 30% relative to total moles of hydrocarbon. The relatively low product-sensitivity of the catalyst activity is surprising, particularly with respect to ethane conversion, because ethylene is typically more reactive than ethane over most catalysts.

The lack of product-inhibition on catalyst activity can be advantageously employed in a number of ways. First, for example, a less-pure, mixed feed comprising both alkane and the corresponding alkene can be selectively enriched in the alkene. For example, a 70% ethane/30% ethylene feed stream, by volume, can be enriched by conversion to a 60% ethane/40% ethylene product stream, by volume, or further, to a 50% ethane/50% ethylene product stream, by volume. As a more specific example, raffinate II (a mixture of butane, 2-butenes and 1-butene gasses) can be selectively enriched in the butenes at the expense of butane, ultimately resulting in a more uniform stream composition. Such enrichment schemes may be particularly important if employed in connection with separation schemes that are more effective with streams having higher alkene content.

As another embodiment, exemplary of the advantageous catalytic activity of the catalyst, a single-stage reactor system can be configured to recycle the product stream (or a portion thereof) back to the feed stream, resulting in an overall improvement in conversion and selectivity. More specifically, with reference to FIG. 1A, the alkane (e.g., $C_2H_6$) and gaseous oxidant (e.g., $O_2$) are co-fed through feed conduits 5 to a reaction zone 10 containing the catalyst 100, the alkane is dehydrogenated in the reaction zone 10 to form the corresponding alkene, the resulting product stream 15 (comprising the corresponding alkene, unreacted alkane and optionally any excess gaseous oxidant) is exhausted from the reaction zone 10, and a portion or all of the alkene- and unreacted-alkane-containing product stream 15 is then recycled back to the reaction zone via recycle line 25 (and is typically recombined with a fresh feed stream 5). As a variation of the basic recycling embodiment discussed in the immediately-preceding paragraph, the product stream can be partially separated after being exhausted and before being recycled.

In a further, and generally preferred embodiment exemplifying the aforementioned advantage, a multi-stage reaction system can be effected, in which the product stream from a first reaction zone, or a portion thereof, becomes the feed stream for a second reaction zone. More specifically, with reference to FIG. 1B, an alkane (e.g., $C_2H_6$) and a gaseous oxidant (e.g., $O_2$) can be co-fed through feed conduits 5 to a first reaction zone 10, in which the alkane is dehydrogenated to form the corresponding alkene, and the first product stream 15 comprising the corresponding alkene and unreacted alkane from the first reaction zone 10 is exhausted therefrom. The alkene- and unreacted-alkane-containing product stream 15 from the first reaction zone is then fed to a second reaction zone 20—preferably with a co-feed of fresh gaseous oxidant via feed conduit 5' to the second reaction zone 20. The alkane is further dehydrogenated in the second reaction zone 20 to form the corresponding alkene therein. The alkene product is exhausted from the second reaction zone 20 as a product stream 15'. Additional stages of reaction zones (in one or more reactors) can likewise be added. The second (or further additional) reaction zone(s) preferably comprises the alkene at a molar concentration of at least about 5% relative to total moles hydrocarbon, and can be higher up to about 50%, as well as at one or more of the intermediate levels as described above. Significantly, because fresh gaseous oxidant (e.g., molecular oxygen) can be added between each stage of the multi-stage reactor, the amount of gaseous oxidant can be controlled at each stage to achieve an optimized selectivity and conversion for the dehydrogenation reaction occurring in that stage. This is particularly advantageous because low oxidant concentrations in the feed typically favor more selective oxydehydrogenation reactions, with less formation of side-product (e.g., carbon dioxide). In preferred embodiments for ethane dehydrogenation to ethylene, the molar concentration of oxygen in the first and second reaction zones is controlled to range from about 3% to about 40%, preferably from about 3% to about 20%, more preferably from about 5% to about 20%, and most preferably from about 8% to about 15%, in each case relative to ethane. The overall conversion and selectivity for ethane dehydrogenation to ethylene with a multi-stage, multi-low-level oxygen co-feed system as described herein is preferably at least about 5% alkane conversion and at least about 70% alkene selectivity, preferably at least about 80% alkene selectivity, preferably at least about 85% alkene selectivity, and more preferably at least about 90% alkene selectivity, and in another embodiment, preferably at least about 10% alkane conversion and at least about 80% alkene selectivity, preferably at least about 85% alkene selectivity, and more preferably at least about 90% alkene selectivity. In particularly preferred embodiments, the overall conversion is at least about 30%, more preferably at least about a value ranging from about 30% to about 45%, and the overall selectivity is at least about 70%, more preferably at least about a value ranging from about 70% to about 85%.

Regardless of the particular reactor-configuration (e.g., single-stage, single-stage with recycle, multi-stage, multi-stage with multi-oxidant feed, etc.), the resulting product stream typically comprises the product alkene/olefin of interest, together with unreacted alkane, possibly unreacted gaseous oxidant, as well as any side-product (e.g., $CO_2$). The desired alkene product can be separated from the reaction product stream by methods known in the art. Preferably, for example, the alkene product can be recovered from the reaction product stream by cryogenic separation, by pressure-swing adsorption (e.g., on zeolites), by selective absorption. Additionally, or alternatively, the reaction product stream can be used, without further separation or with partial separation (e.g., with removal of $CO_2$) as a feedstream to a downstream reactor, where the alkene product can be reacted further (e.g., as discussed below).

The oxydehydrogenation products of the reactions disclosed herein (e.g., ethylene, propylene, butenes, pentenes) can be further reacted to form a number of commercially important downstream products.

Ethylene produced by the oxydehydrogenation of ethane using the nickel oxide/mixed-metal oxide catalyst of the present invention can, for example, be further reacted to form polyethylene, styrene, ethanol, acetaldehyde, acetic acid, vinyl chloride, ethylene oxide, ethylene glycol, ethylene carbonate, ethyl acetate and vinyl acetate, among others. More specifically, ethylene can be formed by oxidatively dehydrogenating ethane in the presence of a catalyst comprising (i) Ni, a Ni oxide, a Ni salt or mixtures thereof, and (ii) elements or compounds selected from the group consisting of Ti, Ta, Nb, Hf, W, Y, Zn, Zr, Al, oxides thereof, and salts thereof, or mixtures of such elements or compounds. The catalyst can be more specifically characterized as described above. The ethylene can be optionally purified, and then further reacted to form a downstream reaction product of ethylene according to one or more of the following schemes.

Polyethylene. Ethylene can be polymerized to form polyethylene according to methods known in the art using a catalyst having activity for polymerizing ethylene to polyethylene. Exemplary polymerization approaches include free-radical polymerization, and polymerization over Ziegler (i.e., metal alkyl) catalysts. Styrene. Ethylene can be reacted with benzene in the presence of acid catalysts such as aluminum chloride or zeolites to form ethylbenzene, which can be catalytically dehydrogenated (using a catalyst of the invention or known dehydrogenation catalysts) to form styrene. Styrene can also be formed directly from the reaction of ethylene with benzene. Ethanol. Ethylene can be hydrated to form ethanol according to methods known in the art using a catalyst comprising an element or compound having activity for hydrating ethylene to ethanol. Preferred ethylene hydration catalysts include oxides of B, Ga, Al, Sn, Sb or Zn, or mixtures of such oxides. Water is preferably cofed to the reaction zone during the hydration reaction. Acetaldehyde. Acetaldehyde can be formed from ethylene according to methods known in the art—either directly, or through an ethanol intermediate. In a direct route, ethylene is oxidized to acetaldehyde using a catalyst comprising an element or compound having activity for oxidizing ethylene to acetaldehyde. Preferred ethylene oxidation catalysts for acetaldehyde formation include oxides of Pd, Cu, V or Co, or mixtures of such oxides. In an alternative, indirect route, ethylene is hydrated to form ethanol (as described above) and ethanol is then oxidized to form acetaldehyde in the presence of a catalyst having activity for oxidizing ethanol to acetaldehyde. Preferred ethanol oxidation catalysts for acetaldehyde formation include metals and/or metal oxides of Cu, Co, Ag, Re, Ru, Pt, Bi, Ce, Sb, In, Pd, Rh, Ir, V, Cr or Mn, or mixtures of such oxides. Acetic Acid. Ethylene can be oxidized to form acetic acid according to methods known in the art using a catalyst comprising an element or compound having activity for oxidizing ethylene to acetic acid. The catalyst preferably comprises a noble metal or an oxide thereof, and more preferably, Pd or Pt or oxides thereof. Water is preferably co-fed to the reaction zone during the ethylene oxidation reaction. Vinyl Chloride. Ethylene can be chlorinated or oxychlorinated to form vinyl chloride according to methods known in the art. In a chlorination reaction, chlorine or other chlorinating agent are preferably co-fed to the reaction zone, and ethylene is chlorinated in the presence of a catalyst having activity for chlorinating ethylene to vinyl chloride, or alternatively, in the absence of a catalyst. Preferred ethylene chlorination catalysts for preparing vinyl chloride comprise a metal halide or metal oxyhalide, and preferably, a halide or oxyhalide of Cu, Fe or Cr. In an oxychlorination reaction, a gaseous oxidant and HCl or other chlorinating agent are preferably co-fed to the reaction zone, and ethylene is oxychlorinated in the presence of a catalyst having activity for oxychlorinating ethylene to vinyl chloride. Preferred ethylene oxychlorination catalysts for preparing vinyl chloride comprise a metal halide or metal oxyhalide, and most preferably, a halide or oxyhalide of Cu, Fe or Cr. Ethylene Oxide. Ethylene can be oxidized to form ethylene oxide according to methods known in the art using a catalyst comprising an element or compound having activity for oxidizing ethylene to ethylene oxide. The catalyst preferably comprises Ag, a halide thereof, an oxide thereof or a salt thereof. Ethylene Glycol. Ethylene glycol can be produced by oxidizing ethylene to form ethylene oxide as described above, and hydrating ethylene oxide to form ethylene glycol. Alternatively, ethylene can be converted into ethylene glycol directly, in a single-step process. Ethylene Carbonate. Ethylene carbonate can be produced from ethylene by reacting ethylene with carbon dioxide or carbon monoxide to form ethylene carbonate, or alternatively by forming ethylene glycol as described above and then reacting the ethylene glycol with phosgene. Ethyl acetate. Ethyl acetate can be formed from acetic acid, prepared as described above, according to methods known in the art. Vinyl acetate. Vinyl acetate can be prepared by vapor-phase reaction of ethylene, acetic acid and oxygen over a Pd catalyst.

Propylene produced by the oxydehydrogenation of propane using the nickel oxide/mixed-metal oxide catalyst of the present invention can, for example, be further reacted to form polypropylene, acrolein, acrylic acid, acetone, propylene oxide and propylene carbonate, among other downstream reaction products of propylene. More specifically, propylene can be formed by oxidatively dehydrogenating propane in the presence of a catalyst comprising (i) Ni, a Ni oxide, a Ni salt or mixtures thereof, and (ii) elements or compounds selected from the group consisting of Ti, Ta, Nb, Hf, W, Y, Zn, Zr, Al, oxides thereof, and salts thereof, or mixtures of such elements or compounds. The catalyst can be more specifically characterized as described above. The propylene can be optionally purified, and then further reacted according to one or more of the following schemes.

Polypropylene. Propylene can be polymerized to form polypropylene according to methods known in the art using a catalyst having activity for polymerizing propylene to polypropylene. Exemplary propylene polymerization catalysts include, for example, aluminum alkyl catalysts. Acrolein. Propylene can be oxidized to form acrolein according to methods known in the art using a catalyst comprising an element or compound having activity for oxidizing propylene to acrolein. The catalyst preferably comprises an oxide of Bi, Mo, Te or W, or mixtures of such oxides. Acrylic Acid. Propylene can be oxidized to form acrylic acid according to methods known in the art using a catalyst comprising an element or compound having activity for oxidizing propylene to acrylic acid. The catalyst preferably comprises an oxide of Mo, V or W, or mixtures of such oxides. Acetone. Acetone can be produced from propylene by oxidation of propylene. Propylene Oxide. Propylene can be oxidized to form propylene oxide according to methods known in the art using a catalyst comprising an element or compound having activity for oxidizing propylene to propylene oxide. The catalyst preferably comprises TiSi oxide or PdTiSi oxide catalysts. Propylene carbonate. Propylene carbonate can be formed by preparing propylene oxide as described above, and by reacting the propylene oxide with carbon dioxide. Propylene can also be directly converted to propylene carbonate in a single-step process.

The oxydehydrogenation products of isobutane and n-butane can likewise be further reacted. Isobutene can be further reacted, for example, to form methacrylic acid. n-Butene can be further reacted, for example, to form butanol, butanediol, butadiene, methylethylketone (MEK), methylvinylketone (MEK), furane, or crotonaldehyde. More specifically, isobutene or n-butene can be formed by oxidatively dehydrogenating the respective butane in the presence of a catalyst comprising (i) Ni, a Ni oxide, a Ni salt or mixtures thereof, and (ii) elements or compounds selected from the group consisting of Ti, Ta, Nb, Hf, W, Y, Zn, Zr, Al, oxides thereof, and salts thereof, or mixtures of such elements or compounds. The catalyst can be more specifically characterized as described above. The isobutene or n-butene can be optionally purified, and then further reacted according to one or more of the following schemes.

Methacrylic Acid. Isobutene can be oxidized to form methacrylic acid according to methods known in the art using a catalyst comprising an element or compound having activity for oxidizing isobutene to methacrylic acid. The catalyst preferably comprises a polyoxometallate (POM), and in particular, PVMo- or PVW-containing POM. Butanol. Butanol can be prepared by hydrating n-butene to form butanol. Butadiene. n-Butene can be oxidatively dehydrogenated to form butadiene according to the methods of the present invention (and/or according to other methods known in the art) using a catalyst comprising an element or compound having activity for oxidatively dehydrogenating n-butene to butadiene. The catalyst preferably comprises (i) Ni, a Ni oxide, a Ni salt or mixtures thereof, and (ii) elements or compounds selected from the group consisting of Ti, Ta, Nb, Hf, W, Y, Zn, Zr, Al, oxides thereof, and salts thereof, or mixtures of such elements or compounds. The catalyst can be more specifically characterized as described above. Butanediol. Butane diol can be prepared by forming butadiene, as described above, and then hydrating butadiene to form butanediol. Methylethylketone (MEK). n-Butene can be oxidatively dehydrogenated to form butadiene (as described above), and butadiene can be oxidized to form methylethylketone (MEK) according to the methods known in the art using a catalyst comprising an element or compound having activity for oxidation of butadiene to MEK. The catalyst preferably comprises Bi/Mo, MoN/W, VPO or a polyoxometallate. Methylvinylketone (MVK). n-Butene can be oxidatively dehydrogenated to form butadiene (as described above), and butadiene can be oxidized to form methylvinylketone (MVK) according to the methods known in the art using a catalyst comprising an element or compound having activity for oxidation of butadiene to MVK. The catalyst preferably comprises Bi/Mo, Mo/V/W, VPO or a polyoxometallate. Furane. Furane can be prepared by oxidizing n-butene. Crotonaldehyde. Crotonaldehyde can be prepared by forming butadiene, as described above, and then oxidizing butadiene to form crotonaldehyde.

In each of the aforementioned further reactions of the oxydehydrogenation products (e.g., ethylene, propylene, butenes), the reactants are preferably provided to the reaction zone in the presence of the respective catalysts. The catalyst(s) for the downstream reaction(s) can be co-catalysts provided to the same reaction zone in which the oxydehydrogenation catalyst is situated, or alternatively, can be provided to a physically separate, down-stream reaction zone. If provided as a co-catalyst in the same reaction zone, the catalyst for the downstream reaction can be prepared and provided to the reaction zone as a separate composition from the catalyst of the present invention, or alternatively, can be prepared and provided to the reaction zone as a single composition in separate phases or as an integrated catalyst composition having activity for both the oxydehydrogenation reaction and the respective downstream reaction of interest. Regardless of whether the oxydehydrogenation reaction and the downstream reaction of interest are carried out in the same or in separate reaction zones, the oxydehydrogenation reaction and the downstream reaction(s) are preferably performed sequentially (e.g., where an alkane is oxyhydrogenated to form the corresponding alkene as the oxydehydrogenation product, and the alkene is then further reacted to form the downstream product of interest).

The following examples illustrate the principles and advantages of the invention.

EXAMPLES

General.

In general, catalysts were prepared in small quantities (e.g. ~100 mg) or in larger, bulk quantities (e.g., ~20 g) using conventional precipitation and/or evaporation approaches. Small quantity catalysts were generally prepared with automated liquid dispensing robots (Cavro Scientific Instruments) in glass vials contained in wells of an aluminum substrate. Catalysts were screened for activity for oxidative dehydrogenation of ethane (ODHE), regardless of the scale of preparation, in a parallel fixed bed reactor substantially as disclosed in PCT patent application WO 99/64160 (Symyx Technologies, Inc.).

Example 1

ODHE over NiNbTi Oxide and NiTaTi Oxide Catalysts. (#14839/15156)

Catalysts were prepared in small quantities (~100 mg) from nickel nitrate ([Ni]=1.0 M), titanium oxalate ([Ti]=0.713 M), niobium oxalate ([Nb]=0.569 M), and tantalum oxalate ([Ta]=0.650 M) aqueous stock solutions by precipitation with tetramethylammonium hydroxide ([NMe$_4$OH]=1.44M). Briefly, a library of catalyst precursors were prepared by dispensing various amounts of aqueous stock solutions using a Cavro automated liquid handling robot to an array of glass vials held in an aluminum substrate. The precipitating agent, NMe$_4$OH solution, was added to the various catalyst precursor compositions in about 1.3 equivalent of acid and metal ions, by high-speed injection from a syringe head. The high-speed injection of the base provides mixing of the catalyst precursor solution and precipitation agents, thereby effecting precipitation of solid catalyst materials. To further insure well mixing, additional liquid (e.g., distilled water was, in some cases, also injected into the vial containing the metal precursor solution and base precipitating agent. The resulting precipitate mixtures were allowed to settle at about 25° C. for about 2 hours, and were then centrifuged at 3000 rpm to separate solid precipitate from the solution. The solution was decanted and solids were dried under vacuum at 60° C. in a vacuum oven. Table 1A summarizes the composition and amounts of the various catalyst compositions.

In a first set of experiments, the dried catalyst compositions were calcined to 300° C. in an atmosphere of air with an oven temperature profile: ramp to 300° C. at 2° C./min and dwell at 300° C. for 8 hours. Samples were ground with a spatula. The mixed metal oxide catalysts (~50 mg) were screened in the fixed bed parallel reactor. The performance characteristics of these catalysts for ethane oxidative dehydrogenation at 300° C. with relative flowrates of ethane:nitrogen:oxygen of 0.42: 0.54:0.088 sccm are summarized in Table 1B (ethane conversion) and Table 1C (ethylene selectivity).

After initial screening, these catalyst were subsequently recalcined to 400° C. with a similar temperature profile. The performance characteristics of these catalysts for ethane oxidative dehydrogenation in the parallel fixed bed reactor at 300° C. with relative flowrates of ethane:nitrogen:oxygen of 0.42:0.54:0.088 sccm are summarized in Table 1D (ethane conversion) and Table 1E (ethylene selectivity).

TABLE 1A

Catalyst composition (mole fraction) of Ni-Nb-Ti and Ni-Ta-Ti oxide mixtures and sample mass, "m" (mg) used in parallel fixed bed reactor screen.

| Row | Col | 1 | 2 | 3 | 4 | 5 | 6 |
|---|---|---|---|---|---|---|---|
| 1 | Ni | 1.0000 | 0.8969 | 0.7944 | 0.6927 | 0.5917 | 0.4914 |
|   | Nb | 0.0000 | 0.0000 | 0.0000 | 0.0000 | 0.0000 | 0.0000 |
|   | Ta | 0.0000 | 0.1031 | 0.2056 | 0.3073 | 0.4083 | 0.5086 |
|   | Ti | 0.0000 | 0.0000 | 0.0000 | 0.0000 | 0.0000 | 0.0000 |
|   | m  | 49.5 | 50.4 | 50 | 49.4 | 50.1 | 50.1 |
| 2 | Ni | 0.9119 | 0.9091 | 0.8052 | 0.7021 | 0.5997 | 0.4980 |
|   | Nb | 0.0881 | 0.0000 | 0.0000 | 0.0000 | 0.0000 | 0.0000 |
|   | Ta | 0.0000 | 0.0000 | 0.1042 | 0.2076 | 0.3103 | 0.4124 |
|   | Ti | 0.0000 | 0.0909 | 0.0906 | 0.0903 | 0.0900 | 0.0896 |
|   | m  | 50.2 | 49.5 | 50.3 | 50.5 | 49.6 | 49.8 |
| 3 | Ni | 0.8214 | 0.8188 | 0.8163 | 0.7117 | 0.6079 | 0.5048 |
|   | Nb | 0.1786 | 0.0890 | 0.0000 | 0.0000 | 0.0000 | 0.0000 |
|   | Ta | 0.0000 | 0.0000 | 0.0000 | 0.1052 | 0.2097 | 0.3135 |
|   | Ti | 0.0000 | 0.0921 | 0.1837 | 0.1830 | 0.1824 | 0.1817 |
|   | m  | 49.5 | 49.5 | 49.3 | 50.4 | 50 | 50.3 |
| 4 | Ni | 0.7284 | 0.7261 | 0.7239 | 0.7216 | 0.6163 | 0.5118 |
|   | Nb | 0.2716 | 0.1805 | 0.0900 | 0.0000 | 0.0000 | 0.0000 |
|   | Ta | 0.0000 | 0.0000 | 0.0000 | 0.0000 | 0.1063 | 0.2119 |
|   | Ti | 0.0000 | 0.0934 | 0.1861 | 0.2784 | 0.2774 | 0.2764 |

TABLE 1A-continued

Catalyst composition (mole fraction) of Ni-Nb-Ti and Ni-Ta-Ti oxide mixtures and sample mass, "m" (mg) used in parallel fixed bed reactor screen.

| Row | Col | 1 | 2 | 3 | 4 | 5 | 6 |
|---|---|---|---|---|---|---|---|
|   | m  | 49.3 | 49.4 | 49.3 | 50.1 | 49.4 | 49.3 |
| 5 | Ni | 0.6329 | 0.6309 | 0.6289 | 0.6270 | 0.6250 | 0.5189 |
|   | Nb | 0.3671 | 0.2744 | 0.1824 | 0.0909 | 0.0000 | 0.0000 |
|   | Ta | 0.0000 | 0.0000 | 0.0000 | 0.0000 | 0.0000 | 0.1074 |
|   | Ti | 0.0000 | 0.0946 | 0.1887 | 0.2821 | 0.3750 | 0.3736 |
|   | m  | 50.3 | 50.3 | 49.3 | 49.9 | 49.6 | 50.4 |
| 6 | Ni | 0.5348 | 0.5330 | 0.5314 | 0.5297 | 0.5280 | 0.5263 |
|   | Nb | 0.4652 | 0.3710 | 0.2774 | 0.1843 | 0.0919 | 0.0000 |
|   | Ta | 0.0000 | 0.0000 | 0.0000 | 0.0000 | 0.0000 | 0.0000 |
|   | Ti | 0.0000 | 0.0959 | 0.1913 | 0.2860 | 0.3801 | 0.4737 |
|   | m  | 50.7 | 22.6 | 50.4 | 49.5 | 49.9 | 50.6 |

TABLE 1B

Ethane conversion for the catalysts in Table 1A. Test conditions: 300° C. with ethane/nitrogen/oxygen flow of 0.42/0.54/0.088 sccm.

Ethane Conversion (%) of Ni-Nb-Ta-Ti Oxide Mixtures

|   | 1 | 2 | 3 | 4 | 5 | 6 |
|---|---|---|---|---|---|---|
| 1 | 9.4 | 17.9 | 19.0 | 19.1 | 18.6 | 16.8 |
| 2 | 16.3 | 15.7 | 18.1 | 17.1 | 17.6 | 19.2 |
| 3 | 18.6 | 18.3 | 18.9 | 17.6 | 19.3 | 18.6 |
| 4 | 19.4 | 18.2 | 19.4 | 18.6 | 18.9 | 19.2 |
| 5 | 19.4 | 18.9 | 16.5 | 19.1 | 18.6 | 17.1 |
| 6 | 19.0 | 16.2 | 17.9 | 18.0 | 16.8 | 16.8 |

TABLE 1C

Ethylene selectivity for the catalysts in Table 1A. Test conditions: 300° C. with ethane/nitrogen/oxygen flow of 0.42/0.54/0.088 sccm.

Ethylene Selectivity (%) of Ni-Nb-Ta-Ti Oxide Mixtures

|   | 1 | 2 | 3 | 4 | 5 | 6 |
|---|---|---|---|---|---|---|
| 1 | 47.2 | 82.8 | 84.3 | 83.7 | 84.7 | 83.3 |
| 2 | 79.5 | 78.5 | 84.2 | 85.0 | 81.2 | 84.9 |
| 3 | 84.5 | 83.6 | 83.5 | 84.1 | 84.4 | 85.0 |
| 4 | 84.2 | 84.1 | 83.4 | 84.1 | 84.8 | 84.8 |
| 5 | 84.8 | 84.9 | 82.1 | 82.3 | 82.1 | 83.8 |
| 6 | 82.6 | 81.1 | 79.9 | 80.5 | 78.8 | 79.0 |

TABLE 1D

Ethane conversion for the catalysts in Table 1A but recalcined to 400° C. Test conditions: 300° C. with ethane/nitrogen/oxygen flow of 0.42/0.54/0.088 sccm.

Ethane Conversion (%) of Ni-Nb-Ta-Ti Oxide Mixtures

|   | 1 | 2 | 3 | 4 | 5 | 6 |
|---|---|---|---|---|---|---|
| 1 | 5.8 | 11.9 | 12.2 | 12.4 | 11.8 | 9.6 |
| 2 | 9.8 | 9.2 | 11.5 | 9.2 | 11.3 | 13.0 |
| 3 | 12.0 | 12.7 | 11.1 | 12.0 | 13.8 | 12.3 |
| 4 | 12.8 | 11.5 | 13.3 | 11.1 | 10.1 | 11.9 |
| 5 | 13.5 | 12.0 | 12.9 | 11.1 | 11.9 | 10.4 |
| 6 | 13.0 | 9.0 | 13.0 | 13.6 | 11.3 | 11.0 |

TABLE 1E

Ethylene selectivity for the catalysts in Table 1A but recalcined to 400° C. Test conditions: 300° C. with ethane/nitrogen/oxygen flow of 0.42/0.54/0.088 sccm.

Ethylene Selectivity (%) of Ni-Nb-Ta-Ti Oxide Mixtures

|   | 1 | 2 | 3 | 4 | 5 | 6 |
|---|---|---|---|---|---|---|
| 1 | 34.2 | 83.1 | 85.4 | 84.4 | 85.2 | 85.1 |
| 2 | 77.2 | 75.3 | 84.9 | 86.4 | 80.8 | 84.6 |
| 3 | 85.1 | 84.1 | 82.7 | 84.0 | 83.8 | 84.1 |
| 4 | 85.4 | 84.5 | 83.7 | 82.2 | 83.9 | 84.5 |
| 5 | 86.4 | 85.9 | 79.3 | 78.7 | 80.4 | 83.1 |
| 6 | 80.1 | 78.4 | 79.3 | 77.1 | 72.1 | 71.2 |

Another library of NiNbTi oxide catalysts was prepared substantially as described above and having the composition and amounts summarized in Table 1F. The performance characteristics of these catalysts for ethane oxidative dehydrogenation in the parallel fixed bed reactor at 300° C. with relative flowrates of ethane:nitrogen:oxygen of 0.42:0.54:0.088 sccm are summarized in Table 1G (ethane conversion) and Table 1H (ethylene selectivity).

TABLE 1F

Catalyst composition (mole fractions) of NiNbTi oxide catalysts and sample mass (mg) used in parallel fixed bed reactor screen.

| Row | Column | 1 | 2 | 3 | 4 | 5 | 6 |
|---|---|---|---|---|---|---|---|
| 1 | Ni | 1.000 | | | | | |
|   | Nb | 0.000 | | | | | |
|   | Ti | 0.000 | | | | | |
|   | mass (mg) | 49.9 | | | | | |
| 2 | Ni | 0.841 | 0.885 | | | | |
|   | Nb | 0.000 | 0.115 | | | | |
|   | Ti | 0.159 | 0.000 | | | | |
|   | mass (mg) | 45.0 | 56.3 | | | | |
| 3 | Ni | 0.714 | 0.748 | 0.784 | | | |
|   | Nb | 0.000 | 0.103 | 0.216 | | | |
|   | Ti | 0.286 | 0.150 | 0.000 | | | |
|   | mass (mg) | 49.2 | 49.3 | 45.0 | | | |
| 4 | Ni | 0.612 | 0.637 | 0.665 | 0.696 | | |
|   | Nb | 0.000 | 0.093 | 0.194 | 0.304 | | |
|   | Ti | 0.388 | 0.270 | 0.141 | 0.000 | | |
|   | mass (mg) | 49.6 | 51.4 | 51.9 | 50.8 | | |
| 5 | Ni | 0.526 | 0.546 | 0.568 | 0.592 | 0.617 | |
|   | Nb | 0.000 | 0.085 | 0.176 | 0.275 | 0.383 | |
|   | Ti | 0.474 | 0.369 | 0.256 | 0.133 | 0.000 | |
|   | mass (mg) | 44.9 | 46.3 | 46.7 | 44.0 | 47.0 | |
| 6 | Ni | 0.455 | 0.471 | 0.488 | 0.506 | 0.526 | 0.547 |
|   | Nb | 0.000 | 0.078 | 0.161 | 0.251 | 0.348 | 0.453 |
|   | Ti | 0.545 | 0.452 | 0.351 | 0.243 | 0.126 | 0.000 |
|   | mass (mg) | 48.8 | 50.5 | 46.1 | 48.5 | 52.0 | 54.1 |

TABLE 1G

Ethane conversion for catalysts listed in Table 1F. Test conditions: 300° C. with ethane:nitrogen:oxygen flow of 0.42:0.54:0.088 sccm.

|   | 1 | 2 | 3 | 4 | 5 | 6 |
|---|---|---|---|---|---|---|
| 1 | 8.4 | | | | | |
| 2 | 16.6 | 18.2 | | | | |
| 3 | 17.5 | 16.5 | 16.9 | | | |
| 4 | 16.7 | 16.3 | 17.0 | 16.1 | | |
| 5 | 15.9 | 16.2 | 17.1 | 15.9 | 17.9 | |
| 6 | 16.6 | 17.5 | 15.5 | 15.2 | 17.2 | 14.4 |

TABLE 1H

Ethylene selectivity for catalysts listed in Table 1F. Test conditions: 300° C. with ethane:nitrogen:oxygen flow of 0.42:0.54:0.088 sccm.

|   | 1 | 2 | 3 | 4 | 5 | 6 |
|---|---|---|---|---|---|---|
| 1 | 43.3 | | | | | |
| 2 | 81.5 | 82.8 | | | | |
| 3 | 83.1 | 81.9 | 82.5 | | | |
| 4 | 82.5 | 77.2 | 83.1 | 83.5 | | |
| 5 | 77.8 | 78.4 | 77.9 | 78.1 | 80.6 | |
| 6 | 77.8 | 76.9 | 75.4 | 78.8 | 80.1 | 73.0 |

Example 2

ODHE over NiNbTaTi Oxide Catalysts.
(#16160/16223)

Catalyst compositions comprising various relative amounts of oxides of Ni, Nb, Ta and Ti were prepared in small (~100 mg) quantities by precipitation substantially as described in connection with Example 1. Table 2A summarizes the composition and amounts of the various catalyst compositions.

In a first set of experiments, the dried catalyst compositions were calcined to 300° C. in an atmosphere of air with an oven temperature profile: ramp to 300° C. at 2° C./min and dwell at 300° C. for 8 hours. The mixed metal oxide catalysts (~50 mg) were screened in the fixed bed parallel reactor. The performance characteristics of these catalysts for ethane oxidative dehydrogenation at 300° C. with relative flowrates of ethane:nitrogen:oxygen of 0.42:0.54:0.088 sccm are summarized in Table 2B (ethane conversion) and Table 2C (ethylene selectivity). The catalysts were also screened for ethane oxidative dehydrogenation at 300° C. with relative flowrates of ethane:nitrogen:oxygen of 0.42:0.82:0.022 sccm. The performance characteristics for these experiments are summarized in Table 2D (ethane conversion) and Table 2E (ethylene selectivity).

After these screenings, these catalyst were subsequently recalcined to 400° C. for 8 hours with a similar temperature profile. The performance characteristics of these catalysts for ethane oxidative dehydrogenation in the parallel fixed bed reactor at 300° C. with relative flowrates of ethane:nitrogen:oxygen of 0.42:0.54:0.088 sccm are summarized in Table 2F (ethane conversion) and Table 2G (ethylene selectivity). The recalcined catalysts were also screened for ethane oxidative dehydrogenation at 300° C. with relative flowrates of ethane:nitrogen:oxygen of 0.42:0.82:0.022 sccm. The performance characteristics for these experiments are summarized in Table 2H (ethane conversion) and Table 2I (ethylene selectivity).

TABLE 2A

Catalyst composition (mole fraction) and sample mass, "m" (mg) of bulk NiNbTaTi Oxide Mixtures

| Row | Col | 1 | 2 | 3 | 4 | 5 | 6 |
|---|---|---|---|---|---|---|---|
| 1 | Ni | 0.6014 | 0.5714 | 0.5418 | 0.5124 | 0.4832 | 0.4542 |
|   | Nb | 0.1065 | 0.1188 | 0.1310 | 0.1431 | 0.1550 | 0.1669 |
|   | Ta | 0.0948 | 0.1133 | 0.1317 | 0.1498 | 0.1679 | 0.1857 |
|   | Ti | 0.1973 | 0.1964 | 0.1956 | 0.1948 | 0.1939 | 0.1931 |
|   | m  | 50.0 | 50.0 | 50.3 | 50.5 | 49.5 | 50.5 |
| 2 | Ni | 0.4889 | 0.4730 | 0.4559 | 0.4375 | 0.4176 | 0.3959 |
|   | Nb | 0.0808 | 0.1089 | 0.1392 | 0.1718 | 0.2071 | 0.2454 |
|   | Ta | 0.2699 | 0.2518 | 0.2323 | 0.2113 | 0.1886 | 0.1639 |
|   | Ti | 0.1604 | 0.1662 | 0.1726 | 0.1794 | 0.1868 | 0.1948 |
|   | m  | 49.5 | 50.6 | 50.0 | 50.5 | 49.6 | 49.4 |
| 3 | Ni | 0.6004 | 0.5731 | 0.5448 | 0.5154 | 0.4849 | 0.4532 |
|   | Nb | 0.1163 | 0.1279 | 0.1399 | 0.1524 | 0.1654 | 0.1788 |
|   | Ta | 0.1295 | 0.1424 | 0.1557 | 0.1696 | 0.1840 | 0.1990 |
|   | Ti | 0.1538 | 0.1566 | 0.1595 | 0.1626 | 0.1657 | 0.1689 |
|   | m  | 49.9 | 49.3 | 49.5 | 49.6 | 49.7 | 50.0 |
| 4 | Ni | 0.6435 | 0.6135 | 0.5835 | 0.5535 | 0.5234 | 0.4934 |
|   | Nb | 0.1173 | 0.1315 | 0.1457 | 0.1598 | 0.1740 | 0.1882 |
|   | Ta | 0.1306 | 0.1463 | 0.1621 | 0.1779 | 0.1937 | 0.2095 |
|   | Ti | 0.1086 | 0.1087 | 0.1087 | 0.1088 | 0.1089 | 0.1089 |
|   | m  | 49.5 | 49.3 | 49.6 | 49.5 | 50.1 | 50.3 |

TABLE 2B

Ethane conversion for the catalysts in Table 2A. Test conditions: 300° C. with ethane/nitrogen/oxygen flow of 0.42/0.54/0.088 sccm.

Ethane Conversion (%) of Ni-Nb-Ta-Ti Oxide Mixtures

|   | 1 | 2 | 3 | 4 | 5 | 6 |
|---|---|---|---|---|---|---|
| 1 | 10.7 | 17.0 | 18.1 | 19.4 | 19.2 | 13.6 |
| 2 | 9.0  | 17.5 | 18.7 | 16.8 | 19.0 | 15.6 |
| 3 | 12.1 | 17.5 | 19.0 | 19.0 | 19.1 | 16.8 |
| 4 | 7.8  | 16.8 | 19.5 | 18.8 | 17.7 | 18.2 |

TABLE 2C

Ethylene selectivity for the catalysts in Table 2A. Test conditions: 300° C. with ethane/nitrogen/oxygen flow of 0.42/0.54/0.088 sccm.

Ethylene Selectivity (%) of Ni-Nb-Ta-Ti Oxide Mixtures

|   | 1 | 2 | 3 | 4 | 5 | 6 |
|---|---|---|---|---|---|---|
| 1 | 82.9 | 83.1 | 84.3 | 85.1 | 84.2 | 83.2 |
| 2 | 80.4 | 86.6 | 85.1 | 84.7 | 84.5 | 84.1 |
| 3 | 70.9 | 84.4 | 84.9 | 84.7 | 84.6 | 84.0 |
| 4 | 76.9 | 84.7 | 84.8 | 84.5 | 84.8 | 85.0 |

TABLE 2D

Ethane conversion for the catalysts in Table 2A. Test conditions: 300° C. with ethane/nitrogen/oxygen flow of 0.42/0.082/0.022 sccm.

Ethane Conversion (%) of Ni-Nb-Ta-Ti Oxide Mixtures

|   | 1 | 2 | 3 | 4 | 5 | 6 |
|---|---|---|---|---|---|---|
| 1 | 10.5 | 11.2 | 11.4 | 11.9 | 11.8 | 11.0 |
| 2 | 8.2  | 11.4 | 11.8 | 11.3 | 11.9 | 11.5 |
| 3 | 9.3  | 11.6 | 11.3 | 11.6 | 11.8 | 11.3 |
| 4 | 7.1  | 11.6 | 12.0 | 11.6 | 11.7 | 11.4 |

TABLE 2E

Ethylene selectivity for the catalysts in Table 2A. Test conditions: 300° C. with ethane/nitrogen/oxygen flow of 0.42/0.082/0.022 sccm.

Ethylene Selectivity (%) of Ni-Nb-Ta-Ti Oxide Mixtures

|   | 1 | 2 | 3 | 4 | 5. | 6 |
|---|---|---|---|---|---|---|
| 1 | 91.6 | 92.7 | 92.9 | 93.5 | 92.9 | 92.5 |
| 2 | 90.1 | 93.4 | 93.3 | 93.4 | 93.2 | 92.6 |
| 3 | 86.7 | 93.0 | 93.5 | 93.3 | 93.3 | 92.7 |
| 4 | 87.7 | 93.4 | 93.4 | 93.0 | 93.2 | 92.9 |

TABLE 2F

Ethane conversion for the catalysts in Table 2A. Test conditions: 300° C. with ethane/nitrogen/oxygen flow of 0.42/0.54/0.088 sccm.

Ethane Conversion (%) of Ni-Nb-Ta-Ti Oxide Mixtures

|   | 1 | 2 | 3 | 4 | 5 | 6 |
|---|---|---|---|---|---|---|
| 1 | 5.6 | 12.3 | 13.2 | 14.1 | 14.6 | 7.1 |
| 2 | 4.9 | 14.7 | 13.5 | 11.4 | 15.0 | 8.7 |
| 3 | 8.1 | 12.6 | 13.3 | 14.6 | 14.6 | 11.1 |
| 4 | 3.7 | 10.4 | 14.3 | 14.8 | 14.8 | 14.4 |

TABLE 2G

Ethylene selectivity for the catalysts in Table 2A. Test conditions: 300° C. with ethane/nitrogen/oxygen flow of 0.42/0.54/0.088 sccm.

Ethylene Selectivity (%) of Ni-Nb-Ta-Ti Oxide Mixtures

|   | 1 | 2 | 3 | 4 | 5 | 6 |
|---|---|---|---|---|---|---|
| 1 | 83.4 | 80.9 | 82.1 | 84.1 | 83.8 | 84.9 |
| 2 | 81.6 | 83.9 | 84.3 | 84.5 | 83.6 | 85.1 |
| 3 | 67.9 | 83.5 | 83.7 | 83.6 | 83.6 | 84.5 |
| 4 | 78.5 | 84.7 | 83.8 | 83.2 | 83.6 | 84.5 |

TABLE 2H

Ethane conversion for the catalysts in Table 2A. Test conditions: 300° C. with ethane/nitrogen/oxygen flow of 0.42/0.082/0.022 sccm.

Ethane Conversion (%) of Ni-Nb-Ta-Ti Oxide Mixtures

|   | 1 | 2 | 3 | 4 | 5. | 6 |
|---|---|---|---|---|---|---|
| 1 | 5.7 | 10.7 | 8.4 | 11.5 | 11.9 | 7.6 |
| 2 | 5.3 | 10.2 | 11.1 | 10.7 | 11.7 | 8.6 |
| 3 | 8.4 | 11.3 | 11.2 | 11.5 | 11.8 | 10.6 |
| 4 | 4.1 | 10.1 | 11.7 | 11.6 | 11.3 | 11.2 |

TABLE 2I

Ethylene selectivity for the catalysts in Table 2A. Test conditions: 300° C. with ethane/nitrogen/oxygen flow of 0.42/0.082/0.022 sccm.

Ethylene Selectivity (%) of Ni-Nb-Ta-Ti Oxide Mixtures

|   | 1 | 2 | 3 | 4 | 5 | 6 |
|---|---|---|---|---|---|---|
| 1 | 88.9 | 92.1 | 92.4 | 93.2 | 92.8 | 90.9 |
| 2 | 87.4 | 93.2 | 93.1 | 93.0 | 93.2 | 91.7 |

TABLE 2I-continued

Ethylene selectivity for the catalysts in Table 2A. Test conditions: 300° C. with ethane/nitrogen/oxygen flow of 0.42/0.082/0.022 sccm.

Ethylene Selectivity (%) of Ni-Nb-Ta-Ti Oxide Mixtures

| | 1 | 2 | 3 | 4 | 5 | 6 |
|---|---|---|---|---|---|---|
| 3 | 85.7 | 92.5 | 93.0 | 93.2 | 93.0 | 92.3 |
| 4 | 85.5 | 92.6 | 93.1 | 92.9 | 93.1 | 92.9 |

Example 3

ODHE over NiNbZr/NiTaZr Oxide Catalysts. (#14840/15157)

Catalysts were prepared in small quantities (~100 mg) from nickel nitrate ([Ni]=1.0 M), niobium oxalate ([Nb]=0.569 M), tantalum oxalate ([Ta]=0.650 M), and zirconium oxalate ([Zr]=0.36 M) aqueous stock solutions by precipitation with tetramethylammonium hydroxide. The solid materials were separated from solution by centrifugation. The supernatant was decanted and solid materials were dried at 60° C. under a reduced atmosphere. Table 3A summarizes the composition and amounts of the various catalyst compositions.

In a first set of experiments, the dried catalyst compositions were calcined to 300° C. in an atmosphere of air with an oven temperature profile: ramp to 300° C. at 2° C./min and dwell at 300° C. for 8 hours. The mixed metal oxide catalysts (~50 mg) were screened in the fixed bed parallel reactor. The performance characteristics of these catalysts for ethane oxidative dehydrogenation at 300° C. with relative flowrates of ethane:nitrogen:oxygen of 0.42:0.54:0.088 sccm are summarized in Table 3B (ethane conversion) and Table 3C (ethylene selectivity).

After initial screening, these catalyst were subsequently recalcined to 400° C. with a similar temperature profile. The performance characteristics of these catalysts for ethane oxidative dehydrogenation in the parallel fixed bed reactor at 300° C. with relative flowrates of ethane:nitrogen:oxygen of 0.42:0.54:0.088 sccm are summarized in Table 3D (ethane conversion) and Table 3E (ethylene selectivity).

TABLE 3A

Catalyst composition (mole fraction) of Ni-Nb-Zr and Ni-Ta-Zr oxide mixtures & sample mass, "m" (mg) used in parallel fixed bed reactor screen.

| Row | Col | 1 | 2 | 3 | 4 | 5 | 6 |
|---|---|---|---|---|---|---|---|
| 1 | Ni | 1.0000 | 0.8969 | 0.7944 | 0.6927 | 0.5917 | 0.4914 |
| | Nb | 0.0000 | 0.0000 | 0.0000 | 0.0000 | 0.0000 | 0.0000 |
| | Ta | 0.0000 | 0.1031 | 0.2056 | 0.3073 | 0.4083 | 0.5086 |
| | Zr | 0.0000 | 0.0000 | 0.0000 | 0.0000 | 0.0000 | 0.0000 |
| | m | 49.8 | 49.5 | 49.6 | 49.6 | 50.1 | 49.5 |
| 2 | Ni | 0.9119 | 0.9328 | 0.8262 | 0.7203 | 0.6152 | 0.5108 |
| | Nb | 0.0881 | 0.0000 | 0.0000 | 0.0000 | 0.0000 | 0.0000 |
| | Ta | 0.0000 | 0.0000 | 0.1069 | 0.2130 | 0.3184 | 0.4230 |
| | Zr | 0.0000 | 0.0672 | 0.0669 | 0.0667 | 0.0664 | 0.0662 |
| | m | 49.3 | 4 9.6 | 50.4 | 49.9 | 50.3 | 49.3 |
| 3 | Ni | 0.8214 | 0.8405 | 0.8606 | 0.7502 | 0.6406 | 0.5319 |
| | Nb | 0.1786 | 0.0914 | 0.0000 | 0.0000 | 0.0000 | 0.0000 |
| | Ta | 0.0000 | 0.0000 | 0.0000 | 0.1109 | 0.2210 | 0.3303 |
| | Zr | 0.0000 | 0.0681 | 0.1394 | 0.1389 | 0.1384 | 0.1379 |
| | m | 49.8 | 50.6 | 50.5 | 49.5 | 50.6 | 49.9 |
| 4 | Ni | 0.7284 | 0.7456 | 0.7637 | 0.7826 | 0.6682 | 0.5547 |
| | Nb | 0.2716 | 0.1853 | 0.0949 | 0.0000 | 0.0000 | 0.0000 |
| | Ta | 0.0000 | 0.0000 | 0.0000 | 0.0000 | 0.1153 | 0.2296 |
| | Zr | 0.0000 | 0.0690 | 0.1414 | 0.2174 | 0.2165 | 0.2157 |
| | m | 50.1 | 49.4 | 49.5 | 49.6 | 49.5 | 50.6 |
| 5 | Ni | 0.6329 | 0.6481 | 0.6640 | 0.6807 | 0.6983 | 0.5796 |
| | Nb | 0.3671 | 0.2819 | 0.1926 | 0.0987 | 0.0000 | 0.0000 |
| | Ta | 0.0000 | 0.0000 | 0.0000 | 0.0000 | 0.0000 | 0.1200 |
| | Zr | 0.0000 | 0.0700 | 0.1434 | 0.2206 | 0.3017 | 0.3005 |
| | m | 50.3 | 49.6 | 49.8 | 49.5 | 49.9 | 49.7 |
| 6 | Ni | 0.5348 | 0.5478 | 0.5614 | 0.5758 | 0.5909 | 0.6068 |
| | Nb | 0.4652 | 0.3812 | 0.2931 | 0.2004 | 0.1028 | 0.0000 |
| | Ta | 0.0000 | 0.0000 | 0.0000 | 0.0000 | 0.0000 | 0.0000 |
| | Zr | 0.0000 | 0.0710 | 0.1455 | 0.2239 | 0.3063 | 0.3932 |
| | m | 50.0 | 49.8 | 50.3 | 50.6 | 50.0 | 49.9 |

TABLE 3B

Ethane conversion for the catalysts in Table 3A. Test conditions: 300° C. with ethane/nitrogen/oxygen flow of 0.42/0.54/0.088 sccm.

Ethane Conversion (%) of Ni-Nb-Ta-Zr Oxide Mixtures

| | 1 | 2 | 3 | 4 | 5 | 6 |
|---|---|---|---|---|---|---|
| 1 | 9.1 | 18.2 | 18.9 | 19.2 | 18.6 | 15.7 |
| 2 | 16.0 | 14.8 | 18.0 | 16.4 | 17.3 | 19.5 |
| 3 | 18.4 | 18.1 | 15.4 | 17.6 | 13.1 | 16.7 |
| 4 | 19.3 | 19.1 | 16.7 | 14.7 | 15.2 | 15.3 |
| 5 | 19.4 | 19.0 | 13.7 | 15.3 | 13.6 | 16.1 |
| 6 | 18.9 | 19.0 | 12.1 | 11.3 | 12.7 | 12.4 |

TABLE 3C

Ethylene Selectivity for the catalysts in Table 3A. Test conditions: 300° C. with ethane/nitrogen/oxygen flow of 0.42/0.54/0.088 sccm.

Ethylene Selectivity (%) of Ni-Nb-Ta-Zr Oxide Mixtures

| | 1 | 2 | 3 | 4 | 5 | 6 |
|---|---|---|---|---|---|---|
| 1 | 46.0 | 83.8 | 84.4 | 84.0 | 84.8 | 83.0 |
| 2 | 80.4 | 74.4 | 83.4 | 81.1 | 80.7 | 83.6 |
| 3 | 84.8 | 83.7 | 77.2 | 81.8 | 73.9 | 81.5 |
| 4 | 84.4 | 84.2 | 79.5 | 76.6 | 73.6 | 79.1 |
| 5 | 84.7 | 82.9 | 73.4 | 76.6 | 73.4 | 79.3 |
| 6 | 82.7 | 84.6 | 73.9 | 70.2 | 73.9 | 76.5 |

TABLE 3D

Ethane Conversion for the catalysts in Table 3A but recalcined to 400° C. Test conditions: 300° C. with ethane/nitrogen/oxygen flow of 0.42/0.54/0.088 sccm.
Ethane Conversion (%) of Ni—Nb—Ta—Zr Oxide Mixtures

| | 1 | 2 | 3 | 4 | 5 | 6 |
|---|---|---|---|---|---|---|
| 1 | 6.3 | 12.2 | 12.6 | 12.5 | 11.9 | 8.9 |
| 2 | 9.1 | 10.8 | 12.2 | 10.8 | 11.4 | 15.1 |
| 3 | 12.2 | 13.8 | 10.2 | 11.9 | 8.0 | 11.2 |
| 4 | 13.2 | 13.2 | 11.4 | 8.8 | 10.3 | 10.8 |
| 5 | 13.6 | 13.5 | 8.6 | 11.2 | 9.2 | 12.2 |
| 6 | 14.7 | 13.4 | 7.5 | 6.4 | 8.0 | 7.5 |

TABLE 3E

Ethylene Selectivity for the catalysts in Table 3A but recalcined to 400° C. Test conditions: 300° C. with ethane/nitrogen/oxygen flow of 0.42/0.54/0.088 sccm.
Ethylene Selectivity (%) of Ni—Nb—Ta—Zr Oxide Mixtures

|   | 1 | 2 | 3 | 4 | 5 | 6 |
|---|---|---|---|---|---|---|
| 1 | 33.4 | 83.3 | 85.4 | 84.6 | 86.0 | 86.7 |
| 2 | 78.8 | 66.2 | 83.3 | 81.0 | 80.9 | 83.5 |
| 3 | 86.4 | 84.1 | 70.6 | 80.2 | 72.9 | 81.1 |
| 4 | 85.8 | 84.8 | 78.6 | 69.1 | 69.3 | 78.5 |
| 5 | 86.5 | 83.7 | 71.9 | 75.8 | 69.7 | 77.0 |
| 6 | 80.4 | 82.9 | 72.3 | 62.9 | 71.7 | 74.9 |

Example 4

ODHE over NiTiZr Oxide Catalysts. (#14332)

Catalysts were prepared in small quantities (~100 mg) from nickel nitrate ([Ni]=1.0 M), titanium oxalate ([Ti]=0.713 M) and zirconium oxalate ([Zr]=0.36 M) aqueous stock solutions by precipitation with tetramethylammonium hydroxide. The solid materials were separated from solution by centrifugation. The supernatant was decanted and solid materials were dried at 60° C. under a reduced atmosphere. Table 4A summarizes the composition and amounts of the various catalyst compositions.

In a first set of experiments, the dried catalyst compositions were calcined to 300° C. in an atmosphere of air with an oven temperature profile: ramp to 300° C. at 2° C./min and dwell at 300° C. for 8 hours. The mixed metal oxide catalysts (~50 mg) were screened in the fixed bed parallel reactor. The performance characteristics of these catalysts for ethane oxidative dehydrogenation at 300° C. with relative flowrates of ethane:nitrogen:oxygen of 0.42:0.54:0.088 sccm are summarized in Table 4B (ethane conversion) and Table 4C (ethylene selectivity).

TABLE 4A

Catalyst composition (mole fraction) of NiTiZr oxide catalysts and sample mass (mg) used in parallel fixed bed reactor screen.

| Row | | Column | | | | | |
|---|---|---|---|---|---|---|---|
| | | 1 | 2 | 3 | 4 | 5 | 6 |
| 1 | Ni | 1.000 | | | | | |
| | Zr | 0.000 | | | | | |
| | Ti | 0.000 | | | | | |
| | mass (mg) | 54.1 | | | | | |
| 2 | Ni | 0.930 | 0.913 | | | | |
| | Zr | 0.070 | 0.000 | | | | |
| | Ti | 0.000 | 0.087 | | | | |
| | mass (mg) | 52.3 | 47.6 | | | | |
| 3 | Ni | 0.862 | 0.847 | 0.833 | | | |
| | Zr | 0.138 | 0.068 | 0.000 | | | |
| | Ti | 0.000 | 0.085 | 0.167 | | | |
| | mass (mg) | 54.8 | 50.3 | 52.3 | | | |
| 4 | Ni | 0.797 | 0.784 | 0.771 | 0.759 | | |
| | Zr | 0.203 | 0.133 | 0.065 | 0.000 | | |
| | Ti | 0.000 | 0.083 | 0.163 | 0.241 | | |
| | mass (mg) | 52.0 | 54.0 | 47.4 | 50.2 | | |
| 5 | Ni | 0.735 | 0.723 | 0.712 | 0.701 | 0.690 | |
| | Zr | 0.265 | 0.195 | 0.128 | 0.063 | 0.000 | |
| | Ti | 0.000 | 0.081 | 0.160 | 0.236 | 0.310 | |

TABLE 4A-continued

Catalyst composition (mole fraction) of NiTiZr oxide catalysts and sample mass (mg) used in parallel fixed bed reactor screen.

| | | Column | | | | | |
|---|---|---|---|---|---|---|---|
| Row | | 1 | 2 | 3 | 4 | 5 | 6 |
| | mass (mg) | 52.0 | 52.9 | 45.3 | 46.4 | 49.6 | |
| 6 | Ni | 0.676 | 0.665 | 0.654 | 0.644 | 0.635 | 0.625 |
| | Zr | 0.324 | 0.255 | 0.188 | 0.124 | 0.061 | 0.000 |
| | Ti | 0.000 | 0.080 | 0.157 | 0.232 | 0.305 | 0.375 |
| | mass (mg) | 53.0 | 45.2 | 50.6 | 47.3 | 51.8 | 52.5 |

TABLE 4B

Ethane conversion for catalysts in Table 4A. Test conditions: 300° C. with ethane:nitrogen:oxygen flow of 0.42:0.54:0.088 sccm.

|   | 1 | 2 | 3 | 4 | 5 | 6 |
|---|---|---|---|---|---|---|
| 1 | 7.9 | | | | | |
| 2 | 15.5 | 14.9 | | | | |
| 3 | 17.0 | 16.5 | 16.6 | | | |
| 4 | 13.3 | 14.3 | 17.2 | 17.3 | | |
| 5 | 14.2 | 15.4 | 15.8 | 17.7 | 20.6 | |
| 6 | 12.4 | 14.9 | 13.0 | 13.5 | 16.1 | 19.1 |

TABLE 4C

Ethylene selectivity for catalysts in Table 4A. Test conditions: 300° C. with ethane:nitrogen:oxygen flow of 0.42:0.54:0.088 sccm.

|   | 1 | 2 | 3 | 4 | 5 | 6 |
|---|---|---|---|---|---|---|
| 1 | 46.1 | | | | | |
| 2 | 72.9 | 78.5 | | | | |
| 3 | 75.8 | 76.5 | 81.9 | | | |
| 4 | 71.3 | 78.8 | 81.0 | 81.7 | | |
| 5 | 71.0 | 74.8 | 72.1 | 81.2 | 84.7 | |
| 6 | 69.0 | 71.3 | 76.8 | 70.9 | 77.7 | 83.2 |

Example 5

ODHE over NiTiCe/NiZrCe Oxide Catalysts. (#14841/15158)

Ni—Ti—Ce and Ni—Zr—Ce oxide catalysts were prepared and screened in a manner similar to the catalysts in Examples 1 and 3, using cerium nitrate ([Ce]=1.00 M) aqueous stock solution. Table 5A summarizes the composition and amounts of the various catalyst compositions.

In the initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiTiCe oxide compositions ranged from 9.6% (with ethylene selectivity of 66.5%) to 17.6% (with ethylene selectivity of 79.3%), and ethylene selectivity values ranged from 66.5% (with ethane conversion of 9.6%) to 80.1% (with ethane conversion of 17.0%). Ethane conversion values for the NiZrCe oxide compositions ranged from 13.4% (with ethylene selectivity of 69.1%) to 16.4% (with ethylene selectivity of 75.9%), and ethylene selectivity values ranged from 69.1% (with ethane conversion of 13.4%) to 78.2% (with ethane conversion of 15.4%).

After recalcining (400° C., 8 hours, as described), the catalysts were rescreened (results not shown).

TABLE 5A

Catalyst composition (mole fraction) of Ni—Ti—Ce and Ni—Zr—Ce oxide catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 1.0000 | 0.9259 | 0.8475 | 0.7642 | 0.6757 | 0.5814 |
|   | Ti | 0.0000 | 0.0000 | 0.0000 | 0.0000 | 0.0000 | 0.0000 |
|   | Ce | 0.0000 | 0.0000 | 0.0000 | 0.0000 | 0.0000 | 0.0000 |
|   | Zr | 0.0000 | 0.0741 | 0.1525 | 0.2358 | 0.3243 | 0.4186 |
|   | m  | 49.5 | 49.4 | 49.7 | 48.6 | 49.2 | 49.8 |
| 2 | Ni | 0.9091 | 0.9474 | 0.8677 | 0.7830 | 0.6928 | 0.5967 |
|   | Ti | 0.0909 | 0.0000 | 0.0000 | 0.0000 | 0.0000 | 0.0000 |
|   | Ce | 0.0000 | 0.0526 | 0.0542 | 0.0559 | 0.0577 | 0.0597 |
|   | Zr | 0.0000 | 0.0000 | 0.0781 | 0.1611 | 0.2494 | 0.3437 |
|   | m  | 50.6 | 50.7 | 49.5 | 50.0 | 49.7 | 50.6 |
| 3 | Ni | 0.8163 | 0.8511 | 0.8889 | 0.8028 | 0.7109 | 0.6127 |
|   | Ti | 0.1837 | 0.0957 | 0.0000 | 0.0000 | 0.0000 | 0.0000 |
|   | Ce | 0.0000 | 0.0532 | 0.1111 | 0.1147 | 0.1185 | 0.1225 |
|   | Zr | 0.0000 | 0.0000 | 0.0000 | 0.0826 | 0.1706 | 0.2647 |
|   | m  | 49.4 | 49.7 | 50.5 | 49.7 | 49.4 | 50.3 |
| 4 | Ni | 0.7216 | 0.7527 | 0.7865 | 0.8235 | 0.7299 | 0.6297 |
|   | Ti | 0.2784 | 0.1935 | 0.1011 | 0.0000 | 0.0000 | 0.0000 |
|   | Ce | 0.0000 | 0.0538 | 0.1124 | 0.1765 | 0.1825 | 0.1889 |
|   | Zr | 0.0000 | 0.0000 | 0.0000 | 0.0000 | 0.0876 | 0.1814 |
|   | m  | 49.9 | 50.6 | 50.4 | 49.3 | 50.0 | 50.0 |
| 5 | Ni | 0.6250 | 0.6522 | 0.6818 | 0.7143 | 0.7500 | 0.6477 |
|   | Ti | 0.3750 | 0.2935 | 0.2045 | 0.1071 | 0.0000 | 0.0000 |
|   | Ce | 0.0000 | 0.0543 | 0.1136 | 0.1786 | 0.2500 | 0.2591 |
|   | Zr | 0.0000 | 0.0000 | 0.0000 | 0.0000 | 0.0000 | 0.0933 |
|   | m  | 49.7 | 49.6 | 49.9 | 50.6 | 50.1 | 50.4 |
| 6 | Ni | 0.5263 | 0.5495 | 0.5747 | 0.6024 | 0.6329 | 0.6667 |
|   | Ti | 0.4737 | 0.3956 | 0.3103 | 0.2169 | 0.1139 | 0.0000 |
|   | Ce | 0.0000 | 0.0549 | 0.1149 | 0.1807 | 0.2532 | 0.3333 |
|   | Zr | 0.0000 | 0.0000 | 0.0000 | 0.0000 | 0.0000 | 0.0000 |
|   | m  | 50.0 | 49.6 | 49.9 | 50.0 | 50.1 | 50.4 |

TABLE 6A

Catalyst composition (mole fraction) of NiTiSb/NiZrSb oxide mixtures and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 1.0000 | 0.9377 | 0.8642 | 0.7764 | 0.6695 | 0.5365 |
|   | Ti | 0.0000 | 0.0000 | 0.0000 | 0.0000 | 0.0000 | 0.0000 |
|   | Zr | 0.0000 | 0.0623 | 0.1358 | 0.2236 | 0.3305 | 0.4635 |
|   | Sb | 0.0000 | 0.0000 | 0.0000 | 0.0000 | 0.0000 | 0.0000 |
|   | m  | 49.4 | 50.6 | 50.4 | 50.6 | 49.3 | 49.5 |
| 2 | Ni | 0.9233 | 0.9403 | 0.8669 | 0.7790 | 0.6719 | 0.5387 |
|   | Ti | 0.0767 | 0.0000 | 0.0000 | 0.0000 | 0.0000 | 0.0000 |
|   | Zr | 0.0000 | 0.0000 | 0.0681 | 0.1496 | 0.2488 | 0.3724 |
|   | Sb | 0.0000 | 0.0597 | 0.0651 | 0.0715 | 0.0793 | 0.0890 |
|   | m  | 50.4 | 50.7 | 50.0 | 49.4 | 50.0 | 50.2 |
| 3 | Ni | 0.8359 | 0.8523 | 0.8695 | 0.7816 | 0.6744 | 0.5409 |
|   | Ti | 0.1641 | 0.0837 | 0.0000 | 0.0000 | 0.0000 | 0.0000 |
|   | Zr | 0.0000 | 0.0000 | 0.0000 | 0.0750 | 0.1665 | 0.2804 |
|   | Sb | 0.0000 | 0.0640 | 0.1305 | 0.1434 | 0.1591 | 0.1786 |
|   | m  | 50.4 | 50.4 | 49.2 | 50.3 | 49.4 | 49.7 |
| 4 | Ni | 0.7353 | 0.7509 | 0.7672 | 0.7842 | 0.6769 | 0.5432 |
|   | Ti | 0.2647 | 0.1802 | 0.0921 | 0.0000 | 0.0000 | 0.0000 |
|   | Zr | 0.0000 | 0.0000 | 0.0000 | 0.0000 | 0.0836 | 0.1877 |
|   | Sb | 0.0000 | 0.0689 | 0.1408 | 0.2158 | 0.2395 | 0.2691 |
|   | m  | 49.2 | 49.3 | 49.8 | 50.7 | 50.6 | 49.8 |
| 5 | Ni | 0.6184 | 0.6326 | 0.6475 | 0.6631 | 0.6795 | 0.5455 |
|   | Ti | 0.3816 | 0.2928 | 0.1998 | 0.1023 | 0.0000 | 0.0000 |
|   | Zr | 0.0000 | 0.0000 | 0.0000 | 0.0000 | 0.0000 | 0.0943 |
|   | Sb | 0.0000 | 0.0746 | 0.1527 | 0.2346 | 0.3205 | 0.3603 |
|   | m  | 50.8 | 49.5 | 49.3 | 50.0 | 50.2 | 49.7 |
| 6 | Ni | 0.4808 | 0.4928 | 0.5055 | 0.5188 | 0.5329 | 0.5478 |
|   | Ti | 0.5192 | 0.4258 | 0.3276 | 0.2241 | 0.1151 | 0.0000 |
|   | Zr | 0.0000 | 0.0000 | 0.0000 | 0.0000 | 0.0000 | 0.0000 |
|   | Sb | 0.0000 | 0.0814 | 0.1669 | 0.2570 | 0.3520 | 0.4522 |
|   | m  | 20.2 | 50.6 | 50.5 | 50.8 | 50.4 | 49.0 |

Example 6

ODHE over NiTiSb/NiZrSb Oxide Catalysts.
(#14842/15159)

Ni—Ti—Sb and Ni—Zr—Sb oxide catalysts were prepared and screened in a manner similar to the catalysts in Examples 1 and 3, using antimony acetate ([Sb]=0.234 M) aqueous stock solution. Table 6A summarizes the composition and amounts of the various catalyst compositions.

In the initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiTiSb oxide compositions ranged from 1.0% (with ethylene selectivity of 73.3%) to 15.8% (with ethylene selectivity of 79.2%), and ethylene selectivity values ranged from 73.3% (with ethane conversion of 1.0%) to 81.8% (with ethane conversion of 7.2%). Ethane conversion values for the NiZrSb oxide compositions ranged from 1.4% (with ethylene selectivity of 75.5%) to 11.9% (with ethylene selectivity of 74.7%), and ethylene selectivity values ranged from 63.2% (with ethane conversion of 6.3%) to 78.3% (with ethane conversion of 11.3%).

After recalcining (400° C., 8 hours, as described), the catalysts were rescreened (results not shown).

Example 7

ODHE over NiTiNd/NiZrNd Oxide Catalysts.
(#15154/15420)

Ni—Ti—Nd and Ni—Zr—Nd oxide catalysts were prepared and screened in a manner similar to the catalysts in Examples 1 and 3, using neodymium nitrate ([Nd]=0.50 M) aqueous stock solution. Table 7A summarizes the composition and amounts of the various catalyst compositions.

In the initial screening (calcination at 300° C., 8 hours, screening in fixed bed parallel reactor at 300° C. with flowrates of ethane:nitrogen:oxygen of 0.42:0.54:0.088 sccm, as described), ethane conversion (C) and ethylene selectivity (S) values for the NiTiNd oxide compositions ranged from 6.3% C, 45.1% S to 18.1% C, 84.6% S. Ethane conversion values for the NiZrNd oxide compositions ranged from 4.5% (with ethylene selectivity of 41.5%) to 13.4% (with ethylene selectivity of 71.8%), and ethylene selectivity values ranged from 41.5% (with ethane conversion of 4.5%) to 77.3% (with ethane conversion of 13.1%).

In a second screening in the fixed bed parallel reactor at 300° C. with different flowrates (ethanc:nitrogen:oxygen of 0.42:0.082:0.022 sccm), ethane conversion (C) and ethylene selectivity (S) values for the NiTiNd oxide compositions ranged from 4.9% C, 62.7% S to 11.0% C, 93.3% S. Ethane conversion (C) and ethylene selectivity (S) values for the NiZrNd oxide compositions ranged from 4.2% C, 59.0% S to 10.0% C, 90.7% S.

After recalcining (400° C., S hours, as described), the catalysts were rescreened (results not shown).

TABLE 7A

Catalyst composition (mole fraction) of NiTiNd/NiZrNd oxide catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 1.0000 | 0.9259 | 0.8475 | 0.7642 | 0.6757 | 0.5814 |
|   | Ti | 0.0000 | 0.0000 | 0.0000 | 0.0000 | 0.0000 | 0.0000 |
|   | Zr | 0.0000 | 0.0741 | 0.1525 | 0.2358 | 0.3243 | 0.4186 |
|   | Nd | 0.0000 | 0.0000 | 0.0000 | 0.0000 | 0.0000 | 0.0000 |
|   | m  | 49.6 | 49.7 | 49.5 | 49.3 | 50.3 | 495 |
| 2 | Ni | 0.9259 | 0.9474 | 0.8677 | 0.7830 | 0.6928 | 0.5967 |
|   | Ti | 0.0741 | 0.0000 | 0.0000 | 0.0000 | 0.0000 | 0.0000 |
|   | Zr | 0.0000 | 0.0000 | 0.0781 | 0.1611 | 0.2494 | 0.3437 |
|   | Nd | 0.0000 | 0.0526 | 0.0542 | 0.0559 | 0.0577 | 0.0597 |
|   | m  | 49.9 | 50.8 | 50.4 | 49.4 | 49.4 | 50.0 |
| 3 | Ni | 0.8475 | 0.8677 | 0.8889 | 0.8028 | 0.7109 | 0.6127 |
|   | Ti | 0.1525 | 0.0781 | 0.0000 | 0.0000 | 0.0000 | 0.0000 |
|   | Zr | 0.0000 | 0.0000 | 0.0000 | 0.0826 | 0.1706 | 0.2647 |
|   | Nd | 0.0000 | 0.0542 | 0.1111 | 0.1147 | 0.1185 | 0.1225 |
|   | m  | 49.9 | 49.2 | 49.4 | 50.3 | 49.7 | 49.4 |
| 4 | Ni | 0.7642 | 0.7830 | 0.8028 | 0.8235 | 0.7299 | 0.6297 |
|   | Ti | 0.2358 | 0.1611 | 0.0826 | 0.0000 | 0.0000 | 0.0000 |
|   | Zr | 0.0000 | 0.0000 | 0.0000 | 0.0000 | 0.0876 | 0.1814 |
|   | Nd | 0.0000 | 0.0559 | 0.1147 | 0.1765 | 0.1825 | 0.1889 |
|   | m  | 49.8 | 49.5 | 50.0 | 49.8 | 49.8 | 49.8 |
| 5 | Ni | 0.6757 | 0.6928 | 0.7109 | 0.7299 | 0.7500 | 0.6477 |
|   | Ti | 0.3243 | 0.2494 | 0.1706 | 0.0876 | 0.0000 | 0.0000 |
|   | Zr | 0.0000 | 0.0000 | 0.0000 | 0.0000 | 0.0000 | 0.0933 |
|   | Nd | 0.0000 | 0.0577 | 0.1185 | 0.1825 | 0.2500 | 0.2591 |
|   | m  | 49.5 | 49.6 | 49.8 | 50.0 | 49.4 | 50.1 |
| 6 | Ni | 0.5814 | 0.5967 | 0.6127 | 0.6297 | 0.6477 | 0.6667 |
|   | Ti | 0.4186 | 0.3437 | 0.2647 | 0.1814 | 0.0933 | 0.0000 |
|   | Zr | 0.0000 | 0.0000 | 0.0000 | 0.0000 | 0.0000 | 0.0000 |
|   | Nd | 0.0000 | 0.0597 | 0.1225 | 0.1889 | 0.2591 | 0.3333 |
|   | m  | 50.1 | 49.3 | 49.5 | 50.7 | 50.6 | 45.0 |

TABLE 8A

Catalyst composition (mole fraction) of NiTiYb/NiZrYb oxide catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 1.0000 | 0.9259 | 0.8475 | 0.7642 | 0.6757 | 0.5814 |
|   | Ti | 0.0000 | 0.0000 | 0.0000 | 0.0000 | 0.0000 | 0.0000 |
|   | Zr | 0.0000 | 0.0741 | 0.1525 | 0.2358 | 0.3243 | 0.4186 |
|   | Yb | 0.0000 | 0.0000 | 0.0000 | 0.0000 | 0.0000 | 0.0000 |
|   | m  | 50.0 | — | — | — | — | — |
| 2 | Ni | 0.9091 | 0.9518 | 0.8718 | 0.7869 | 0.6964 | 0.5998 |
|   | Ti | 0.0909 | 0.0000 | 0.0000 | 0.0000 | 0.0000 | 0.0000 |
|   | Zr | 0.0000 | 0.0000 | 0.0785 | 0.1619 | 0.2507 | 0.3455 |
|   | Yb | 0.0000 | 0.0482 | 0.0497 | 0.0513 | 0.0529 | 0.0547 |
|   | m  | 49.3 | 49.6 | 50.1 | 50.0 | 49.4 | 50.3 |
| 3 | Ni | 0.8163 | 0.8551 | 0.8977 | 0.8109 | 0.7184 | 0.6194 |
|   | Ti | 0.1837 | 0.0962 | 0.0000 | 0.0000 | 0.0000 | 0.0000 |
|   | Zr | 0.0000 | 0.0000 | 0.0000 | 0.0834 | 0.1724 | 0.2676 |
|   | Yb | 0.0000 | 0.0487 | 0.1023 | 0.1057 | 0.1092 | 0.1130 |
|   | m  | 49.7 | 49.3 | 49.8 | 50.0 | 49.5 | 49.1 |
| 4 | Ni | 0.7216 | 0.7563 | 0.7944 | 0.8365 | 0.7418 | 0.6404 |
|   | Ti | 0.2784 | 0.1945 | 0.1021 | 0.0000 | 0.0000 | 0.0000 |
|   | Zr | 0.0000 | 0.0000 | 0.0000 | 0.0000 | 0.0890 | 0.1844 |
|   | Yb | 0.0000 | 0.0493 | 0.1035 | 0.1635 | 0.1691 | 0.1752 |
|   | m  | 49.5 | 50.3 | 49.3 | 49.8 | 50.2 | 50.6 |
| 5 | Ni | 0.6250 | 0.6553 | 0.6887 | 0.7257 | 0.7669 | 0.6628 |
|   | Ti | 0.3750 | 0.2949 | 0.2066 | 0.1089 | 0.0000 | 0.0000 |
|   | Zr | 0.0000 | 0.0000 | 0.0000 | 0.0000 | 0.0000 | 0.0954 |
|   | Yb | 0.0000 | 0.0498 | 0.1047 | 0.1655 | 0.2331 | 0.2418 |
|   | m  | 49.3 | 49.9 | 50.0 | 49.5 | 50.6 | 49.8 |
| 6 | Ni | 0.5263 | 0.5521 | 0.5806 | 0.6121 | 0.6473 | 0.6868 |
|   | Ti | 0.4737 | 0.3975 | 0.3135 | 0.2204 | 0.1165 | 0.0000 |
|   | Zr | 0.0000 | 0.0000 | 0.0000 | 0.0000 | 0.0000 | 0.0000 |
|   | Yb | 0.0000 | 0.0504 | 0.1059 | 0.1675 | 0.2361 | 0.3132 |
|   | m  | 49.4 | 49.6 | 50.3 | 49.6 | 50.5 | 49.8 |

Example 8

ODHE over NiTiYb/NiZrYb Oxide Catalysts.
(#15155/15421)

Ni—Ti—Yb and Ni—Zr—Yb oxide catalysts were prepared and screened in a manner similar to the catalysts in Examples 1 and 3, using ytterbium nitrate ([Yb]=0.456 M) aqueous stock solution. Table 8A summarizes the composition and amounts of the various catalyst compositions.

In the initial screening (calcination at 300° C., 8 hours, screening in fixed bed parallel reactor at 300° C. with flowrates of ethane:nitrogen:oxygen of 0.42:0.54:0.088 sccm, as described), ethane conversion (C) and ethylene selectivity (S) values for the NiTiYb oxide compositions ranged from 4.1% C, 41.6% S to 16.8% C, 83.4% S. Ethane conversion (C) and ethylene selectivity (S) values for the NiZrYb oxide compositions ranged from 5.0% C, 46.8% S to 13.2% C, 75.6% S.

In a second screening in the fixed bed parallel reactor at 300° C. with different flowrates (ethane:nitrogen:oxygen of 0.42:0.082:0.022 sccm), ethane conversion (C) and ethylene selectivity (S) values for the NiTiYb oxide compositions ranged from 6.0% C, 72.9% S to 10.6% C, 91.8% S. Ethane conversion (C) and ethylene selectivity (S) values for the NiZrYb oxide compositions ranged from 6.7% C, 75.9% S to 10.3% C, 89.9% S.

After recalcining (400° C., 8 hours, as described), the catalysts were rescreened (results not shown).

Example 9

ODHE over NiTiSm/NiZrSm Oxide Catalysts.
(#1.5935/16221)

Ni—Ti—Sm and Ni—Zr—Sm oxide catalysts were prepared and screened in a manner similar to the catalysts in Examples 1 and 3, using samarium nitrate ([Sm]=0.506 M) aqueous stock solution. Table 9A summarizes the composition and amounts of the various catalyst compositions.

In the initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiTiSm oxide compositions ranged from 10.4% (with ethylene selectivity of 57.5%) to 19.0% (with ethylene selectivity of 81.8%), and ethylene selectivity values ranged from 57.5% (with ethane conversion of 10.4%) to 82.8% (with ethane conversion of 18.3%). Ethane conversion values for the NiZrSm oxide compositions ranged from 11.5% (with ethylene selectivity of 60.7%) to 13.7% (with ethylene selectivity of 71.0%), and ethylene selectivity values ranged from 60.7% (with ethane conversion of 11.5%) to 76.7% (with ethane conversion of 13.4%).

In a second screening in the fixed bed parallel reactor at 300° C. with different flowrates (ethane:nitrogen:oxygen of 0.42:0.082:0.022 sccm), ethane conversion values for the NiTiSm oxide compositions ranged from 6.8% (with ethylene selectivity of 75.1%) to 11.5% (with ethylene selectivity of 92.2%), and ethylene selectivity values ranged from 75.1% (with ethane conversion of 6.8%) to 92.7% (with ethane conversion of 11.3%). Ethane conversion (C) and ethylene selectivity (S) values for the NiZrSm oxide compositions ranged from 7.7% C, 80.3% S to 10.3% C, 90.4% S.

After recalcining (400° C., 8 hours, as described), the catalysts were rescreened (results not shown).

TABLE 9A

Catalyst composition (mole fraction) of NiTiSm/NiZrSm oxide catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 1.0000 | 0.9259 | 0.8475 | 0.7642 | 0.6757 | 0.5814 |
|   | Ti | 0.0000 | 0.0000 | 0.0000 | 0.0000 | 0.0000 | 0.0000 |
|   | Zr | 0.0000 | 0.0741 | 0.1525 | 0.2358 | 0.3243 | 0.4186 |
|   | Sm | 0.0000 | 0.0000 | 0.0000 | 0.0000 | 0.0000 | 0.0000 |
|   | m  | 49.6   | 49.8   | 50.0   | 50.5   | 50.3   | 50.0   |
| 2 | Ni | 0.9091 | 0.9730 | 0.8919 | 0.8055 | 0.7134 | 0.6150 |
|   | Ti | 0.0909 | 0.0000 | 0.0000 | 0.0000 | 0.0000 | 0.0000 |
|   | Zr | 0.0000 | 0.0000 | 0.0803 | 0.1657 | 0.2568 | 0.3542 |
|   | Sm | 0.0000 | 0.0270 | 0.0279 | 0.0288 | 0.0297 | 0.0308 |
|   | m  | 49.8   | 50.8   | 49.5   | 49.7   | 50.3   | 49.7   |
| 3 | Ni | 0.8163 | 0.8743 | 0.9412 | 0.8516 | 0.7557 | 0.6527 |
|   | Ti | 0.1837 | 0.0984 | 0.0000 | 0.0000 | 0.0000 | 0.0000 |
|   | Zr | 0.0000 | 0.0000 | 0.0000 | 0.0876 | 0.1814 | 0.2820 |
|   | Sm | 0.0000 | 0.0273 | 0.0588 | 0.0608 | 0.0630 | 0.0653 |
|   | m  | 49.5   | 50.4   | 49.7   | 50.1   | 50.3   | 49.9   |
| 4 | Ni | 0.7216 | 0.7735 | 0.8333 | 0.9032 | 0.8032 | 0.6954 |
|   | Ti | 0.2784 | 0.1989 | 0.1071 | 0.0000 | 0.0000 | 0.0000 |
|   | Zr | 0.0000 | 0.0000 | 0.0000 | 0.0000 | 0.0964 | 0.2003 |
|   | Sm | 0.0000 | 0.0276 | 0.0595 | 0.0968 | 0.1004 | 0.1043 |
|   | m  | 49.5   | 49.5   | 50.7   | —      | 49.5   | 50.7   |
| 5 | Ni | 0.6250 | 0.6704 | 0.7229 | 0.7843 | 0.8571 | 0.7440 |
|   | Ti | 0.3750 | 0.3017 | 0.2169 | 0.1176 | 0.0000 | 0.0000 |
|   | Zr | 0.0000 | 0.0000 | 0.0000 | 0.0000 | 0.0000 | 0.1071 |
|   | Sm | 0.0000 | 0.0279 | 0.0602 | 0.0980 | 0.1429 | 0.1488 |
|   | m  | 50.6   | 49.6   | 49.8   | 48.6   | 50.7   | 48.8   |
| 6 | Ni | 0.5263 | 0.5650 | 0.6098 | 0.6623 | 0.7246 | 0.8000 |
|   | Ti | 0.4737 | 0.4068 | 0.3293 | 0.2384 | 0.1304 | 0.0000 |
|   | Zr | 0.0000 | 0.0000 | 0.0000 | 0.0000 | 0.0000 | 0.0000 |
|   | Sm | 0.0000 | 0.0282 | 0.0610 | 0.0993 | 0.1449 | 0.2000 |
|   | m  | 50.4   | 49.5   | 50.4   | 51.0   | 49.9   | 49.3   |

Example 10

ODHE over NiTiSmX (X=Cs, Mg, Ca, Sb, Bi, V, Nb, Ta) and NiTiNbTaSm Oxide Catalysts (#16297/16506/16650)

Catalyst compositions comprising various NiTiSmX oxides, where X is Cs, Mg, Ca, Sb, Bi, V or Nb were prepared in small (~100 mg) quantities by precipitation substantially as described in connection with Example 1. Table 10A summarizes the composition and amounts of the various catalyst compositions.

In an initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiTiSmCs oxide compositions ranged from 13.8% (with ethylene selectivity of 76.5%) to 18.2% (with ethylene selectivity of 83.7%), and ethylene selectivity values ranged from 76.5% (with ethane conversion of 13.8%) to 84.7% (with ethane conversion of 18.0%). Ethane conversion values for the NiTiSmMg oxide compositions ranged from 15.9% (with ethylene selectivity of 85.2%) to 19.1% (with ethylene selectivity of 85.4%), and ethylene selectivity values ranged from 83.9% (with ethane conversion of 17.3%) to 85.7% (with ethane conversion of 17.3%). Ethane conversion values for the NiTiSmCa oxide compositions ranged from 14.5% (with ethylene selectivity of 78.7%) to 19.1% (with ethylene selectivity of 83.5%), and ethylene selectivity values ranged from 78.7% (with ethane conversion of 14.5%) to 85.6% (with ethane conversion of 15.9%). Ethane conversion values for the NiTiSmSb oxide compositions ranged from 15.6% (with ethylene selectivity of 83.2%) to 18.7% (with ethylene selectivity of 83.1%), and ethylene selectivity values ranged from 81.5% (with ethane conversion of 16.3%) to 85.1% (with ethane conversion of 17.9%). Ethane conversion values for the NiTiSmBi oxide compositions ranged from 11.1% (with ethylene selectivity of 60.1%) to 17.9% (with ethylene selectivity of 86.1%), and ethylene selectivity values ranged from 59.0% (with ethane conversion of 11.3%) to 86.1% (with ethane conversion of 17.9%). Ethane conversion values for the NiTiSmV oxide compositions ranged from 12.1% (with ethylene selectivity of 76.5%) to 16.9% (with ethylene selectivity of 83.5%), and ethylene selectivity values ranged from 74.8% (with ethane conversion of 13.3%) to 83.5% (with ethane conversion of 16.9%). Ethane conversion (C) and ethylene selectivity (S) values for the NiTiSmNb oxide compositions ranged from 16.0% C, 80.4% S to 20.0% C, 85.5% S. Ethane conversion values for the NiTiSmTa oxide compositions ranged from 6.1% (with ethylene selectivity of 72.7%) to 20.0% (with ethylene selectivity of 85.5%), and ethylene selectivity values ranged from 72.7% (with ethane conversion of 6.1%) to 87.3% (with ethane conversion of 18.8%).

In a second screening in the fixed bed parallel reactor at 300° C. with different flowrates (ethane:nitrogen:oxygen of 0.42:0.23:0.061 sccm), ethane conversion values for the NiTiSmCs oxide compositions ranged from 15.0% (with ethylene selectivity of 80.4%) to 19.3% (with ethylene selectivity of 88.4%), and ethylene selectivity values ranged from 80.4% (with ethane conversion of 15.0%) to 90.2% (with ethane conversion of 18.3%). Ethane conversion values for the NiTiSmMg oxide compositions ranged from 17.3% (with ethylene selectivity of 89.4%) to 20.0% (with ethylene selectivity of 88.5%), and ethylene selectivity values ranged from 87.3% (with ethane conversion of 18.3%) to 90.2% (with ethane conversion of 17.9%). Ethane conversion values for the NiTiSmCa oxide compositions ranged from 15.2% (with ethylene selectivity of 83.9%) to 20.0% (with ethylene selectivity of 86.9%), and ethylene selectivity values ranged from 83.9% (with ethane conversion of 15.2%) to 89.9% (with ethane conversion of 17.9%). Ethane conversion values for the NiTiSmSb oxide compositions ranged from 15.9% (with ethylene selectivity of 86.9%) to 19.1% (with ethylene selectivity of 88.1%), and ethylene selectivity values ranged from 85.2% (with ethane conversion of 17.3%) to 88.1% (with ethane conversion of 19.1%). Ethane conversion values for the NiTiSmBi oxide compositions ranged from 13.2% (with ethylene selectivity of 81.4%) to 19.9% (with ethylene selectivity of 85.8%), and ethylene selectivity values ranged from 78.1% (with ethane conversion of 14.1%) to 85.9% (with ethane conversion of 16.7%). Ethane conversion values for the NiTiSmV oxide compositions ranged from 14.5% (with ethylene selectivity of 81.8%) to 17.9% (with ethylene selectivity of 84.3%), and ethylene selectivity values ranged from 78.7% (with ethane conversion of 15.1%) to 86.1% (with ethane conversion of 17.1%). Ethane conversion (C) and ethylene selectivity (S) values for the NiTiSmNb oxide compositions ranged from 17.3% C, 84.7% S to 19.6% C, 89.1% S. Ethane conversion (C) and ethylene selectivity (S) values for the NiTiSmNb oxide compositions ranged from 7.3% C, 72.8% S to 20.3% C, 89.5% S.

TABLE 10A

Catalyst composition (mole fraction) of NiTiSmX oxide catalysts, where X is Cs, Mg, Ca, Sb, Bi, V or Nb, and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 0.6667 | 0.6593 | 0.6522 | 0.6452 | 0.6383 | 0.6316 |
|   | Ti | 0.3056 | 0.3022 | 0.2989 | 0.2957 | 0.2926 | 0.2895 |
|   | Sm | 0.0278 | 0.0275 | 0.0272 | 0.0269 | 0.0266 | 0.0263 |
|   | Cs | 0.0000 | 0.0110 | 0.0217 | 0.0323 | 0.0426 | 0.0526 |
|   | m  | 48.8   | 49.5   | 50.3   | 50.2   | 50.2   | 50.5   |
| 2 | Ni | 0.6621 | 0.6557 | 0.6495 | 0.6434 | 0.6375 | 0.6316 |
|   | Ti | 0.3034 | 0.3005 | 0.2977 | 0.2949 | 0.2922 | 0.2895 |
|   | Mg | 0.0069 | 0.0164 | 0.0257 | 0.0349 | 0.0438 | 0.0526 |
|   | Sm | 0.0276 | 0.0273 | 0.0271 | 0.0268 | 0.0266 | 0.0263 |
|   | m  | 49.4   | 50.2   | 50.6   | 49.5   | 49.3   | 50.3   |
| 3 | Ni | 0.6621 | 0.6557 | 0.6495 | 0.6434 | 0.6375 | 0.6316 |
|   | Ti | 0.3034 | 0.3005 | 0.2977 | 0.2949 | 0.2922 | 0.2895 |
|   | Ca | 0.0069 | 0.0164 | 0.0257 | 0.0349 | 0.0438 | 0.0526 |
|   | Sm | 0.0276 | 0.0273 | 0.0271 | 0.0268 | 0.0266 | 0.0263 |
|   | m  | 49.7   | 49.2   | 50.8   | 50.5   | 50.2   | 50.6   |
| 4 | Ni | 0.6624 | 0.6560 | 0.6498 | 0.6437 | 0.6377 | 0.6318 |
|   | Ti | 0.3036 | 0.3007 | 0.2978 | 0.2950 | 0.2923 | 0.2896 |
|   | Sm | 0.0276 | 0.0273 | 0.0271 | 0.0268 | 0.0266 | 0.0263 |
|   | Sb | 0.0065 | 0.0160 | 0.0253 | 0.0345 | 0.0435 | 0.0524 |
|   | m  | 50.7   | 49.6   | 49.6   | 49.8   | 50.6   | 49.7   |
| 5 | Ni | 0.6621 | 0.6557 | 0.6495 | 0.6434 | 0.6375 | 0.6316 |
|   | Ti | 0.3034 | 0.3005 | 0.2977 | 0.2949 | 0.2922 | 0.2895 |
|   | Sm | 0.0276 | 0.0273 | 0.0271 | 0.0268 | 0.0266 | 0.0263 |
|   | Bi | 0.0069 | 0.0164 | 0.0257 | 0.0349 | 0.0438 | 0.0526 |
|   | m  | 49.5   | 50.5   | 49.8   | 49.5   | 51.3   | 49.5   |
| 6 | Ni | 0.6621 | 0.6557 | 0.6495 | 0.6434 | 0.6375 | 0.6316 |
|   | Ti | 0.3034 | 0.3005 | 0.2977 | 0.2949 | 0.2922 | 0.2895 |
|   | Sm | 0.0276 | 0.0273 | 0.0271 | 0.0268 | 0.0266 | 0.0263 |
|   | V  | 0.0069 | 0.0164 | 0.0257 | 0.0349 | 0.0438 | 0.0526 |
|   | m  | 50.3   | 45.0   | 49.5   | 49.7   | 50.6   | 50.0   |
| 7 | Ni | 0.6554 | 0.6360 | 0.6177 | 0.6005 | 0.5842 | 0.5687 |
|   | Nb | 0.0169 | 0.0460 | 0.0734 | 0.0993 | 0.1237 | 0.1469 |
|   | Ti | 0.3004 | 0.2915 | 0.2831 | 0.2752 | 0.2677 | 0.2607 |
|   | Sm | 0.0273 | 0.0265 | 0.0257 | 0.0250 | 0.0243 | 0.0237 |
|   | m  | 49.5   | 50.3   | 49.5   | 49.4   | 50.5   | 49.6   |
| 8 | Ni | 0.6541 | 0.6350 | 0.6170 | 0.6000 | 0.5839 | 0.5686 |
|   | Ti | 0.2998 | 0.2911 | 0.2828 | 0.2750 | 0.2676 | 0.2606 |
|   | Ta | 0.0188 | 0.0475 | 0.0745 | 0.1000 | 0.1242 | 0.1471 |
|   | Sm | 0.0273 | 0.0265 | 0.0257 | 0.0250 | 0.0243 | 0.0237 |
|   | m  | 49.2   | 50.2   | 49.9   | 51.1   | 50.1   | 50.0   |

In another independent experiment, a NiTiNbTaSm oxide catalyst having the composition $Ni_{0.68}Ti_{0.10}Nb_{0.10}Ta_{0.10}Sm_{0.02}O_x$ was prepared and screened in the parallel fixed bed reactor. Briefly, the following aqueous stock solutions were added to a glass vial in the amounts indicated: nickel nitrate ([Ni]=1.0M, 2.0 ml), titanium oxalate ([Ti]=0.713M with oxalic acid 0.18M), niobium oxalate ([Nb]=0.569M with oxalic acid 0.173M, 0.517 ml), tantalum oxalate ([Ta]=0.650M with oxalic acid 0.14M, 0.452 ml) and samarium nitrate ([Sm]=0.506M, 0.116 ml). Tetramethylammonium hydroxide ([NMe$_4$OH]=1.44M, 3.06 ml) was injected into the catalyst precursor composition, resulting in precipitation. To insure adequate mixing, distilled water (3.0 ml) was also injected into the mixture. The resulting precipitate mixture was settled at 25° C. for 2 hours, and then centrifuged at 300 rpm. The solution was decanted and the solids were dried under vacuum at 60° C. in a vacuum oven. The dried materials were then calcined by heating to 320° C. at 5° C./min and maintaining at 320° C. for 8 hours in air. After subsequent cooling to 25° C., solid NiTiNbTaSm oxide (0.296 g) was obtained and 48.7 mg thereof was tested for ethane oxidative dehydrogenation in the parallel fixed bed reactor at 300° C. with an ethane:oxygen flow of 0.42:0.083 sccm. Ethane conversion (C) and ethylene selectivity (S) were determined to be 22.3% C and 85.2% S.

Example 11

ODHE over NiTiSn/NiZrSn Oxide Catalysts (# 16470/16505)

Catalyst compositions comprising various NiTiSn and NiZrSn oxides were prepared and screened substantially as described in connection with Example 1, with tin acetate ([Sn=0.249 M]) aqueous stock solution. The various catalyst compositions and amounts are summarized in Table 11A (NiTiSn oxides) and Table 11B (NiZrSn oxides).

For the NiTiSn oxide catalysts, in an initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiTiSn oxide compositions ranged from 11.1% (with ethylene selectivity of 79.4%) to 19.2% (with ethylene selectivity of 85.4%), and ethylene selectivity values ranged from 79.2% (with ethane conversion of 14.8%) to 86.1% (with ethane conversion of 18.2%).

In a second screening of these catalysts in the fixed bed parallel reactor at 300° C. with different flowrates (ethane:nitrogen:oxygen of 1.04:0.21:0.055 sccm), ethane conversion values for the NiTiSn oxide compositions ranged from 8.5% (with ethylene selectivity of 90.8%) to 10.2% (with ethylene selectivity of 94.0%), and ethylene selectivity values ranged from 90.8% (with ethane conversion of 8.5%) to 94.3% (with ethane conversion of 9.9%).

In a third screening of these catalysts in the fixed bed parallel reactor at a different temperature, 275° C., and with different flowrates (ethane:nitrogen:oxygen of 1.05:0.082:0.022), ethane conversion values for the NiTiSn oxide compositions ranged from 3.5% (with ethylene selectivity of 86.0%) to 8.5% (with ethylene selectivity of 92.8%), and ethylene selectivity values ranged from 85.4% (with ethane conversion of 4.4%) to 93.4% (with ethane conversion of 7.9%).

For the NiZrSn oxide catalysts, in an initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiZrSn oxide compositions ranged from 15.0% (with ethylene selectivity of 77.3%) to 17.8% (with ethylene selectivity of 80.9%), and ethylene selectivity values ranged from 77.2% (with ethane conversion of 15.6%) to 81.9% (with ethane conversion of 17.1%).

In a second screening of these catalysts in the fixed bed parallel reactor at 300° C. with different flowrates (ethane:nitrogen:oxygen of 1.04:1.34:0.22 sccm), ethane conversion values for the NiZrSn oxide compositions ranged from 8.2% (with ethylene selectivity of 87.8%) to 9.3% (with ethylene selectivity of 90.9%), and ethylene selectivity values ranged from 87.8% (with ethane conversion of 8.2%) to 91.8% (with ethane conversion of 9.1%).

In a third screening of these catalysts in the fixed bed parallel reactor at a different temperature, 275° C., and with different flowrates (ethane:nitrogen:oxygen of 1.04:0.021:0.055), ethane conversion values for the NiZrSn oxide compositions ranged from 5.8% (with ethylene selectivity of 83.3%) to 7.8% (with ethylene selectivity of 88.3%), and ethylene selectivity values ranged from 82.2% (with ethane conversion of 6.3%) to 88.9% (with ethane conversion of 7.6%).

TABLE 11A

Catalyst composition (mole fraction) of NiTiSn oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.875 | | | | | |
| | Ti | 0.125 | | | | | |
| | Sn | 0.000 | | | | | |
| | mass (mg) | 51.7 | | | | | |
| 2 | Ni | 0.862 | 0.787 | | | | |
| | Ti | 0.129 | 0.213 | | | | |
| | Sn | 0.009 | 0.000 | | | | |
| | mass (mg) | 54.2 | 48.2 | | | | |
| 3 | Ni | 0.847 | 0.771 | 0.708 | | | |
| | Ti | 0.134 | 0.220 | 0.292 | | | |
| | Sn | 0.019 | 0.008 | 0.000 | | | |
| | mass (mg) | 53.9 | 46.1 | 46.6 | | | |
| 4 | Ni | 0.832 | 0.755 | 0.691 | 0.637 | | |
| | Ti | 0.139 | 0.228 | 0.301 | 0.363 | | |
| | Sn | 0.029 | 0.018 | 0.008 | 0.000 | | |
| | mass (mg) | 53.0 | 50.0 | 51.0 | 48.0 | | |
| 5 | Ni | 0.815 | 0.736 | 0.672 | 0.618 | 0.572 | |
| | Ti | 0.145 | 0.236 | 0.311 | 0.374 | 0.428 | |
| | Sn | 0.040 | 0.027 | 0.017 | 0.008 | 0.000 | |
| | mass (mg) | 45.0 | 52.3 | 50.0 | 52.8 | 46.1 | |
| 6 | Ni | 0.796 | 0.717 | 0.652 | 0.598 | 0.552 | 0.513 |
| | Ti | 0.151 | 0.245 | 0.322 | 0.386 | 0.441 | 0.487 |
| | Sn | 0.052 | 0.038 | 0.026 | 0.016 | 0.007 | 0.000 |
| | mass (mg) | 49.5 | 46.4 | 52.0 | 44.9 | 50.6 | 49.1 |

TABLE 11B

Catalyst composition (mole fractions) of NiZrSn oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.914 | | | | | |
| | Zr | 0.086 | | | | | |
| | Sn | 0.000 | | | | | |
| | mass (mg) | 45.8 | | | | | |
| 2 | Ni | 0.901 | 0.849 | | | | |
| | Zr | 0.089 | 0.151 | | | | |
| | Sn | 0.009 | 0.000 | | | | |
| | mass (mg) | 52.9 | 51.2 | | | | |
| 3 | Ni | 0.888 | 0.834 | 0.786 | | | |
| | Zr | 0.093 | 0.157 | 0.214 | | | |
| | Sn | 0.020 | 0.009 | 0.000 | | | |
| | mass (mg) | 50.9 | 50.6 | 47.6 | | | |
| 4 | Ni | 0.873 | 0.818 | 0.770 | 0.727 | | |
| | Zr | 0.097 | 0.163 | 0.221 | 0.273 | | |
| | Sn | 0.031 | 0.019 | 0.009 | 0.000 | | |
| | mass (mg) | 55.6 | 54.4 | 53.1 | 51.2 | | |
| 5 | Ni | 0.857 | 0.801 | 0.752 | 0.708 | 0.670 | |
| | Zr | 0.101 | 0.169 | 0.230 | 0.283 | 0.330 | |
| | Sn | 0.043 | 0.030 | 0.019 | 0.009 | 0.000 | |
| | mass (mg) | 55.1 | 51.8 | 49.2 | 53.8 | 49.2 | |
| 6 | Ni | 0.839 | 0.782 | 0.732 | 0.688 | 0.649 | 0.615 |
| | Zr | 0.105 | 0.176 | 0.239 | 0.293 | 0.342 | 0.385 |
| | Sn | 0.056 | 0.042 | 0.029 | 0.018 | 0.009 | 0.000 |
| | mass (mg) | 51.8 | 51.3 | 45.5 | 59.0 | 50.7 | 50.6 |

Example 12

ODHE over Bulk NiTa, NiNb, NiNbTa (Various Forms), NiNbTaCe, NiTa(Ce, Dy), and NiNb(Ce, Sb, Dy, Sm) Oxide Catalysts In a first group of experiments, various NiTa, NiTaNb, NiNbCe and NiNbSb oxide catalysts were prepared in large, bulk quantities (~20 g), and ~50 mg thereof was screened in the parallel fixed bed reactor at 300° C. with ethane:nitrogen:oxygen flow of 0.42:0.54:0.088 sccm, as follows. Catalyst compositions, sample mass, and resulting ethane conversion and ethylene selectivity are summarized in Table 12A.

(#12087) $Ni_{0.83}Ta_{0.17}$: Aqueous solution of nickel nitrate (1.0M, 167.0 ml) was mixed with tantalum oxalate (0.66M in water with 0.26M oxalic acid, 53.0 ml). To the stirring mixture of nickel nitrate and tantalum oxalate, tetramethylammonium hydroxide aqueous solution (1.42M, 210.0 ml) was added to give precipitation. The water in the mixture was removed by freeze-drying, and the resulting solid was then calcined under an atmosphere of air at the heating rate of 1° C./min to the temperature of 120° C., dwelled at 120 C for 2 hrs, at the heating rate of 1° C./min to 180° C., dwelled at 180° C. for 2 hrs, at the heating rate of 2° C./min to 400° C. and dwelled at 400° C. for 8 hrs, and then cooled to 25° C. Gray solid NiTa oxide (18.0 g) were obtained and 50.0 mg thereof was tested in the fixed bed parallel reactor for ethane oxidative dehydrogenation under the aforementioned conditions.

(#12277) $Ni_{0.62}Ta_{0.19}Nb_{0.19}$: Aqueous solution of nickel nitrate (1.0M, 153.0 ml), tantalum oxalate aqueous solution (0.66M in water with 0.26M oxalic acid, 73.0 ml), and niobium oxalate aqueous solution (0.62M in water with 0.35M oxalic acid, 76.0 ml) were mixed in a 2 L beaker. While the solution was vigorously stirred by a mechanical stir, ammonium carbonate aqueous solution (1.62M, 285.0 ml) was added in a controlled manner so that the foam was formed slowly to give precipitation. The mixture was transferred to containers, which was centrifuged at 4000 rpm for 15 minutes. The solution was decanted and solid materials were further dried at 60° C. under reduced pressure for 5 hours. The resulting solid materials were calcined under an atmosphere of air at 3° C./min to 350° C. and dwelled at 350° C. for 8 hours, and then cooled to 25° C. Dark gray solid NiTaNb oxide (19.0 g) was obtained, and 50.0 mg thereof was tested in the parallel fixed bed reactor for ethane oxidative dehydrogenation under the aforementioned conditions.

(#12442) $Ni_{0.62}Ta_{0.10}Nb_{0.28}$: Aqueous solution of nickel nitrate (1.0M, 80.0 ml), tantalum oxalate aqueous solution (0.66M in water with 0.26M oxalic acid, 19.0 ml), and niobium oxalate aqueous solution (0.62M in water with 0.35M oxalic acid, 57.0 ml) were mixed in a 2 L beaker. While the solution was vigorously stirred by a mechanical stir, ammonium carbonate aqueous solution (1.62M, 143.0 ml) was added in a controlled manner so that the foam was formed slowly to give precipitation. The mixture was transferred to containers, which was centrifuged at 4000 rpm for 15 minutes. The solution was decanted and solid materials were further dried at 60° C. under reduced pressure for 5 hours. The resulting solid materials were calcined under an atmosphere of air at 2° C./min to 300° C. and dwelled at 300° C. for 8 hours, and then cooled to 25° C. Dark gray solid NiTaNb oxide (12.0 g) was obtained and about 50 mg thereof was tested in the parallel fixed bed reactor for ethane oxidative dehydrogenation under the aforementioned conditions.

(#14560) $Ni_{0.65}Nb_{0.33}Ce_{0.02}O_x$: Aqueous solution of nickel nitrate (1.0M, 150.0 ml), niobium oxalate aqueous solution (0.58M in water with 0.14M oxalic acid, 131.0 ml), and cerium nitrate (1.0 M, 4.6 ml) were mixed in a 2 L beaker. While the solution was vigorously stirred by a mechanical stir, ammonium carbonate aqueous solution (1.62M, 214.7 ml) was added in a controlled manner so that the foam was formed slowly to give precipitation. The mixture was transferred to containers, which was centrifuged at 4000 rpm for 15 minutes. The solution was decanted and solid materials were further dried at 60° C. under reduced pressure for 5 hours. The resulting solid materials were calcined under an atmosphere of air at 2° C./min to 300° C. and dwelled at 300° C. for 8 hours, and then cooled to 25° C. Dark gray solid NiNbCe oxide (20.94 g) was obtained and 45.8 mg thereof was tested in the parallel fixed bed reactor for ethane oxidative dehydrogenation under the aforementioned conditions.

(#14620) $Ni_{0.65}Nb_{0.33}Ce_{0.02}O_x$: NiNbCe oxide (10.41 g) prepared as described above in connection with library #14560 was further calcined to 400° C. at 2° C./min and dwelled at 400° C. for 8 hrs under an atmosphere of air. Solid NiNbCe oxide (10.19 g) was obtained, and 49.2 mg thereof was tested in the parallel fixed bed reactor for ethane oxidative dehydrogenation under the aforementioned conditions.

(#14587) $Ni_{0.71}Nb_{0.27}Sb_{0.02}O_x$: Aqueous solution of nickel nitrate (1.0M, 150.0 ml), niobium oxalate aqueous solution (0.58M in water with 0.14M oxalic acid, 98.3 ml), and antimony acetate aqueous solution (0.234M with oxalic acid 1.27M, 18.1 ml) were mixed in a 2 L beaker. While the solution was vigorously stirred by a mechanical stir, ammonium carbonate aqueous solution (1.62M, 228.4 ml) was added in a controlled manner so that the foam was formed slowly to give precipitation. The mixture was transferred to containers, which was centrifuged at 4000 rpm for 15 minutes. The solution was decanted and solid materials were further dried at 60° C. under reduced pressure for 5 hours. The resulting solid materials were calcined under an atmosphere of air at 2° C./min to 300° C. and dwelled at 300° C. for 8 hours, and then cooled to 25° C. Dark gray solid NiNbSb oxide (18.75 g) was obtained and 54.8 mg thereof was tested in the parallel fixed bed reactor for ethane oxidative dehydrogenation under the aforementioned conditions.

(#14624) $Ni_{0.71}Nb_{0.27}Sb_{0.02}O_x$: NiNbSb oxide (8.86 g) prepared as described above in connection with library #14587 was further calcined to 400° C. at 2° C./min and dwelled at 400° C. for 8 hrs under an atmosphere of air. Solid NiNbSb oxide (8.60 g) was obtained, and 54.1 mg thereof was tested in the parallel fixed bed reactor for ethane oxidative dehydrogenation under the aforementioned conditions.

TABLE 12A

Catalyst composition (mole fractions), sample mass (mg) and performance characteristics of various NiTa, NiTaNb, NiNbCe and NiNbSb oxide catalysts. Test conditions: 300° C. with ethane:nitrogen:oxygen flow of 0.42:0.54:0.088 sccm.

| Library # | Composition | Mass (mg) | Conversion | Selectivity |
|---|---|---|---|---|
| 12087 | $Ni_{0.83}Ta_{0.17}O_x$ | 50.0 | 11.1% | 85.0% |
| 12277 | $Ni_{0.62}Ta_{0.19}Nb_{0.19}O_x$ | 50.0 | 10.0% | 85.4% |
| 12442 | $Ni_{0.62}Ta_{0.10}Nb_{0.28}O_x$ | 50.0 | 17.0% | 83.7% |
| 14560 | $Ni_{0.65}Nb_{0.33}Ce_{0.02}O_x$ | 45.8 | 18.6% | 83.0% |
| 14620 | $Ni_{0.65}Nb_{0.33}Ce_{0.02}O_x$ | 49.2 | 13.8% | 82.0% |
| 14587 | $Ni_{0.71}Nb_{0.27}Sb_{0.02}O_x$ | 54.8 | 20.2% | 81.6% |
| 14624 | $Ni_{0.71}Nb_{0.27}Sb_{0.02}O_x$ | 54.1 | 14.4% | 82.5% |

In another group of experiments, various NiTa, NiTaCe, NiTaDy, NiNbTaCe, NiNbDy, NiNb and titania supported NiNbSm oxide catalysts were prepared in large, bulk quantities (~20 g), and various amounts thereof were screened in the parallel fixed bed reactor at 300° C. with ethane:nitrogen:oxygen flow of 0.42:0.08:0.022 sccm, as follows. Catalyst compositions, sample mass, and resulting ethane conversion and ethylene selectivity are summarized in Table 12B.

(#15891) $Ni_{0.86}Ta_{0.14}O_x$: Aqueous solution of nickel nitrate (1.0M, 150.0 ml), and tantalum oxalate aqueous solution (0.69M in water with 0.19M oxalic acid, 35.0 ml) were mixed in a 1 L beaker. While the solution was vigorously stirred by a mechanical stir, ammonium carbonate aqueous solution (1.62M, 150.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiTa oxide (15.0 g) was obtained and 45.6 mg thereof was tested in the parallel fixed bed reactor for ethane oxidative dehydrogenation under the aforementioned reaction conditions.

(#15915) $Ni_{0.65}Ta_{0.31}Ce_{0.04}O_x$: Aqueous solution of nickel nitrate (1.0M, 120.0 ml), tantalum oxalate aqueous solution (0.69M in water with 0.19M oxalic acid, 83.0 ml), and cerium nitrate aqueous solution (0.50M, 15.0 ml) were mixed in a 1 L beaker. While the solution was vigorously stirred by a mechanical stir, ammonium carbonate aqueous solution (1.62M, 174.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320 CC for 8 hours, and then cooled to 25° C. Dark gray solid NiTaCe oxide (21.9 g) was obtained and 51.3 mg thereof was tested in the parallel fixed bed reactor for ethane oxidative dehydrogenation under the aforementioned reaction conditions.

(#15916) $Ni_{0.73}Ta_{0.24}Dy_{0.03}O_x$: Aqueous solution of nickel nitrate (1.0M, 150.0 ml), tantalum oxalate aqueous solution (0.51M in water with 0.67M oxalic acid, 97.0 ml), and dysprosium acetate aqueous solution (0.294M, 21.0 ml) were mixed in a 1 L beaker. While the solution was vigorously stirred by a mechanical stir, ammonium carbonate aqueous solution (1.62M, 269.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiTaDy oxide (21.9 g) was obtained and 50.0 mg thereof was tested in the parallel fixed bed reactor for ethane oxidative dehydrogenation under the aforementioned reaction conditions.

(#15922) $Ni_{0.74}Nb_{0.08}Ta_{0.17}Ce_{0.01}O_x$: Aqueous solution of nickel nitrate (1.0M, 150.0 ml), tantalum oxalate aqueous solution (0.51M in water with 0.67M oxalic acid, 68.0 ml), niobium oxalate aqueous solution (0.62M in water with 0.21M oxalic acid, 26.0 ml), and cerium nitrate aqueous solution (0.50M, 4.0 ml) were mixed in a 1 L beaker. While the solution was vigorously stirred by a mechanical stir, ammonium carbonate aqueous solution (1.62M, 235.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiNbTaCe oxide (20.7 g) was obtained and 68.5 mg thereof was tested in the parallel fixed bed reactor for ethane oxidative dehydrogenation under the aforementioned reaction conditions.

(#15927) $Ni_{0.68}Nb_{0.25}Dy_{0.04}O_x$: Aqueous solution of nickel nitrate (1.0M, 150.0 ml), niobium oxalate aqueous solution (0.62M in water with 0.21M oxalic acid, 89.0 ml), and dysprosium acetate aqueous solution (0.294M, 53.0 ml) were mixed in a 1 L beaker. While the solution was vigorously stirred by a mechanical stir, ammonium carbonate aqueous solution (1.62M, 206.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiNbDy oxide (19.4 g) was obtained and 47.0 mg thereof tested in the parallel fixed bed reactor for ethane oxidative dehydrogenation under the aforementioned reaction conditions.

(#15931) $Ni_{0.82}Nb_{0.18}O_x$: Aqueous solution of nickel nitrate (1.0M, 150.0 ml), and niobium oxalate aqueous solution (0.62M in water with 0.21M oxalic acid, 53.0 ml) were mixed in a 1 L beaker. While the solution was vigorously stirred by a mechanical stir, ammonium carbonate aqueous solution (1.62M, 164.0 ml) was added in a controlled manner so that the foam was formed slowly to give precipitation. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiNb oxide (14.1 g) was obtained and 47.3 mg thereof was tested in the parallel fixed bed reactor for ethane oxidative dehydrogenation under the aforementioned reaction conditions.

(#15944) $Ni_{0.63}Nb_{0.34}Sm_{0.03}O_x/TiO_2$: $TiO_2$ support in pellet form was dried at 100° C. for over 8 hrs. After cooling to 25° C., $TiO_2$ support was impregnated with the mixed metal nitrate or oxalate solution. Catalyst loading was about 6% by weight, relative to total weight of the catalyst. After centrifugation, the solid materials obtained were dried at 60° C. under vacuum, and then calcined to 300° C. at 2° C./min and dwelled at 300° C. for 8 hrs. The NiNbSm oxide was obtained and ~143 mg thereof was tested in the parallel fixed bed reactor for ethane oxidative dehydrogenation under the aforementioned reaction conditions.

TABLE 12B

Catalyst composition (mole fractions), sample mass (mg) and performance characteristics of various NiTa, NiTaCe, NiTaDy, NiNbTaCe, NiNbDy, NiNb and titania supported NiNbSm oxide catalysts. Test conditions: 300° C. with ethane:nitrogen:oxygen flow of 0.42:0.08:0.022 sccm.

| Library # | Composition | Mass (mg) | Conversion | Selectivity |
|---|---|---|---|---|
| 15891 | $Ni_{0.86}Ta_{0.14}O_x$ | 45.6 mg | 10.3% | 91.3% |
| 15915 | $Ni_{0.65}Ta_{0.31}Ce_{0.04}O_x$ | 51.3 mg | 10.5% | 93.2% |
| 15916 | $Ni_{0.73}Ta_{0.24}Dy_{0.03}O_x$ | 50.0 mg | 10.2% | 93.3% |
| 15922 | $Ni_{0.74}Nb_{0.08}Ta_{0.17}Ce_{0.01}O_x$ | 68.5 mg | 10.8% | 94.3% |
| 15927 | $Ni_{0.68}Nb_{0.25}Dy_{0.07}O_x$ | 47.0 mg | 10.5% | 91.8% |
| 15931 | $Ni_{0.82}Nb_{0.18}O_z$ | 47.3 mg | 10.2% | 93.1% |
| 15944 | $Ni_{0.63}Nb_{0.34}Sm_{0.030}O_x/TiO2^*$ | 142.8 mg | 8.6% | 93.0% |

*Catalyst loading on the support is about 6% by weight.

In a third group of experiments, NiNbTa oxide catalysts of a single composition were prepared in large, bulk quantities (~20 g) and in various physical forms, and various amounts thereof were screened in the parallel fixed bed reactor at 300° C. with ethane:nitrogen:oxygen flow of 0.42:0.54:0.088 sccm, as follows. The catalyst composition, physical form, sample mass and resulting ethane conversion and ethylene selectivity are summarized in Table 12C.

(#16116) $Ni_{0.63}Nb_{0.19}Ta_{0.18}O_x$: Aqueous solution of nickel nitrate (1.0M, 150.0 ml), niobium oxalate aqueous solution (0.62M in water with 0.21M oxalic acid, 73.0 ml), and tantalum oxalate aqueous solution (0.51M in water with 0.67M oxalic acid, 84.0 ml), were mixed in a 1 L beaker. While the solution was vigorously stirred by a mechanical stir, tetramethylammonium hydroxide aqueous solution (1.28M, 390.0 ml) was added quickly to give precipitation. Additional water (100 ml) was added and mixed with the resulting mixture. The mixture was transferred to containers, which was centrifuged at 3000 rpm for 15 minutes. The solution was decanted and solid materials were further dried at 60° C. under reduced pressure for 5 hours. The resulting solid materials were calcined under an atmosphere of air at 2° C./min to 320° C. and dwelled at 320° C. for 8 hours, and then cooled to 25° C. Dark gray solid NiNbTa oxide (15.9 g) was obtained and 50.0 mg thereof was tested, as formed in bulk, in the parallel fixed bed reactor for ethane oxidative dehydrogenation under the aforementioned reaction conditions.

For comparison of the effect of physical form of the catalyst, a portion of the NiNbTa oxide bulk catalyst prepared as above was pressed and broken into small pieces (but not ground) to fit into the reaction vessels of the parallel fixed bed reactor, and 73.9 mg thereof was tested, in pressed and broken form, in the parallel fixed bed reactor for ethane oxidative dehydrogenation under the aforementioned reaction conditions. Additionally, another portion of the NiNbTa oxide bulk catalyst prepared as described above was pressed and ground, and 68.0 mg thereof was tested, in pressed and ground form, in the parallel fixed bed reactor for ethane oxidative dehydrogenation under the aforementioned reaction conditions.

TABLE 12C

Physical form, sample mass (mg) and performance characteristics of $Ni_{0.63}Nb_{0.19}Ta_{0.18}O_x$ catalysts (#16116). Test conditions: 300° C. with ethane:nitrogen:oxygen flow of 0.42:0.54:0.088 sccm.

| Composition | Form | Mass (mg) | Conversion | Selectivity |
|---|---|---|---|---|
| $Ni_{0.63}Nb_{0.19}Ta_{0.18}O_x$ | bulk | 50.0 | 18.4 | 84.1 |
| $Ni_{0.63}Nb_{0.19}Ta_{0.18}O_x$ | P*, B* | 73.9 | 20.1 | 85.0 |
| $Ni_{0.63}Nb_{0.19}Ta_{0.18}O_z$ | P*, G* | 68.0 | 19.1 | 84.6 |

P* = pressed; B* = broken (not ground); G* = ground.

Example 13

ODHE over NiNbSmX Oxide Catalyst, X=Cs, Mg, Ca, Sb, Bi, V, Ti, Ta (#16298/16507)

Catalyst compositions comprising various NiNbSmX oxides, where X is Cs, Mg, Ca, Sb, Bi, V, Ti or Ta were prepared in bulk (~20 g) quantities by precipitation substantially as described in connection with Example 1. Nickel nitrate ([Ni]=1.0 M), niobium oxalate ([Nb]=0.569 M), samarium nitrate ([Sm]=0.506 M), cesium nitrate ([Cs]=1.00 M), magnesium nitrate ([Mg]=1.00 M), calcium nitrate ([Ca]=1.00 M), antimony acetate ([Sb]=0.234 M), bismuth citrate ([Bi]=0.293 M), vanadium oxalate ([V]=1.00 M), titanium oxalate ([Ti]=0.713 M), and tantalum oxalate ([Ta]=0.650 M) aqueous stock solutions were used. Table 13A summarizes the composition and amounts of the various catalyst compositions.

In an initial screening (calcination at 300° C., 8 hours, screening in fixed bed parallel reactor at 300° C. with flowrates of ethane:nitrogen:oxygen of 0.42:0.54:0.088 sccm, as described), ethane conversion (C) and ethylene selectivity (S) values for the NiNbSmCs oxide compositions ranged from 16.3% C, 78.5% S to 19.2% C, 84.9% S. Ethane conversion values for the NiNbSmMg oxide compositions ranged from 17.5% (with ethylene selectivity of 83.1%) to 19.4% (with ethylene selectivity of 84.8%), and ethylene selectivity values ranged from 83.1% (with ethane conversion of 17.5%) to 84.9% (with ethane conversion of 18.7%). Ethane conversion (C) and ethylene selectivity (S) values for the NiNbSmCa oxide compositions ranged from 18.2% C, 83.3% S to 20.0% C, 84.5% S. Ethane conversion (C) and ethylene selectivity (S) values for the NiNbSmSb oxide compositions ranged from 16.3% C, 80.3% S to 19.0% C, 86.4% S. Ethane conversion (C) and ethylene selectivity (S) values for the NiNbSmBi oxide compositions ranged from 17.1% C, 79.4% S to 19.5% C, 84.6% S. Ethane conversion values for the NiNbSmV oxide compositions ranged from 13.8% (with ethylene selectivity of 80.3%) to 17.7% (with ethylene selectivity of 84.3%), and ethylene selectivity values ranged from 79.9% (with ethane conversion of 14.0%) to 84.3% (with ethane conversion of 17.7%). Ethane conversion (C) and ethylene selectivity (S) values for the NiNbSmTi oxide compositions ranged from 17.6% C, 82.8% S to 19.1% C, 84.9% S. Ethane conversion values for the NiNbSmTa oxide compositions ranged from 17.3% (with ethylene selectivity of 83.6%) to 20.2% (with ethylene selectivity of 84.3%), and ethylene selectivity values ranged from 83.4% (with ethane conversion of 17.8%) to 84.9% (with ethane conversion of 18.2%).

In a second screening in the fixed bed parallel reactor at 300° C. with different flowrates (ethane:nitrogen:oxygen of 0.42:0.23:0.061 sccm), ethane conversion (C) and ethylene selectivity (S) values for the NiNbSmCs oxide compositions ranged from 17.0% C, 83.0% S to 19.8% C, 88.7% S. Ethane conversion values for the NiNbSmMg oxide compositions ranged from 16.0% (with ethylene selectivity of 88.3%) to 18.9% (with ethylene selectivity of 88.2%), and ethylene selectivity values ranged from 86.4% (with ethane conversion of 18.1% O) to 88.3% (with ethane conversion of 18.8%). Ethane conversion values for the NiNbSmCa oxide compositions ranged from 18.2% (with ethylene selectivity of 86.3%) to 19.8% (with ethylene selectivity of 87.6%), and ethylene selectivity values ranged from 86.3% (with ethane conversion of 18.2%) to 87.8% (with ethane conversion of 18.7%). Ethane conversion values for the NiNbSmSb oxide compositions ranged from 17.0% (with ethylene selectivity of 84.2%) to 19.5% (with ethylene selectivity of 89.3%), and ethylene selectivity values ranged from 84.2% (with ethane conversion of 17.0%) to 89.5% (with ethane conversion of 19.4%). Ethane conversion values for the NiNbSmBi oxide compositions ranged from 17.1% (with ethylene selectivity of 82.4%) to 19.8% (with ethylene selectivity of 87.7%), and ethylene selectivity values ranged from 82.4% (with ethane conversion of 17.1%) to 88.7% (with ethane conversion of 18.5%). Ethane conversion values for the NiNbSmV oxide compositions ranged from 14.0% (with ethylene selectivity of 76.7%) to 18.7% (with ethylene selectivity of 86.8%), and ethylene selectivity values ranged from 76.7% (with ethane conversion of 14.0%) to 88.2% (with ethane conversion of 17.8%). Ethane conversion values for the NiNbSmTi oxide compositions ranged from 17.7% (with ethylene selectivity of 87.3%) to 19.4% (with ethylene selectivity of 88.0%), and ethylene selectivity values ranged from 86.3% (with ethane conversion of 18.6%) to 88.2% (with ethane conversion of 19.1%). Ethane conversion values for the NiNbSmTa oxide compositions ranged from 18.1% (with ethylene selectivity of 86.8%) to 19.0% (with ethylene selectivity of 87.7%), and ethylene selectivity values ranged from 86.1% (with ethane conversion of 18.5%) to 87.8% (with ethane conversion of 18.1%).

TABLE 13A

Catalyst composition (mole fraction) of NiNbSmX Oxide Catalysts, where X is Cs, Mg, Ca, Sb, Bi, V, Ti or Ta, and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 0.7528 | 0.7439 | 0.7352 | 0.7267 | 0.7184 | 0.7103 |
|   | Nb | 0.2164 | 0.2138 | 0.2113 | 0.2089 | 0.2065 | 0.2042 |
|   | Sm | 0.0308 | 0.0304 | 0.0301 | 0.0297 | 0.0294 | 0.0291 |
|   | Cs | 0.0000 | 0.0118 | 0.0234 | 0.0347 | 0.0457 | 0.0565 |
|   | m  | 49.4 | 49.9 | 49.3 | 50.6 | 50.6 | 50.8 |
| 2 | Ni | 0.7464 | 0.7389 | 0.7315 | 0.7243 | 0.7172 | 0.7103 |
|   | Nb | 0.2146 | 0.2124 | 0.2103 | 0.2082 | 0.2062 | 0.2042 |
|   | Mg | 0.0085 | 0.0185 | 0.0283 | 0.0379 | 0.0473 | 0.0565 |
|   | Sm | 0.0305 | 0.0302 | 0.0299 | 0.0296 | 0.0293 | 0.0291 |
|   | m  | 49.6 | 49.8 | 49.3 | 49.7 | 49.9 | 50.4 |
| 3 | Ni | 0.7464 | 0.7389 | 0.7315 | 0.7243 | 0.7172 | 0.7103 |
|   | Nb | 0.2146 | 0.2124 | 0.2103 | 0.2082 | 0.2062 | 0.2042 |
|   | Ca | 0.0085 | 0.0185 | 0.0283 | 0.0379 | 0.0473 | 0.0565 |
|   | Sm | 0.0305 | 0.0302 | 0.0299 | 0.0296 | 0.0293 | 0.0291 |
|   | m  | 49.3 | 50.2 | 50.7 | 49.9 | 49.2 | 50.1 |
| 4 | Ni | 0.7468 | 0.7392 | 0.7317 | 0.7244 | 0.7172 | 0.7102 |
|   | Nb | 0.2147 | 0.2125 | 0.2103 | 0.2082 | 0.2062 | 0.2041 |
|   | Sm | 0.0306 | 0.0302 | 0.0299 | 0.0296 | 0.0293 | 0.0291 |
|   | Sb | 0.0079 | 0.0181 | 0.0280 | 0.0378 | 0.0473 | 0.0567 |
|   | m  | 50.8 | 49.8 | 50.2 | 50.9 | 50.8 | 49.9 |
| 5 | Ni | 0.7464 | 0.7389 | 0.7315 | 0.7243 | 0.7172 | 0.7103 |
|   | Nb | 0.2146 | 0.2124 | 0.2103 | 0.2082 | 0.2062 | 0.2042 |
|   | Sm | 0.0305 | 0.0302 | 0.0299 | 0.0296 | 0.0293 | 0.0291 |
|   | Bi | 0.0085 | 0.0185 | 0.0283 | 0.0379 | 0.0473 | 0.0565 |
|   | m  | 50.9 | 50.6 | 50.2 | 49.4 | 49.3 | 49.9 |

TABLE 13A-continued

Catalyst composition (mole fraction) of NiNbSmX Oxide Catalysts, where X is Cs, Mg, Ca, Sb, Bi, V, Ti or Ta, and sample mass, "m" (mg) used in parallel fixed bed reactor screen.

| | | Col | | | | | |
|---|---|---|---|---|---|---|---|
| Row | | 1 | 2 | 3 | 4 | 5 | 6 |
| 6 | Ni | 0.7464 | 0.7389 | 0.7315 | 0.7243 | 0.7172 | 0.7103 |
| | Nb | 0.2146 | 0.2124 | 0.2103 | 0.2082 | 0.2062 | 0.2042 |
| | Sm | 0.0305 | 0.0302 | 0.0299 | 0.0296 | 0.0293 | 0.0291 |
| | V | 0.0085 | 0.0185 | 0.0283 | 0.0379 | 0.0473 | 0.0565 |
| | m | 50.4 | 49.8 | 50.8 | 51.0 | 49.4 | 49.6 |
| 7 | Ni | 0.7401 | 0.7156 | 0.6926 | 0.6711 | 0.6508 | 0.6317 |
| | Nb | 0.2128 | 0.2057 | 0.1991 | 0.1929 | 0.1871 | 0.1816 |
| | Ti | 0.0168 | 0.0494 | 0.0800 | 0.1086 | 0.1355 | 0.1608 |
| | Sm | 0.0303 | 0.0293 | 0.0283 | 0.0275 | 0.0266 | 0.0258 |
| | m | 49.7 | 49.7 | 50.6 | 49.5 | 50.5 | 50.3 |
| 8 | Ni | 0.7389 | 0.7163 | 0.6950 | 0.6750 | 0.6561 | 0.6383 |
| | Nb | 0.2124 | 0.2059 | 0.1998 | 0.1940 | 0.1886 | 0.1835 |
| | Ta | 0.0185 | 0.0485 | 0.0767 | 0.1033 | 0.1284 | 0.1521 |
| | Sm | 0.0302 | 0.0293 | 0.0284 | 0.0276 | 0.0268 | 0.0261 |
| | m | 49.4 | 49.5 | 49.9 | 50.4 | 50.7 | 50.0 |

Example 14

ODHE over NiNbCu Oxide Catalysts.
(#16360/16511)

Catalyst compositions comprising various NiNbCu oxides were prepared in small (~100 mg) quantities by precipitation substantially as described in connection with Example 1, using copper nitrate ([Cu]=1.00 M) aqueous stock solution. Table 14A summarizes the composition and amounts of the various catalyst compositions.

In an initial screening (calcination at 300° C., 8 hours, screening in fixed bed parallel reactor at 300° C. with flowrates of ethane:nitrogen:oxygen of 0.42:0.54:0.088 sccm, as described), ethane conversion (C) and ethylene selectivity (S) values for the NiNbCu oxide compositions ranged from 7.2% C, 47.9% S to 16.9% C, 79.7% S.

In a second screening in the fixed bed parallel reactor at 300° C. with different flowrates (ethane:nitrogen:oxygen of 0.42:0.23:0.061 sccm), ethane conversion values for the NiNbCu oxide compositions ranged from 7.4% (with ethylene selectivity of 48.2%) to 16.9% (with ethylene selectivity of 83.2%), and ethylene selectivity values ranged from 48.2% (with ethane conversion of 7.4%) to 83.6% (with ethane conversion of 16.2%).

In a third screening in the fixed bed parallel reactor at 300° C. with different flowrates (ethane:nitrogen:oxygen of 0.42:0.082:0.022 sccm), ethane conversion (C) and ethylene selectivity (S) values for the NiNbCu oxide compositions ranged from 4.1% C, 54.6% S to 10.2% C, 91.4% S.

TABLE 14A

Catalyst compositions (mole fraction) of NiNbCu Oxide Catalysts and sample mass, "m" (mg) used in parallel fixed bed reactor screen.

| | | Col | | | | | |
|---|---|---|---|---|---|---|---|
| Row | | 1 | 2 | 3 | 4 | 5 | 6 |
| 1 | Ni | 0.8574 | 0.7923 | 0.7263 | 0.6594 | 0.5915 | 0.5226 |
| | Nb | 0.1426 | 0.2077 | 0.2737 | 0.3406 | 0.4085 | 0.4774 |
| | Cu | 0.0000 | 0.0000 | 0.0000 | 0.0000 | 0.0000 | 0.0000 |
| | m | 49.8 | 50.7 | 50.7 | 49.3 | 50.2 | 49.7 |

TABLE 14A-continued

Catalyst compositions (mole fraction) of NiNbCu Oxide Catalysts and sample mass, "m" (mg) used in parallel fixed bed reactor screen.

| | | Col | | | | | |
|---|---|---|---|---|---|---|---|
| Row | | 1 | 2 | 3 | 4 | 5 | 6 |
| 2 | Ni | 0.8530 | 0.7882 | 0.7226 | 0.6559 | 0.5884 | 0.5198 |
| | Nb | 0.1419 | 0.2066 | 0.2723 | 0.3388 | 0.4064 | 0.4749 |
| | Cu | 0.0051 | 0.0052 | 0.0052 | 0.0052 | 0.0053 | 0.0053 |
| | m | 50.9 | 49.5 | 50.5 | 50.8 | 50.7 | 49.4 |
| 3 | Ni | 0.8487 | 0.7842 | 0.7188 | 0.6525 | 0.5853 | 0.5171 |
| | Nb | 0.1412 | 0.2056 | 0.2709 | 0.3371 | 0.4042 | 0.4724 |
| | Cu | 0.0102 | 0.0103 | 0.0103 | 0.0104 | 0.0105 | 0.0105 |
| | m | 49.2 | 50.0 | 50.3 | 49.6 | 49.8 | 50.7 |
| 4 | Ni | 0.8444 | 0.7802 | 0.7151 | 0.6492 | 0.5822 | 0.5144 |
| | Nb | 0.1404 | 0.2045 | 0.2695 | 0.3353 | 0.4021 | 0.4699 |
| | Cu | 0.0152 | 0.0153 | 0.0154 | 0.0155 | 0.0156 | 0.0157 |
| | m | 50.6 | 49.4 | 50.0 | 50.9 | 50.0 | 50.7 |
| 5 | Ni | 0.8401 | 0.7762 | 0.7115 | 0.6458 | 0.5792 | 0.5117 |
| | Nb | 0.1397 | 0.2035 | 0.2681 | 0.3336 | 0.4000 | 0.4674 |
| | Cu | 0.0202 | 0.0203 | 0.0204 | 0.0206 | 0.0207 | 0.0209 |
| | m | 50.8 | 50.4 | 50.3 | 50.0 | 49.9 | 50.4 |
| 6 | Ni | 0.8359 | 0.7723 | 0.7079 | 0.6425 | 0.5762 | 0.5090 |
| | Nb | 0.1390 | 0.2024 | 0.2667 | 0.3319 | 0.3980 | 0.4650 |
| | Cu | 0.0251 | 0.0252 | 0.0254 | 0.0256 | 0.0258 | 0.0260 |
| | m | 50.0 | 50.4 | 50.6 | 49.8 | 49.9 | 50.4 |

Example 15

ODHE over NiNbCo Oxide Catalysts
(#16365/16512)

Catalyst compositions comprising various NiNbCo oxides were prepared in small (~100 mg) quantities by precipitation substantially as described in connection with Example 1, using cobalt nitrate ([Co]=1.00 M) aqueous stock solution. Table 15A summarizes the composition and amounts of the various catalyst compositions.

In an initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiNbCo oxide compositions ranged from 7.6% (with ethylene selectivity of 80.7%) to 20.6% (with ethylene selectivity of 85.9%), and ethylene selectivity values ranged from 73.1% (with ethane conversion of 14.2%) to 85.9% (with ethane conversion of 20.6%).

In a second screening in the fixed bed parallel reactor at 300° C. with different flowrates (ethane:nitrogen:oxygen of 0.42:0.23:0.061 sccm), ethane conversion values for the NiNbCo oxide compositions ranged from 8.8% (with ethylene selectivity of 81.9%) to 19.9% (with ethylene selectivity of 88.0%), and ethylene selectivity values ranged from 77.6% (with ethane conversion of 14.6%) to 88.0% (with ethane conversion of 19.9%).

In a third screening in the fixed bed parallel reactor at 300° C. with different floodgates (ethane:nitrogen:oxygen of 0.42:0.082:0.022 sccm), ethane conversion values for the NiNbCo oxide compositions ranged from 7.7% (with ethylene selectivity of 89.4%) to 11.8% (with ethylene selectivity of 93.2%), and ethylene selectivity values ranged from 83.0% (with ethane conversion of 8.7%) to 92.9% (with ethane conversion of 11.7

TABLE 15A

Catalyst compositions (mole fraction) of NiNbCo oxide catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 0.8552 | 0.7903 | 0.7245 | 0.6577 | 0.5900 | 0.5212 |
|   | Nb | 0.1422 | 0.2072 | 0.2730 | 0.3397 | 0.4075 | 0.4762 |
|   | Co | 0.0025 | 0.0025 | 0.0026 | 0.0026 | 0.0026 | 0.0026 |
|   | m  | 50.5   | 49.9   | 50.9   | 49.6   | 50.4   | 49.4   |
| 2 | Ni | 0.8515 | 0.7868 | 0.7213 | 0.6547 | 0.5873 | 0.5189 |
|   | Nb | 0.1416 | 0.2062 | 0.2718 | 0.3382 | 0.4056 | 0.4740 |
|   | Co | 0.0069 | 0.0069 | 0.0070 | 0.0070 | 0.0071 | 0.0071 |
|   | m  | 50.4   | 50.1   | 50.8   | 49.8   | 49.4   | 49.1   |
| 3 | Ni | 0.8478 | 0.7834 | 0.7181 | 0.6518 | 0.5847 | 0.5165 |
|   | Nb | 0.1410 | 0.2053 | 0.2706 | 0.3367 | 0.4038 | 0.4718 |
|   | Co | 0.0112 | 0.0113 | 0.0114 | 0.0115 | 0.0115 | 0.0116 |
|   | m  | 50.9   | 50.0   | 50.0   | 50.5   | 49.3   | 49.6   |
| 4 | Ni | 0.8441 | 0.7799 | 0.7149 | 0.6489 | 0.5820 | 0.5142 |
|   | Nb | 0.1404 | 0.2044 | 0.2694 | 0.3352 | 0.4020 | 0.4697 |
|   | Co | 0.0155 | 0.0156 | 0.0157 | 0.0158 | 0.0160 | 0.0161 |
|   | m  | 50.3   | 50.0   | 49.5   | 50.9   | 49.7   | 49.4   |
| 5 | Ni | 0.8404 | 0.7765 | 0.7118 | 0.6461 | 0.5795 | 0.5119 |
|   | Nb | 0.1398 | 0.2035 | 0.2682 | 0.3337 | 0.4002 | 0.4676 |
|   | Co | 0.0198 | 0.0199 | 0.0201 | 0.0202 | 0.0203 | 0.0205 |
|   | m  | 49.3   | 50.8   | 49.9   | 50.7   | 50.4   | 50.3   |

TABLE 16A

Catalyst compositions (mole fraction) of NiNbCr Oxide Catalysts and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 0.8552 | 0.7903 | 0.7245 | 0.6577 | 0.5900 | 0.5212 |
|   | Nb | 0.1422 | 0.2072 | 0.2730 | 0.3397 | 0.4075 | 0.4762 |
|   | Cr | 0.0025 | 0.0025 | 0.0026 | 0.0026 | 0.0026 | 0.0026 |
|   | m  | 50.8   | 50.0   | 49.8   | 49.7   | 50.0   | 49.4   |
| 2 | Ni | 0.8504 | 0.7858 | 0.7203 | 0.6539 | 0.5865 | 0.5182 |
|   | Nb | 0.1414 | 0.2060 | 0.2714 | 0.3378 | 0.4051 | 0.4734 |
|   | Cr | 0.0081 | 0.0082 | 0.0082 | 0.0083 | 0.0084 | 0.0084 |
|   | m  | 50.7   | 50.6   | 50.4   | 50.7   | 50.9   | 50.0   |
| 3 | Ni | 0.8457 | 0.7814 | 0.7162 | 0.6502 | 0.5832 | 0.5152 |
|   | Nb | 0.1407 | 0.2048 | 0.2699 | 0.3359 | 0.4028 | 0.4706 |
|   | Cr | 0.0137 | 0.0138 | 0.0139 | 0.0140 | 0.0141 | 0.0142 |
|   | m  | 50.3   | 49.5   | 50.1   | 49.7   | 50.4   | 50.4   |
| 4 | Ni | 0.8410 | 0.7770 | 0.7122 | 0.6465 | 0.5798 | 0.5122 |
|   | Nb | 0.1399 | 0.2037 | 0.2684 | 0.3339 | 0.4005 | 0.4679 |
|   | Cr | 0.0192 | 0.0193 | 0.0194 | 0.0196 | 0.0197 | 0.0198 |
|   | m  | 50.6   | 50.0   | 49.9   | 49.9   | 49.5   | 50.8   |
| 5 | Ni | 0.8363 | 0.7727 | 0.7082 | 0.6428 | 0.5765 | 0.5093 |
|   | Nb | 0.1391 | 0.2025 | 0.2669 | 0.3321 | 0.3982 | 0.4652 |
|   | Cr | 0.0246 | 0.0248 | 0.0249 | 0.0251 | 0.0253 | 0.0255 |
|   | m  | 50.7   | 49.9   | 50.7   | 50.5   | 50.2   | 49.3   |

Example 16

ODHE over NiNbCr Oxide Catalysts.
(#16373/16513)

Catalyst compositions comprising various NiNbCr oxides were prepared in bulk (~20 g) quantities by precipitation substantially as described in connection with Example 1, using chromium nitrate ([Cr]=1.00 M) aqueous stock solution. Table 16A summarizes the composition and amounts of the various catalyst compositions.

In an initial screening (calcination at 300° C., 8 hours, screening in fixed bed parallel reactor at 300° C. with flowrates of ethane:nitrogen:oxygen of 0.42:0.54:0.088 sccm, as described), ethane conversion values for the NiNbCr oxide compositions ranged from 11.7% (with ethylene selectivity of 71.9%) to 18.1% (with ethylene selectivity of 82.7%), and ethylene selectivity values ranged from 71.5% (with ethane conversion of 13.1%) to 83.8% (with ethane conversion of 17.7%).

In a second screening in the fixed bed parallel reactor at 300° C. with different flowrates (ethane:nitrogen:oxygen of 0.42:0.23:0.061 sccm), ethane conversion values for the NiNbCr oxide compositions ranged from 14.1% (with ethylene selectivity of 80.5%) to 18.6% (with ethylene selectivity of 86.7%), and ethylene selectivity values ranged from 78.8% (with ethane conversion of 15.1%) to 87.0% (with ethane conversion of 18.3%)

In a third screening in the fixed bed parallel reactor at 300° C. with different flowrates (ethane:nitrogen:oxygen of 0.42: 0.082:0.022 sccm), ethane conversion values for the NiNbCr oxide compositions ranged from 8.6% (with ethylene selectivity of 85.0%) to 11.2% (with ethylene selectivity of 90.0%), and ethylene selectivity values ranged from 85.0% (with ethane conversion of 8.6%) to 91.5% (with ethane conversion of 10.9%).

Example 17

ODHE over NiNbGd/NiTaGd Oxide Catalysts
(#13899)

Catalyst compositions comprising various NiNbGd and NiTaGd oxides were prepared in small (~100 mg) quantities by precipitation substantially as described in connection with Example 1, using gadolinium nitrate ([Gd]=1.00 M) aqueous stock solution, and calcining to 320° C. at 5° C./min and maintaining at 320° C. for 8 hours in air. The compositions and amounts of the various catalyst compositions are shown in Table 17A (NiNbGd) and Table 17B (NiTaGd).

The NiNbGd oxide catalysts were screened in the fixed bed parallel reactor for oxidative ethane dehydrogenation at 300° C. with flowrates of ethane:nitrogen:oxygen of 0.42:0.54: 0.088 sccm. Ethane conversion values for the NiNbGd oxide compositions ranged from 4.9% (with ethylene selectivity of 48.2%) to 20.3% (with ethylene selectivity of 83.2%), and ethylene selectivity values ranged from 45.6% (with ethane conversion of 7.2%) to 83.9% (with ethane conversion of 17.6%).

The NiTaGd oxide catalysts were likewise screened in the fixed bed parallel for oxidative ethane dehydrogenation reactor (300° C.; flowrates of ethane:nitrogen:oxygen of 0.42: 0.54:0.088 sccm). Ethane conversion values for the NiTaGd oxide compositions ranged from 8.0% (with ethylene selectivity of 53.4%) to 19.0% (with ethylene selectivity of 84.7%), and ethylene selectivity values ranged from 51.7% (with ethane conversion of 8.3%) to 84.9% (with ethane conversion of 16.2%).

Additional screens of the NiNbGd oxide catalysts were effected at different temperatures (250° C.; ethane:nitrogen: oxygen flow of 0.42:0.54:0.088 sccm) and, in separate experiments, at different flowrates (300° C.; ethane:nitrogen:oxygen flow of 1.05:1.35:0.22 sccm) (data not shown).

TABLE 17A

Catalyst compositions (mole fractions) of NiNbGd oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.896 | | | | | |
| | Nb | 0.104 | | | | | |
| | Gd | 0.000 | | | | | |
| | mass (mg) | 47.3 | | | | | |
| 2 | Ni | 0.815 | 0.820 | | | | |
| | Nb | 0.099 | 0.180 | | | | |
| | Gd | 0.086 | 0.000 | | | | |
| | mass (mg) | 50.8 | 54.7 | | | | |
| 3 | Ni | 0.740 | 0.745 | 0.749 | | | |
| | Nb | 0.095 | 0.173 | 0.251 | | | |
| | Gd | 0.164 | 0.083 | 0.000 | | | |
| | mass (mg) | 52.2 | 49.8 | 46.9 | | | |
| 4 | Ni | 0.671 | 0.675 | 0.679 | 0.683 | | |
| | Nb | 0.092 | 0.166 | 0.241 | 0.317 | | |
| | Gd | 0.237 | 0.159 | 0.080 | 0.000 | | |
| | mass (mg) | 49.6 | 54.9 | 49.7 | 52.8 | | |
| 5 | Ni | 0.608 | 0.611 | 0.615 | 0.618 | 0.622 | |
| | Nb | 0.088 | 0.160 | 0.232 | 0.305 | 0.378 | |
| | Gd | 0.304 | 0.229 | 0.154 | 0.077 | 0.000 | |
| | mass (mg) | 55.2 | 54.0 | 50.5 | 49.7 | 47.0 | |
| 6 | Ni | 0.549 | 0.552 | 0.555 | 0.558 | 0.561 | 0.564 |
| | Nb | 0.085 | 0.154 | 0.223 | 0.293 | 0.364 | 0.436 |
| | Gd | 0.366 | 0.294 | 0.222 | 0.149 | 0.075 | 0.000 |
| | mass (mg) | 50.7 | 50.5 | 50.7 | 51.4 | 52.9 | 45.0 |

TABLE 17B

Catalyst compositions (mole fractions) of NiTaGd oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.879 | | | | | |
| | Ta | 0.121 | | | | | |
| | Gd | 0.000 | | | | | |
| | Mass (mg) | 55.5 | | | | | |
| 2 | Ni | 0.800 | 0.793 | | | | |
| | Ta | 0.116 | 0.207 | | | | |
| | Gd | 0.084 | 0.000 | | | | |
| | Mass (mg) | 50.9 | 51.4 | | | | |
| 3 | Ni | 0.727 | 0.721 | 0.715 | | | |
| | Ta | 0.111 | 0.199 | 0.285 | | | |
| | Gd | 0.162 | 0.080 | 0.000 | | | |
| | Mass (mg) | 55.9 | 51.3 | 46.7 | | | |
| 4 | Ni | 0.660 | 0.655 | 0.649 | 0.644 | | |
| | Ta | 0.107 | 0.191 | 0.274 | 0.356 | | |
| | Gd | 0.233 | 0.154 | 0.076 | 0.000 | | |
| | Mass (mg) | 52.7 | 53.0 | 53.6 | 51.7 | | |
| 5 | Ni | 0.598 | 0.593 | 0.589 | 0.584 | 0.580 | |
| | Ta | 0.103 | 0.184 | 0.264 | 0.343 | 0.420 | |
| | Gd | 0.299 | 0.222 | 0.147 | 0.073 | 0.000 | |
| | Mass (mg) | 55.1 | 47.5 | 54.6 | 50.8 | 45.5 | |
| 6 | Ni | 0.540 | 0.536 | 0.532 | 0.528 | 0.525 | 0.521 |
| | Ta | 0.099 | 0.178 | 0.255 | 0.331 | 0.405 | 0.479 |
| | Gd | 0.360 | 0.286 | 0.213 | 0.141 | 0.070 | 0.000 |
| | Mass (mg) | 49.6 | 51.8 | 51.8 | 52.8 | 55.6 | 48.6 |

Example 18

ODHE over NiNbBi and NiTaBi Oxide Catalysts

Catalyst compositions comprising various NiNbBi and NiTaBi oxides were prepared in small (~100 mg) quantities by precipitation substantially as described in connection with Example 1, using bismuth citrate ([Bi]=0.293 M) aqueous stock solution. The compositions and amounts of the various catalyst compositions are shown in Table 18A (NiNbBi) and Table 18B (NiTaBi).

The NiNbBi oxide catalysts were initially screened in the fixed bed parallel reactor for oxidative ethane dehydrogenation at 300° C. with flowrates of ethane:nitrogen:oxygen of 0.42:0.54:0.088 sccm. Ethane conversion values for the NiNbBi oxide compositions ranged from 13.1% (with ethylene selectivity of 72.9%) to 19.8% (with ethylene selectivity of 84.2%), and ethylene selectivity values ranged from 72.9% (with ethane conversion of 13.1%) to 84.9% (with ethane conversion of 17.5%)

The NiNbBi catalysts were subsequently recalcined to 400° C. (5° C./min to 400° C.; dwell at 400° C. for 8 hours), and then screened in the parallel fixed bed reactor for ethane dehydrogenation under the same reaction conditions as the initial screen (300° C.; ethane:nitrogen:oxygen flow of 0.42:0.54:0.088 sccm). Ethane conversion values for the NiNbBi oxide compositions ranged from 9.9% (with ethylene selectivity of 85.6%) to 14.1% (with ethylene selectivity of 85.2%), and ethylene selectivity values ranged from 74.6% (with ethane conversion of 12.7%) to 86.3% (with ethane conversion of 13.3%)

The recalcined NiNbBi catalysts were screened again in the parallel fixed bed reactor at different flowrates screen (300° C.; ethane:nitrogen:oxygen flow of 0.42:0.081:0.022 sccm). Ethane conversion values for the NiNbBi oxide compositions ranged from 9.5% (with ethylene selectivity of 93.0%) to 10.9% (with ethylene selectivity of 93.4%), and ethylene selectivity values ranged from 89.8% (with ethane conversion of 10.2%) to 93.8% (with ethane conversion of 10.6%).

The NiTaBi oxide catalysts were likewise initially screened in the fixed bed parallel reactor for oxidative ethane dehydrogenation reactor (300° C.; flowrates of ethane:nitrogen:oxygen of 0.42:0.54:0.088 sccm). Ethane conversion values for the NiTaBi oxide compositions ranged from 13.6% (with ethylene selectivity of 82.5%) to 19.1% (with ethylene selectivity of 84.8%), and ethylene selectivity values ranged from 78.9% (with ethane conversion of 13.7%) to 84.8% (with ethane conversion of 19.1%)

The NiTaBi catalysts were subsequently recalcined to 400° C. (5° C./min to 400° C.; dwell at 400° C. for 8 hours), and then screened in the parallel fixed bed reactor for ethane dehydrogenation under the same reaction conditions as the initial screen (300° C.; ethane:nitrogen:oxygen flow of 0.42:

0.54:0.088 sccm). Ethane conversion values for the NiTaBi oxide compositions ranged from 9.4% (with ethylene selectivity of 77.1%) to 13.5% (with ethylene selectivity of 84.3%), and ethylene selectivity values ranged from 74.6% (with ethane conversion of 10.4%) to 86.9% (with ethane conversion of 11.1%).

The recalcined NiTaBi catalysts were screened again in the parallel fixed bed reactor at different flowrates screen (300° C.; ethane:nitrogen:oxygen flow of 0.42:0.081:0.022 sccm). Ethane conversion (C) and ethylene selectivity (S) values for the NiTaBi oxide compositions ranged from 8.6% C, 87.8% S to 11.0% C, 93.6% S.

TABLE 18A

Catalyst compositions (mole fractions) of NiNbBi oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.890 | | | | | |
|  | Nb | 0.110 | | | | | |
|  | Bi | 0.000 | | | | | |
|  | Mass (mg) | 53.9 | | | | | |
| 2 | Ni | 0.879 | 0.810 | | | | |
|  | Nb | 0.115 | 0.190 | | | | |
|  | Bi | 0.007 | 0.000 | | | | |
|  | Mass (mg) | 50.7 | 53.4 | | | | |
| 3 | Ni | 0.867 | 0.796 | 0.736 | | | |
|  | Nb | 0.119 | 0.197 | 0.264 | | | |
|  | Bi | 0.014 | 0.006 | 0.000 | | | |
|  | mass (mg) | 53.0 | 49.2 | 52.9 | | | |
| 4 | Ni | 0.853 | 0.781 | 0.721 | 0.668 | | |
|  | Nb | 0.125 | 0.205 | 0.273 | 0.332 | | |
|  | Bi | 0.022 | 0.013 | 0.006 | 0.000 | | |
|  | mass (mg) | 56.1 | 53.6 | 54.7 | 51.4 | | |
| 5 | Ni | 0.839 | 0.765 | 0.704 | 0.651 | 0.606 | |
|  | Nb | 0.130 | 0.214 | 0.284 | 0.343 | 0.394 | |
|  | Bi | 0.031 | 0.021 | 0.013 | 0.006 | 0.000 | |
|  | mass (mg) | 49.3 | 45.5 | 53.2 | 52.0 | 46.0 | |
| 6 | Ni | 0.824 | 0.748 | 0.685 | 0.632 | 0.587 | 0.547 |
|  | Nb | 0.136 | 0.223 | 0.295 | 0.355 | 0.407 | 0.453 |
|  | Bi | 0.040 | 0.029 | 0.020 | 0.012 | 0.006 | 0.000 |
|  | mass (mg) | 49.7 | 51.1 | 53.9 | 47.0 | 48.2 | 46.9 |

TABLE 18B

Catalyst compositions (mole fractions) of NiTaBi oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.906 | | | | | |
|  | Ta | 0.094 | | | | | |
|  | Bi | 0.000 | | | | | |
|  | mass (mg) | 55.3 | | | | | |
| 2 | Ni | 0.891 | 0.835 | | | | |
|  | Ta | 0.098 | 0.165 | | | | |
|  | Bi | 0.011 | 0.000 | | | | |
|  | mass (mg) | 46.3 | 54.6 | | | | |
| 3 | Ni | 0.876 | 0.819 | 0.769 | | | |
|  | Ta | 0.101 | 0.170 | 0.231 | | | |

TABLE 18B-continued

Catalyst compositions (mole fractions) of NiTaBi oxide catalysts and sample mass (mg) used in parallel fixed bed reactor screen.

| Row | | Column 1 | 2 | 3 | 4 | 5 | 6 |
|---|---|---|---|---|---|---|---|
|  | Bi | 0.023 | 0.011 | 0.000 | | | |
|  | mass (mg) | 48.2 | 53.8 | 55.8 | | | |
| 4 | Ni | 0.859 | 0.801 | 0.751 | 0.706 | | |
|  | Ta | 0.105 | 0.176 | 0.239 | 0.294 | | |
|  | Bi | 0.036 | 0.022 | 0.010 | 0.000 | | |
|  | mass (mg) | 54.5 | 50.7 | 52.6 | 50.9 | | |
| 5 | Ni | 0.841 | 0.783 | 0.731 | 0.687 | 0.647 | |
|  | Ta | 0.109 | 0.183 | 0.247 | 0.303 | 0.353 | |
|  | Bi | 0.049 | 0.034 | 0.021 | 0.010 | 0.000 | |
|  | mass (mg) | 51.9 | 54.2 | 50.0 | 54.0 | 51.1 | |
| 6 | Ni | 0.822 | 0.762 | 0.711 | 0.665 | 0.626 | 0.591 |
|  | Ta | 0.114 | 0.190 | 0.256 | 0.314 | 0.364 | 0.409 |
|  | Bi | 0.064 | 0.048 | 0.033 | 0.021 | 0.010 | 0.000 |
|  | mass (mg) | 52.5 | 48.6 | 51.5 | 48.6 | 51.0 | 50.7 |

Example 19

ODHE over NiNbSb/NiTaSb Oxide Catalysts

Catalyst compositions comprising various NiNbSb and NiTaSb oxides were prepared in small (~100 mg) quantities by precipitation substantially as described in connection with Example 1, using antimony acetate ([Sb]=0.234 M) aqueous stock solution. The compositions and amounts of the various catalyst compositions are shown in Table 19A (NiNbSb) and Table 19B (NiTaSb).

The NiNbSb oxide catalysts were initially screened in the fixed bed parallel reactor for oxidative ethane dehydrogenation at 300° C. with flowrates of ethane:nitrogen:oxygen of 0.42:0.54:0.088 sccm. Ethane conversion (C) and ethylene selectivity (S) values for the NiNbSb oxide compositions ranged from 14.8% C, 67.6% S to 20.9% C, 84.4% S.

The NiNbSb catalysts were screened again in the parallel fixed bed reactor at different flowrates screen (300° C., ethane:nitrogen:oxygen flow of 1.04:1.34:0.22 sccm). Ethane conversion values for the NiNbSb oxide compositions ranged from 11.8% (with ethylene selectivity of 81.1%) to 18.4% (with ethylene selectivity of 84.0%), and ethylene selectivity values ranged from 77.0% (with ethane conversion of 12.6%) to 84.6% (with ethane conversion of 12.7%).

The NiTaSb oxide catalysts were likewise initially screened in the fixed bed parallel reactor for oxidative ethane dehydrogenation reactor (300° C.; flowrates of ethane:nitrogen:oxygen of 0.42:0.54:0.088 sccm). Ethane conversion values for the NiTaSb oxide compositions ranged from 14.5% (with ethylene selectivity of 72.2%) to 18.7% (with ethylene selectivity of 82.1%), and ethylene selectivity values ranged from 72.2% (with ethane conversion of 14.5%) to 83.5% (with ethane conversion of 18.4%).

The NiTaSb catalysts were screened again in the parallel fixed bed reactor at different flow rates screen (300° C.; ethane:nitrogen:oxygen flow of 1.04:1.34:0.22 sccm). Ethane conversion values for the NiTaSb oxide compositions ranged from 10.0% (with ethylene selectivity of 69.5%) to 14.2% (with ethylene selectivity of 80.2%), and ethylene selectivity values ranged from 69.5% (with ethane conversion of 10.0%) to 83.1% (with ethane conversion of 13.4%).

TABLE 19A

Catalyst compositions (mole fractions) of NiNbSb oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.890 | | | | | |
|   | Nb | 0.110 | | | | | |
|   | Sb | 0.000 | | | | | |
|   | Mass (mg) | 51.6 | | | | | |
| 2 | Ni | 0.879 | 0.814 | | | | |
|   | Nb | 0.115 | 0.186 | | | | |
|   | Sb | 0.006 | 0.000 | | | | |
|   | Mass (mg) | 45.0 | 49.8 | | | | |
| 3 | Ni | 0.867 | 0.801 | 0.744 | | | |
|   | Nb | 0.119 | 0.193 | 0.256 | | | |
|   | Sb | 0.014 | 0.006 | 0.000 | | | |
|   | Mass (mg) | 46.1 | 44.5 | 51.3 | | | |
| 4 | Ni | 0.854 | 0.786 | 0.728 | 0.678 | | |
|   | Nb | 0.125 | 0.201 | 0.266 | 0.322 | | |
|   | Sb | 0.021 | 0.013 | 0.006 | 0.000 | | |
|   | Mass (mg) | 51.0 | 53.3 | 46.1 | 48.3 | | |
| 5 | Ni | 0.840 | 0.771 | 0.712 | 0.661 | 0.617 | |
|   | Nb | 0.130 | 0.209 | 0.276 | 0.333 | 0.383 | |
|   | Sb | 0.029 | 0.020 | 0.012 | 0.006 | 0.000 | |
|   | Mass (mg) | 52.7 | 48.9 | 52.9 | 48.0 | 50.9 | |
| 6 | Ni | 0.825 | 0.754 | 0.694 | 0.643 | 0.599 | 0.560 |
|   | Nb | 0.136 | 0.218 | 0.287 | 0.345 | 0.396 | 0.440 |
|   | Sb | 0.039 | 0.028 | 0.019 | 0.012 | 0.006 | 0.000 |
|   | Mass (mg) | 49.7 | 45.9 | 46.6 | 47.3 | 51.4 | 54.8 |

TABLE 19B

Catalyst compositions (mole fractions) of NiTaSb oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.879 | | | | | |
|   | Ta | 0.121 | | | | | |
|   | Sb | 0.000 | | | | | |
|   | Mass (mg) | 51.8 | | | | | |
| 2 | Ni | 0.868 | 0.788 | | | | |
|   | Ta | 0.126 | 0.212 | | | | |
|   | Sb | 0.006 | 0.000 | | | | |
|   | Mass (mg) | 50.3 | 52.2 | | | | |
| 3 | Ni | 0.855 | 0.774 | 0.707 | | | |
|   | Ta | 0.131 | 0.220 | 0.293 | | | |
|   | Sb | 0.013 | 0.006 | 0.000 | | | |
|   | Mass (mg) | 50.0 | 52.4 | 52.0 | | | |
| 4 | Ni | 0.842 | 0.759 | 0.691 | 0.634 | | |
|   | Ta | 0.137 | 0.228 | 0.303 | 0.366 | | |
|   | Sb | 0.021 | 0.013 | 0.006 | 0.000 | | |
|   | Mass (mg) | 51.4 | 51.1 | 50.2 | 50.4 | | |
| 5 | Ni | 0.828 | 0.743 | 0.674 | 0.617 | 0.569 | |
|   | Ta | 0.143 | 0.237 | 0.314 | 0.378 | 0.431 | |
|   | Sb | 0.029 | 0.020 | 0.012 | 0.005 | 0.000 | |
|   | Mass (mg) | 51.7 | 52.2 | 50.3 | 52.1 | 51.8 | |
| 6 | Ni | 0.812 | 0.726 | 0.656 | 0.598 | 0.550 | 0.509 |
|   | Ta | 0.149 | 0.247 | 0.326 | 0.391 | 0.445 | 0.491 |
|   | Sb | 0.038 | 0.027 | 0.018 | 0.011 | 0.005 | 0.000 |
|   | Mass (mg) | 50.0 | 50.3 | 50.5 | 51.6 | 51.5 | 50.3 |

Example 20

ODHE over NiNbSn/NiTaSn Oxide Catalysts. (#16467/#16469)

Catalyst compositions comprising various NiNbSn and NiTaSn oxides were prepared in small (~100 mg) quantities by precipitation substantially as described in connection with Example 1, using tin acetate ([Sn]=0.249 M) aqueous stock solution. The compositions and amounts of the various catalyst compositions are shown in Table 20A (NiNbSn) and Table 20B (NiTaSn).

The NiNbSn oxide catalysts were initially screened in the fixed bed parallel reactor for oxidative ethane dehydrogenation at 300° C. with flowrates of ethane:nitrogen:oxygen of 0.42:0.54:0.088 sccm. Ethane conversion values for the NiNbSn oxide compositions ranged from 15.1% (with ethylene selectivity of 82.0%) to 19.4% (with ethylene selectivity of 84.8%), and ethylene selectivity values ranged from 82.0% (with ethane conversion of 15.1%) to 85.8% (with ethane conversion of 19.2%).

The NiNbSn catalysts were screened again in the parallel fixed bed reactor at different flowrates screen (300° C.; ethane:nitrogen:oxygen flow of 1.04:1.34:0.22 sccm). Ethane conversion values for the NiNbSn oxide compositions ranged from 8.8% (with ethylene selectivity of 80.4%) to 13.3% (with ethylene selectivity of 84.4%), and ethylene selectivity values ranged from 80.4% (with ethane conversion of 8.8%) to 85.9% (with ethane conversion of 12.8%).

In a third screen, the NiNbSn catalysts were screened in the parallel fixed bed reactor at different flowrates screen (300° C.; ethane:nitrogen:oxygen flow of 1.04:0.21:0.055 sccm). Ethane conversion values for the NiNbSn oxide compositions ranged from 8.4% (with ethylene selectivity of 91.8%) to 10.0% (with ethylene selectivity of 93.5%), and ethylene selectivity values ranged from 89.1% (with ethane conversion of 9.8%) to 93.5% (with ethane conversion of 10.0%).

In a fourth screen, the NiNbSn catalysts were screened in the parallel fixed bed reactor at different flowrates screen (300° C.; ethane:nitrogen:oxygen flow of 0.42:0.082:0.022 sccm). Ethane conversion (C) and ethylene selectivity (S) values for the NiNbSn oxide compositions ranged from 8.7% C, 89.8% S to 11.5% C, 93.8% S.

The NiTaSn oxide catalysts were likewise initially screened in the fixed bed parallel for oxidative ethane dehydrogenation reactor (300° C.; flowrates of ethane:nitrogen:oxygen of 0.42:0.54:0.088 sccm). Ethane conversion values for the NiTaSn oxide compositions ranged from 16.6% (with ethylene selectivity of 84.6%) to 20.3% (with ethylene selectivity of 85.6%), and ethylene selectivity values ranged from 84.1% (with ethane conversion of 18.3%) to 85.7% (with ethane conversion of 19.7%).

The NiTaSn catalysts were screened again in the parallel fixed bed reactor at different flowrates screen (300° C.;

ethane:nitrogen:oxygen flow of 1.04:1.34:0.22 sccm). Ethane conversion values for the NiTaSn oxide compositions ranged from 9.0% (with ethylene selectivity of 89.7%) to 11.0% (with ethylene selectivity of 94.1%), and ethylene selectivity values ranged from 88.7% (with ethane conversion of 10.1%) to 94.2% (with ethane conversion of 10.0%).

In a third screen, the NiTaSn catalysts were screened in the parallel fixed bed reactor at a different temperature and at different flowrates screen (275° C.; ethane:nitrogen:oxygen flow of 1.04:0.21:0.055 sccm). Ethane conversion values for the NiTaSn oxide compositions ranged from 6.9% (with ethylene selectivity of 91.8%) to 8.8% (with ethylene selectivity of 93.6%), and ethylene selectivity values ranged from 91.3% (with ethane conversion of 7.7%) to 94.1% (with ethane conversion of 7.7%).

TABLE 20A

Catalyst compositions (mole fractions) of NiNbSn oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.898 | | | | | |
|  | Nb | 0.102 | | | | | |
|  | Sn | 0.000 | | | | | |
|  | Mass (mg) | 47.0 | | | | | |
| 2 | Ni | 0.885 | 0.823 | | | | |
|  | Nb | 0.106 | 0.177 | | | | |
|  | Sn | 0.009 | 0.000 | | | | |
|  | Mass (mg) | 53.6 | 50.4 | | | | |
| 3 | Ni | 0.871 | 0.807 | 0.753 | | | |
|  | Nb | 0.110 | 0.184 | 0.247 | | | |
|  | Sn | 0.019 | 0.009 | 0.000 | | | |
|  | Mass (mg) | 48.3 | 47.0 | 55.0 | | | |
| 4 | Ni | 0.856 | 0.791 | 0.735 | 0.687 | | |
|  | Nb | 0.115 | 0.191 | 0.256 | 0.313 | | |
|  | Sn | 0.030 | 0.018 | 0.009 | 0.000 | | |
|  | Mass (mg) | 52.0 | 54.1 | 52.7 | 51.5 | | |
| 5 | Ni | 0.839 | 0.773 | 0.717 | 0.668 | 0.626 | |
|  | Nb | 0.119 | 0.198 | 0.265 | 0.323 | 0.374 | |
|  | Sn | 0.041 | 0.029 | 0.018 | 0.008 | 0.000 | |
|  | Mass (mg) | 49.2 | 52.1 | 48.0 | 51.5 | 47.8 | |
| 6 | Ni | 0.821 | 0.754 | 0.697 | 0.648 | 0.606 | 0.569 |
|  | Nb | 0.125 | 0.206 | 0.275 | 0.335 | 0.386 | 0.431 |
|  | Sn | 0.054 | 0.040 | 0.028 | 0.017 | 0.008 | 0.000 |
|  | Mass (mg) | 54.5 | 50.2 | 46.4 | 51.9 | 53.2 | 47.8 |

TABLE 20B

Catalyst compositions (mole fractions) of NiTaSn oxide catalysts and sample mass (mg) used in parallel fixed bed reactor screen.

| Row | | Column 1 | 2 | 3 | 4 | 5 | 6 |
|---|---|---|---|---|---|---|---|
| 1 | Ni | 0.885 | | | | | |
|  | Ta | 0.115 | | | | | |
|  | Sn | 0.000 | | | | | |
|  | Mass (mg) | 52.6 | | | | | |
| 2 | Ni | 0.872 | 0.802 | | | | |
|  | Ta | 0.119 | 0.198 | | | | |
|  | Sn | 0.009 | 0.000 | | | | |
|  | mass (mg) | 52.3 | 53.1 | | | | |
| 3 | Ni | 0.857 | 0.787 | 0.727 | | | |
|  | Ta | 0.124 | 0.205 | 0.273 | | | |
|  | Sn | 0.019 | 0.009 | 0.000 | | | |
|  | mass (mg) | 54.1 | 54.5 | 49.0 | | | |
| 4 | Ni | 0.842 | 0.770 | 0.710 | 0.658 | | |
|  | Ta | 0.129 | 0.212 | 0.282 | 0.342 | | |
|  | Sn | 0.029 | 0.018 | 0.008 | 0.000 | | |
|  | mass (mg) | 53.0 | 51.7 | 53.9 | 47.7 | | |
| 5 | Ni | 0.825 | 0.752 | 0.691 | 0.639 | 0.594 | |
|  | Ta | 0.134 | 0.220 | 0.292 | 0.353 | 0.406 | |
|  | Sn | 0.041 | 0.028 | 0.017 | 0.008 | 0.000 | |
|  | mass (mg) | 52.7 | 53.7 | 50.9 | 53.7 | 50.3 | |
| 6 | Ni | 0.807 | 0.733 | 0.671 | 0.619 | 0.574 | 0.536 |
|  | Ta | 0.140 | 0.229 | 0.302 | 0.365 | 0.418 | 0.464 |
|  | Sn | 0.053 | 0.039 | 0.027 | 0.016 | 0.008 | 0.000 |
|  | mass (mg) | 52.0 | 50.4 | 52.7 | 50.9 | 53.0 | 51.8 |

Example 21

ODHE over NiTaCe/NiNbCe/NiNbTaCe Oxide Catalysts. (#12314/#11169/#12080/#12380/#11285)

NiTaCe catalyst compositions were prepared in bulk by precipitation substantially as described in connection with Example 1, using cerium nitrate ([Ce]=1.00 M) aqueous stock solution, and calcining by heating to 350° C. at 2° C./min and maintaining at 350° C. for 8 hours in air. The compositions and amounts of the various NiTaCe catalyst compositions are shown in Table 21A.

The NiTaCe oxide catalysts were screened in the fixed bed parallel reactor for oxidative ethane dehydrogenation at 300° C. with flowrates of ethane:nitrogen:oxygen of 0.42:0.54:0.088 sccm. Ethane conversion values for the NiTaCe oxide compositions ranged from 0.1% (with ethylene selectivity of 59.4%) to 18.1% (with ethylene selectivity of 84.7%), and ethylene selectivity values ranged from 31.9% (with ethane conversion of 2.8%) to 85.4% (with ethane conversion of 16.8%).

TABLE 21A

Catalysts compositions (mole fractions) of NiTaCe and sample mass, "m" (mg) used in parallel fixed bed reactor screen.

| Row | | Col 1 | 2 | 3 | 4 | 5 | 6 |
|---|---|---|---|---|---|---|---|
| 1 | Ni | 0.9681 | 0.8950 | 0.8178 | 0.7362 | 0.6498 | 0.5580 |
|  | Ta | 0.0319 | 0.1050 | 0.1822 | 0.2638 | 0.3502 | 0.4420 |
|  | Ce | 0.0000 | 0.0000 | 0.0000 | 0.0000 | 0.0000 | 0.0000 |
|  | m | 40.8 | 46.6 | 52.6 | 55.3 | 45.2 | 50.8 |
| 2 | Ni | 0.9569 | 0.8844 | 0.8079 | 0.7270 | 0.6414 | 0.5507 |
|  | Ta | 0.0316 | 0.1038 | 0.1800 | 0.2605 | 0.3457 | 0.4361 |
|  | Ce | 0.0115 | 0.0118 | 0.0121 | 0.0125 | 0.0128 | 0.0132 |
|  | m | 46.7 | 47.1 | 50.6 | 52.7 | 51.6 | 56.3 |
| 3 | Ni | 0.9461 | 0.8741 | 0.7982 | 0.7181 | 0.6333 | 0.5435 |
|  | Ta | 0.0312 | 0.1026 | 0.1778 | 0.2573 | 0.3414 | 0.4304 |
|  | Ce | 0.0227 | 0.0233 | 0.0239 | 0.0246 | 0.0253 | 0.0261 |
|  | m | 51.6 | 45.5 | 47.2 | 43.1 | 52.7 | 58.8 |

TABLE 21A-continued

Catalysts compositions (mole fractions) of NiTaCe and sample mass, "m" (mg) used in parallel fixed bed reactor screen.

| Row | | Col 1 | 2 | 3 | 4 | 5 | 6 |
|---|---|---|---|---|---|---|---|
| 4 | Ni | 0.9355 | 0.8641 | 0.7888 | 0.7094 | 0.6254 | 0.5365 |
|   | Ta | 0.0309 | 0.1014 | 0.1757 | 0.2542 | 0.3371 | 0.4249 |
|   | Ce | 0.0337 | 0.0346 | 0.0355 | 0.0365 | 0.0375 | 0.0386 |
|   | m  | 44.1   | 52.2   | 46.3   | 53.3   | 47.6   | 56.9   |
| 5 | Ni | 0.9251 | 0.8542 | 0.7796 | 0.7008 | 0.6177 | 0.5297 |
|   | Ta | 0.0305 | 0.1002 | 0.1737 | 0.2511 | 0.3329 | 0.4195 |
|   | Ce | 0.0444 | 0.0456 | 0.0468 | 0.0481 | 0.0494 | 0.0508 |
|   | m  | 49.2   | 55.7   | 44.1   | 43.0   | 54.1   | 55.6   |
| 6 | Ni | 0.9149 | 0.8446 | 0.7706 | 0.6925 | 0.6101 | 0.5230 |
|   | Ta | 0.0302 | 0.0991 | 0.1716 | 0.2481 | 0.3289 | 0.4142 |
|   | Ce | 0.0549 | 0.0563 | 0.0578 | 0.0594 | 0.0610 | 0.0628 |
|   | m  | 45.6   | 58.1   | 45.5   | 45     | 58.4   | 55.1   |

NiNbCe catalyst compositions were prepared by several different methods, including freeze drying, precipitation with tetraethylammonium hydroxide, and precipitation with ammonium carbonate, and then screened as discussed below. Briefly, in the freeze drying method, NiNbCe catalyst compositions were prepared by combining various amounts of the aqueous metal salt solutions to form a catalyst precursor solution, and then freeze drying to remove water. The NiNbCe catalyst compositions prepared by precipitation with tetraethylammonium hydroxide were prepared substantially as described in Example 1, using cerium nitrate ([Ce]=1.00 M), and using tetraethylammonium hydroxide as the precipitating agent. In each of these two cases, the resulting solid materials were calcined by heating to 120° C. at 1° C./min and dwelling at 120° C. for 2 hours, subsequently, heating to 180° C. at 1° C./min and dwelling at 180° C. for 2 hours, subsequently heating to 400° C. at 2° C./min and dwelling at 400° C. for 8 hours. The NiTbCe catalyst compositions prepared by precipitation with ammonium carbonate were prepared substantially as described in Example 1, using cerium nitrate ([Ce]=1.00 M), and using ammonium carbonate as the precipitating agent. In this cases, the resulting solid material was calcined by heating to 300° C. at 2° C./min and dwelling at 300° C. for 8 hours in air. The compositions and amounts of the various NiNbCe catalyst compositions are shown in Table 21B (prepared by freeze drying), Table 21C (prepared by precipitation with tetraethylammonium hydroxide) and Table 21D (prepared by precipitation with ammonium carbonate).

The NiNbCe catalysts of Table 21B—prepared by freeze drying—were screened in the fixed bed parallel reactor for oxidative ethane dehydrogenation at 300° C. with flowrates of ethane:nitrogen:oxygen of 0.42:0.54:0.088 sccm. Ethane conversion values for the NiNbCe oxide compositions ranged from 6.6% (with ethylene selectivity of 61.8%) to 11.7% (with ethylene selectivity of 71.6%), and ethylene selectivity values ranged from 61.3% (with ethane conversion of 8.5%) to 74.3% (with ethane conversion of 10.5%).

The NiNbCe catalysts of Table 21C—prepared by precipitation with tetraethylammonium hydroxide—were likewise screened in the fixed bed parallel reactor for oxidative ethane dehydrogenation at 300° C. with flowrates of ethane:nitrogen:oxygen of 0.42:0.54:0.088 sccm. Ethane conversion values for the NiNbCe oxide compositions ranged from 7.5% (with ethylene selectivity of 78.8%) to 18.8% (with ethylene selectivity of 85.7%), and ethylene selectivity values ranged from 58.9% (with ethane conversion of 10.1%) to 85.7% (with ethane conversion of 18.8%). These catalysts were also screened in the parallel fixed bed reactor at different flowrates (300° C.; ethane:nitrogen:oxygen flow of 0.10:0.85:0.088 sccm) (data not shown).

The NiNbCe catalysts of Table 21D—prepared by precipitation with ammonium carbonate—were likewise screened in the fixed bed parallel reactor for oxidative ethane dehydrogenation at 300° C. with flowrates of ethane:nitrogen:oxygen of 0.42:0.54:0.088 sccm. Ethane conversion values for the NiNbCe oxide compositions ranged from 16.7% (with ethylene selectivity of 78.1%) to 19.1% (with ethylene selectivity of 81.5%), and ethylene selectivity values ranged from 78.1% (with ethane conversion of 16.7%) to 83.5% (with ethane conversion of 18.5%). These catalysts were also screened in an ethylene co-feed (mixed feed) experiment (data not shown). These catalysts were also screened again after being recalcined by heating to 400° C. at 2° C./min and dwelling at 400° C. for 8 hours in air. (data not shown).

TABLE 21B

Catalyst compositions (mole fractions) of NiNbCe oxide catalysts prepared by freeze drying and sample mass (mg) used in parallel fixed bed reactor screen.

| Row | | Column 1 | 2 | 3 | 4 | 5 | 6 | 7 |
|---|---|---|---|---|---|---|---|---|
| 1 | Ni | 0.907 | | | | | | |
|   | Nb | 0.068 | | | | | | |
|   | Ce | 0.024 | | | | | | |
|   | Mass (mg) | 41.5 | | | | | | |
| 2 | Ni | 0.860 | 0.850 | | | | | |
|   | Nb | 0.069 | 0.126 | | | | | |
|   | Ce | 0.070 | 0.025 | | | | | |
|   | Mass (mg) | 44.9 | 39.7 | | | | | |
| 3 | Ni | 0.812 | 0.802 | 0.792 | | | | |
|   | Nb | 0.071 | 0.128 | 0.183 | | | | |
|   | Ce | 0.118 | 0.071 | 0.025 | | | | |
|   | Mass (mg) | 43.1 | 40.4 | 37.4 | | | | |
| 4 | Ni | 0.762 | 0.752 | 0.743 | 0.734 | | | |
|   | Nb | 0.072 | 0.130 | 0.186 | 0.242 | | | |
|   | Ce | 0.166 | 0.118 | 0.071 | 0.025 | | | |
|   | Mass (mg) | 44.2 | 39.7 | 38.7 | 38.0 | | | |
| 5 | Ni | 0.710 | 0.701 | 0.692 | 0.684 | 0.675 | | |
|   | Nb | 0.073 | 0.132 | 0.189 | 0.246 | 0.300 | | |

TABLE 21B-continued

Catalyst compositions (mole fractions) of NiNbCe oxide catalysts prepared by freeze drying and sample mass (mg) used in parallel fixed bed reactor screen.

| Row | | Column 1 | 2 | 3 | 4 | 5 | 6 | 7 |
|---|---|---|---|---|---|---|---|---|
| | Ce | 0.217 | 0.167 | 0.118 | 0.071 | 0.025 | | |
| | Mass (mg) | 39.3 | 43.1 | 37.8 | 43.6 | 39.7 | | |
| 6 | Ni | 0.657 | 0.648 | 0.640 | 0.632 | 0.624 | 0.616 | |
| | Nb | 0.074 | 0.134 | 0.193 | 0.250 | 0.305 | 0.359 | |
| | Ce | 0.269 | 0.218 | 0.168 | 0.119 | 0.071 | 0.025 | |
| | Mass (mg) | 40.8 | 52.7 | 36.6 | 37.9 | 39.1 | 38.7 | |
| 7 | Ni | 0.601 | 0.593 | 0.586 | 0.578 | 0.571 | 0.563 | 0.556 |
| | Nb | 0.075 | 0.137 | 0.196 | 0.254 | 0.310 | 0.365 | 0.419 |
| | Ce | 0.323 | 0.270 | 0.219 | 0.168 | 0.119 | 0.072 | 0.025 |
| | Mass (mg) | 42.3 | 38.7 | 44.9 | 35.1 | 35.8 | 37.4 | 36.1 |

TABLE 21C

Catalyst compositions (mole fractions) of NiNbCe oxide catalysts prepared by precipitation with tetraethylammonium hydroxide and sample mass (mg) used in parallel fixed bed reactor screen.

| Row | | Column 1 | 2 | 3 | 4 | 5 | 6 |
|---|---|---|---|---|---|---|---|
| 1 | Ni | 0.942 | | | | | |
| | Nb | 0.058 | | | | | |
| | Ce | 0.000 | | | | | |
| | Mass (mg) | 52.7 | | | | | |
| 2 | Ni | 0.921 | 0.870 | | | | |
| | Nb | 0.060 | 0.131 | | | | |
| | Ce | 0.019 | 0.000 | | | | |
| | Mass (mg) | 43.6 | 42.7 | | | | |
| 3 | Ni | 0.898 | 0.847 | 0.801 | | | |
| | Nb | 0.062 | 0.134 | 0.199 | | | |
| | Ce | 0.040 | 0.019 | 0.000 | | | |
| | Mass (mg) | 46.4 | 53.1 | 51.3 | | | |
| 4 | Ni | 0.875 | 0.823 | 0.778 | 0.737 | | |
| | Nb | 0.064 | 0.138 | 0.204 | 0.263 | | |
| | Ce | 0.062 | 0.039 | 0.018 | 0.000 | | |
| | Mass (mg) | 54.0 | 50.7 | 49.8 | 51.2 | | |
| 5 | Ni | 0.849 | 0.798 | 0.752 | 0.712 | 0.675 | |
| | Nb | 0.066 | 0.142 | 0.210 | 0.270 | 0.325 | |
| | Ce | 0.085 | 0.060 | 0.038 | 0.018 | 0.000 | |
| | Mass (mg) | 48.0 | 52.9 | 52.1 | 49.2 | 52.9 | |
| 6 | Ni | 0.822 | 0.771 | 0.726 | 0.686 | 0.650 | 0.617 |
| | Nb | 0.068 | 0.147 | 0.216 | 0.278 | 0.333 | 0.383 |
| | Ce | 0.110 | 0.082 | 0.058 | 0.037 | 0.017 | 0.000 |
| | Mass (mg) | 51.0 | 45.2 | 49.9 | 45.3 | 48.7 | 50.2 |

TABLE 21D

Catalyst compositions (mole fractions) of NiNbCe oxide catalysts prepared by precipitation with ammonium carbonate and sample mass (mg) used in parallel fixed bed reactor screen.

| Row | | Column 1 | 2 | 3 | 4 | 5 | 6 |
|---|---|---|---|---|---|---|---|
| 1 | Ni | 0.890 | | | | | |
| | Nb | 0.110 | | | | | |
| | Ce | 0.000 | | | | | |
| | mass (mg) | 48.5 | | | | | |
| 2 | Ni | 0.879 | 0.810 | | | | |
| | Nb | 0.115 | 0.190 | | | | |
| | Ce | 0.007 | 0.000 | | | | |
| | mass (mg) | 48.1 | 49.0 | | | | |
| 3 | Ni | 0.867 | 0.796 | 0.736 | | | |
| | Nb | 0.119 | 0.198 | 0.264 | | | |
| | Ce | 0.014 | 0.006 | 0.000 | | | |
| | mass (mg) | 55.2 | 46.2 | 51.6 | | | |
| 4 | Ni | 0.854 | 0.782 | 0.721 | 0.668 | | |
| | Nb | 0.125 | 0.205 | 0.273 | 0.332 | | |
| | Ce | 0.022 | 0.013 | 0.006 | 0.000 | | |
| | mass (mg) | 51.0 | 51.5 | 54.7 | 47.9 | | |
| 5 | Ni | 0.840 | 0.766 | 0.704 | 0.651 | 0.606 | |
| | Nb | 0.130 | 0.214 | 0.284 | 0.343 | 0.394 | |
| | Ce | 0.030 | 0.021 | 0.013 | 0.006 | 0.000 | |
| | mass (mg) | 51.9 | 54.4 | 51.4 | 54.4 | 53.4 | |
| 6 | Ni | 0.824 | 0.749 | 0.686 | 0.632 | 0.587 | 0.547 |
| | Nb | 0.136 | 0.223 | 0.295 | 0.356 | 0.408 | 0.453 |
| | Ce | 0.039 | 0.029 | 0.020 | 0.012 | 0.006 | 0.000 |
| | mass (mg) | 45.4 | 52.7 | 49.1 | 49.0 | 47.8 | 52.8 |

NiNbTaCe catalyst compositions were prepared in bulk by precipitation substantially as described in connection with Example 1, using cerium nitrate ([Ce]=1.00 M) aqueous stock solution, and calcining by heating to 350° C. at 2° C./min and maintaining at 350° C. for 8 hours in air. The compositions and amounts of the various NiTaCe catalyst compositions are shown in Table 21E.

The NiNbTaCe oxide catalysts were initially screened in the fixed bed parallel reactor for oxidative ethane dehydrogenation at 300° C. with flowrates of ethane:nitrogen:oxygen of 0.42:0.54:0.088 sccm. Ethane conversion values for the NiNbTaCe oxide compositions ranged from 16.8% (with ethylene selectivity of 83.4%) to 20.8% (with ethylene selectivity of 84.0%), and ethylene selectivity values ranged from 81.6% (with ethane conversion of 17.9%) to 84.0% (with ethane conversion of 20.8%).

The NiNbTaCe oxide catalysts were screened again in the fixed bed parallel reactor for oxidative ethane dehydrogenation at twice the flowrates as compared to the initial screen (300° C.; ethane:nitrogen:oxygen flow of 0.84:1.08:0.176 sccm). Ethane conversion values for the NiNbTaCe oxide compositions ranged from 11.6% (with ethylene selectivity of 83.2%) to 16.6% (with ethylene selectivity of 84.2%), and ethylene selectivity values ranged from 80.0% (with ethane conversion of 12.7%) to 84.3% (with ethane conversion of 15.5%).

Table 21E. Catalyst compositions (mole fractions) of NiNbTaCe oxide catalysts and sample mass (mg) used in parallel fixed bed reactor screen.

TABLE 21E

| Row | | Column 1 | 2 | 3 | 4 | 5 | 6 | 7 | 8 |
|---|---|---|---|---|---|---|---|---|---|
| | | Part A | | | | | | | |
| 1 | Ni | 0.988 | | | | | | | |
| | Nb | 0.000 | | | | | | | |
| | Ta | 0.000 | | | | | | | |
| | Ce | 0.012 | | | | | | | |
| | mass (mg) | 49.2 | | | | | | | |
| 2 | Ni | 0.899 | 0.904 | | | | | | |
| | Nb | 0.000 | 0.085 | | | | | | |
| | Ta | 0.090 | 0.000 | | | | | | |
| | Ce | 0.011 | 0.012 | | | | | | |
| | mass (mg) | 45.3 | 47.5 | | | | | | |
| 3 | Ni | 0.815 | 0.820 | 0.824 | | | | | |
| | Nb | 0.000 | 0.082 | 0.165 | | | | | |
| | Ta | 0.174 | 0.087 | 0.000 | | | | | |
| | Ce | 0.011 | 0.011 | 0.011 | | | | | |
| | mass (mg) | 52.8 | 53.5 | 47.4 | | | | | |
| 4 | Ni | 0.738 | 0.741 | 0.745 | 0.749 | | | | |
| | Nb | 0.000 | 0.079 | 0.159 | 0.240 | | | | |
| | Ta | 0.252 | 0.169 | 0.085 | 0.000 | | | | |
| | Ce | 0.011 | 0.011 | 0.011 | 0.011 | | | | |
| | mass (mg) | 52.3 | 51.7 | 51.4 | 51.4 | | | | |
| 5 | Ni | 0.665 | 0.668 | 0.671 | 0.675 | 0.678 | | | |
| | Nb | 0.000 | 0.077 | 0.154 | 0.232 | 0.311 | | | |
| | Ta | 0.325 | 0.245 | 0.164 | 0.083 | 0.000 | | | |
| | Ce | 0.010 | 0.010 | 0.010 | 0.011 | 0.011 | | | |
| | mass (mg) | 53.1 | 53.0 | 53.8 | 50.2 | 45.1 | | | |
| 6 | Ni | 0.596 | 0.599 | 0.602 | 0.605 | 0.608 | 0.611 | | |
| | Nb | 0.000 | 0.074 | 0.149 | 0.225 | 0.302 | 0.379 | | |
| | Ta | 0.394 | 0.316 | 0.238 | 0.160 | 0.080 | 0.000 | | |
| | Ce | 0.010 | 0.010 | 0.010 | 0.010 | 0.010 | 0.010 | | |
| | mass (mg) | 55.2 | 47.8 | 51.3 | 48.9 | 47.1 | 49.7 | | |
| 7 | Ni | 0.532 | 0.535 | 0.537 | 0.540 | 0.542 | 0.545 | 0.547 | |
| | Nb | 0.000 | 0.072 | 0.145 | 0.218 | 0.292 | 0.367 | 0.443 | |
| | Ta | 0.458 | 0.384 | 0.308 | 0.232 | 0.156 | 0.078 | 0.000 | |
| | Ce | 0.010 | 0.010 | 0.010 | 0.010 | 0.010 | 0.010 | 0.010 | |
| | mass (mg) | 52.5 | 50.1 | 48.8 | 45.8 | 55.1 | 53.0 | 47.5 | |
| 8 | Ni | 0.472 | 0.474 | 0.476 | 0.478 | 0.480 | 0.483 | 0.485 | 0.487 |
| | Nb | 0.000 | 0.070 | 0.141 | 0.212 | 0.284 | 0.356 | 0.429 | 0.503 |
| | Ta | 0.519 | 0.447 | 0.374 | 0.301 | 0.226 | 0.152 | 0.076 | 0.000 |
| | Ce | 0.009 | 0.010 | 0.010 | 0.010 | 0.010 | 0.010 | 0.010 | 0.010 |
| | mass (mg) | 53.8 | 53.0 | 45.7 | 45.0 | 49.5 | 48.9 | 52.0 | 46.5 |

Example 22

ODHE over NiTaYb/NiNbYb Oxide Catalysts. (#13947/#13946)

Catalyst compositions comprising various NiTaY and NiNbYb oxides were prepared in small (~100 mg) quantities by precipitation substantially as described in connection with Example 1, using ytterbium nitrate pentahydrate ([Yb]=0.456M) aqueous stock solution and calcining at 300° C., as described. The compositions and amounts of the various catalyst compositions are shown in Table 22A (NiTaYb) and Table 22B (NiNbYb).

The NiTaYb oxide catalysts were screened in the fixed bed parallel reactor for oxidative ethane dehydrogenation at 300° C. with flowrates of ethane:nitrogen:oxygen of 0.42:0.54:0.088 sccm. Ethane conversion values for the NiTaYb oxide compositions ranged from 13.5% (with ethylene selectivity of 75.1%) to 20.0% (with ethylene selectivity of 83.9%), and ethylene selectivity values ranged from 75.1% (with ethane conversion of 13.5%) to 84.7% (with ethane conversion of 19.1%).

The NiNbYb oxide catalysts were likewise screened in the fixed bed parallel reactor for oxidative ethane dehydrogenation at 300° C. with flowrates of ethane:nitrogen:oxygen of 0.42:0.54:0.088 sccm. Ethane conversion values for the NiNbYb oxide compositions ranged from 10.5% (with ethylene selectivity of 68.8%) to 19.4% (with ethylene selectivity of 83.0%), and ethylene selectivity values ranged from 68.8% (with ethane conversion of 10.5%) to 84.0% (with ethane conversion of 18.3%).

TABLE 22A

Catalyst compositions (mole fractions) of NiTaYb oxide catalysts and sample mass (mg) used in parallel fixed bed reactor screen.

| Row | Column | 1 | 2 | 3 | 4 | 5 | 6 |
|---|---|---|---|---|---|---|---|
| 1 | Ni | 0.879 | | | | | |
| | Ta | 0.121 | | | | | |
| | Yb | 0.000 | | | | | |
| | mass (mg) | 51.2 | | | | | |
| 2 | Ni | 0.855 | 0.793 | | | | |
| | Ta | 0.124 | 0.207 | | | | |
| | Yb | 0.021 | 0.000 | | | | |
| | mass (mg) | 53.9 | 51.0 | | | | |
| 3 | Ni | 0.831 | 0.768 | 0.715 | | | |
| | Ta | 0.127 | 0.212 | 0.285 | | | |
| | Yb | 0.042 | 0.019 | 0.000 | | | |
| | mass (mg) | 51.0 | 54.0 | 54.6 | | | |
| 4 | Ni | 0.805 | 0.743 | 0.690 | 0.644 | | |
| | Ta | 0.131 | 0.217 | 0.291 | 0.356 | | |
| | Yb | 0.065 | 0.040 | 0.019 | 0.000 | | |
| | mass (mg) | 49.5 | 52.6 | 53.2 | 50.5 | | |
| 5 | Ni | 0.777 | 0.716 | 0.664 | 0.619 | 0.580 | |
| | Ta | 0.134 | 0.222 | 0.298 | 0.363 | 0.420 | |
| | Yb | 0.089 | 0.061 | 0.038 | 0.018 | 0.000 | |
| | mass (mg) | 49.4 | 47.9 | 50.8 | 52.7 | 47.8 | |
| 6 | Ni | 0.749 | 0.688 | 0.637 | 0.593 | 0.555 | 0.521 |
| | Ta | 0.138 | 0.228 | 0.305 | 0.371 | 0.429 | 0.479 |
| | Yb | 0.114 | 0.084 | 0.058 | 0.036 | 0.017 | 0.000 |
| | mass (mg) | 51.6 | 54.0 | 53.4 | 53.3 | 52.5 | 53.1 |

TABLE 22B

Catalyst compositions (mole fractions) of NiNbYb oxide catalysts and sample mass (mg) used in parallel fixed bed reactor screen.

| Row | Column | 1 | 2 | 3 | 4 | 5 | 6 |
|---|---|---|---|---|---|---|---|
| 1 | Ni | 0.896 | | | | | |
|   | Nb | 0.104 | | | | | |
|   | Yb | 0.000 | | | | | |
|   | mass (mg) | 51.8 | | | | | |
| 2 | Ni | 0.873 | 0.820 | | | | |
|   | Nb | 0.107 | 0.180 | | | | |
|   | Yb | 0.021 | 0.000 | | | | |
|   | mass (mg) | 49.0 | 54.5 | | | | |
| 3 | Ni | 0.848 | 0.795 | 0.749 | | | |
|   | Nb | 0.109 | 0.185 | 0.251 | | | |
|   | Yb | 0.043 | 0.020 | 0.000 | | | |
|   | mass (mg) | 53.7 | 48.8 | 45.9 | | | |
| 4 | Ni | 0.822 | 0.770 | 0.724 | 0.683 | | |
|   | Nb | 0.112 | 0.189 | 0.257 | 0.317 | | |
|   | Yb | 0.066 | 0.041 | 0.019 | 0.000 | | |
|   | mass (mg) | 52.5 | 52.2 | 46.2 | 52.4 | | |
| 5 | Ni | 0.794 | 0.743 | 0.697 | 0.657 | 0.622 | |
|   | Nb | 0.115 | 0.194 | 0.263 | 0.324 | 0.378 | |
|   | Yb | 0.091 | 0.063 | 0.040 | 0.019 | 0.000 | |
|   | mass (mg) | 52.0 | 49.1 | 48.3 | 52.2 | 53.4 | |
| 6 | Ni | 0.765 | 0.714 | 0.670 | 0.630 | 0.595 | 0.564 |
|   | Nb | 0.118 | 0.199 | 0.269 | 0.331 | 0.387 | 0.436 |
|   | Yb | 0.116 | 0.087 | 0.061 | 0.038 | 0.018 | 0.000 |
|   | mass (mg) | 49.9 | 51.8 | 48.9 | 46.8 | 54.8 | 47.6 |

Example 23

ODHE over NiTaEr/NiNbEr Oxide Catalysts. (#13950)

Catalyst compositions comprising various NiTaEr and NiNbEr oxides were prepared in small (~100 mg) quantities by precipitation substantially as described in connection with Example 1, using erbium acetate hydrate ([Er]=0.268 M) aqueous stock solution and calcining at 300° C., as described. The compositions and amounts of the various NiTaEr and NiNbEr oxide catalyst compositions are shown in Table 23A.

The NiTaEr and NiNbEr oxide catalysts (~50 mg) were screened in the fixed bed parallel reactor for oxidative ethane dehydrogenation at 300° C. with flowrates of ethane:nitrogen:oxygen of 0.42:0.54:0.088 sccm. Ethane conversion values for the NiTaEr oxide compositions ranged from 12.9% (with ethylene selectivity of 69.7%) to 19.4% (with ethylene selectivity of 83.5%), and ethylene selectivity values ranged from 69.7% (with ethane conversion of 12.9%) to 84.1% (with ethane conversion of 17.9%). Ethane conversion values for the NiNbEr oxide compositions ranged from 12.5% (with ethylene selectivity of 65.0%) to 20.9% (with ethylene selectivity of 83.9%), and ethylene selectivity values ranged from 65.0% (with ethane conversion of 12.5%) to 85.0% (with ethane conversion of 18.2%).

The NiTaEr and NiNbEr oxide catalysts (~50 mg) were screened again in the fixed bed parallel reactor for oxidative ethane dehydrogenation at a different temperature (250° C.; ethane:nitrogen:oxygen flow of 0.42:0.54:0.088 sccm). Ethane conversion values for the NiTaEr oxide compositions ranged from 3.6% (with ethylene selectivity of 55.1%) to 7.8% (with ethylene selectivity of 65.0%), and ethylene selectivity values ranged from 55.1% (with ethane conversion of 3.6%) to 76.6% (with ethane conversion of 7.1%). Ethane conversion values for the NiNbEr oxide compositions ranged from 3.5% (with ethylene selectivity of 44.3%) to 7.4% (with ethylene selectivity of 74.4%), and ethylene selectivity values ranged from 44.3% (with ethane conversion of 3.5%) to 83.6% (with ethane conversion of 6.6%).

TABLE 23A

Catalyst compositions (mole fractions) of NiTaEr/NiNbEr oxide catalysts used in parallel fixed bed reactor screen.

| Row | Col | 1 | 2 | 3 | 4 | 5 | 6 |
|---|---|---|---|---|---|---|---|
| 1 | Ni | 1.000 | 0.919 | 0.842 | 0.768 | 0.696 | 0.628 |
|   | Nb | 0.000 | 0.000 | 0.000 | 0.000 | 0.000 | 0.000 |
|   | Ta | 0.000 | 0.081 | 0.158 | 0.232 | 0.304 | 0.372 |
|   | Er | 0.000 | 0.000 | 0.000 | 0.000 | 0.000 | 0.000 |
| 2 | Ni | 0.915 | 0.967 | 0.884 | 0.806 | 0.730 | 0.658 |
|   | Nb | 0.085 | 0.000 | 0.000 | 0.000 | 0.000 | 0.000 |
|   | Ta | 0.000 | 0.000 | 0.083 | 0.163 | 0.239 | 0.311 |
|   | Er | 0.000 | 0.033 | 0.032 | 0.032 | 0.031 | 0.030 |
| 3 | Ni | 0.835 | 0.881 | 0.932 | 0.848 | 0.768 | 0.691 |
|   | Nb | 0.165 | 0.087 | 0.000 | 0.000 | 0.000 | 0.000 |
|   | Ta | 0.000 | 0.000 | 0.000 | 0.086 | 0.167 | 0.245 |
|   | Er | 0.000 | 0.032 | 0.068 | 0.067 | 0.065 | 0.064 |
| 4 | Ni | 0.759 | 0.799 | 0.844 | 0.895 | 0.809 | 0.728 |
|   | Nb | 0.241 | 0.170 | 0.090 | 0.000 | 0.000 | 0.000 |
|   | Ta | 0.000 | 0.000 | 0.000 | 0.000 | 0.088 | 0.172 |
|   | Er | 0.000 | 0.031 | 0.066 | 0.105 | 0.103 | 0.100 |
| 5 | Ni | 0.686 | 0.722 | 0.761 | 0.806 | 0.855 | 0.768 |
|   | Nb | 0.314 | 0.248 | 0.174 | 0.092 | 0.000 | 0.000 |
|   | Ta | 0.000 | 0.000 | 0.000 | 0.000 | 0.000 | 0.091 |
|   | Er | 0.000 | 0.031 | 0.064 | 0.102 | 0.145 | 0.141 |
| 6 | Ni | 0.617 | 0.648 | 0.683 | 0.721 | 0.764 | 0.813 |
|   | Nb | 0.383 | 0.322 | 0.255 | 0.179 | 0.095 | 0.000 |
|   | Ta | 0.000 | 0.000 | 0.000 | 0.000 | 0.000 | 0.000 |
|   | Er | 0.000 | 0.030 | 0.063 | 0.099 | 0.140 | 0.187 |

Example 24

ODHE over NiTaDy/NiNbDy Oxide Catalysts. (#13949)

Catalyst compositions comprising various NiTaDy and NiNbDy oxides were prepared in small (~100 mg) quantities by precipitation substantially as described in connection with Example 1, using dysprosium acetate hydrate ([Dy]=0.294 M) aqueous stock solution and calcining at 300° C., as described. The compositions and amounts of the various NiTaDy and NiNbDy oxide catalyst compositions are shown in Table 24A.

The NiTaDy and NiNbDy oxide catalysts (~50 mg) were screened in the fixed bed parallel reactor for oxidative ethane dehydrogenation at 300° C. with flowrates of ethane:nitrogen:oxygen of 0.42:0.54:0.088 sccm. Ethane conversion values for the NiTaDy oxide compositions ranged from 14.1% (with ethylene selectivity of 71.2%) to 19.9% (with ethylene selectivity of 84.4%), and ethylene selectivity values ranged from 71.2% (with ethane conversion of 14.1%) to 84.7% (with ethane conversion of 17.3%). Ethane conversion values for the NiNbDy oxide compositions ranged from 10.9% (with ethylene selectivity of 63.1%) to 18.9% (with ethylene selectivity of 82.7%), and ethylene selectivity values ranged from 63.1% (with ethane conversion of 10.9%) to 84.7% (with ethane conversion of 18.4%).

The NiTaDy and NiNbDy oxide catalysts (50 mg) were screened again in the fixed bed parallel reactor for oxidative ethane dehydrogenation at a different temperature (250° C.; ethane:nitrogen:oxygen flow of 0.42:0.54:0.088 sccm). (data not shown). These catalysts were also further calcined at 400%, and then screened again, in separate experiments, at 250° C. and at 300° C., in each case with ethane:nitrogen:oxygen flow of 0.42:0.54:0.088 sccm. (data not shown).

TABLE 24A

Catalyst compositions (mole fractions) of NiTaDy/NiNbDy oxide catalysts used in parallel fixed bed reactor screen.

| Row | Col | 1 | 2 | 3 | 4 | 5 | 6 |
|---|---|---|---|---|---|---|---|
| 1 | Ni | 1.000 | 0.919 | 0.842 | 0.768 | 0.696 | 0.628 |
|   | Nb | 0.000 | 0.000 | 0.000 | 0.000 | 0.000 | 0.000 |
|   | Ta | 0.000 | 0.081 | 0.158 | 0.232 | 0.304 | 0.372 |
|   | Dy | 0.000 | 0.000 | 0.000 | 0.000 | 0.000 | 0.000 |
| 2 | Ni | 0.915 | 0.964 | 0.882 | 0.803 | 0.728 | 0.656 |
|   | Nb | 0.085 | 0.000 | 0.000 | 0.000 | 0.000 | 0.000 |
|   | Ta | 0.000 | 0.000 | 0.083 | 0.162 | 0.238 | 0.311 |
|   | Dy | 0.000 | 0.036 | 0.035 | 0.035 | 0.034 | 0.033 |
| 3 | Ni | 0.835 | 0.878 | 0.926 | 0.842 | 0.763 | 0.687 |
|   | Nb | 0.165 | 0.087 | 0.000 | 0.000 | 0.000 | 0.000 |
|   | Ta | 0.000 | 0.000 | 0.000 | 0.085 | 0.166 | 0.244 |
|   | Dy | 0.000 | 0.035 | 0.074 | 0.072 | 0.071 | 0.069 |
| 4 | Ni | 0.759 | 0.797 | 0.839 | 0.886 | 0.801 | 0.721 |
|   | Nb | 0.241 | 0.169 | 0.089 | 0.000 | 0.000 | 0.000 |
|   | Ta | 0.000 | 0.000 | 0.000 | 0.000 | 0.087 | 0.170 |
|   | Dy | 0.000 | 0.034 | 0.072 | 0.114 | 0.112 | 0.109 |
| 5 | Ni | 0.686 | 0.720 | 0.757 | 0.798 | 0.843 | 0.758 |
|   | Nb | 0.314 | 0.247 | 0.173 | 0.091 | 0.000 | 0.000 |
|   | Ta | 0.000 | 0.000 | 0.000 | 0.000 | 0.000 | 0.090 |
|   | Dy | 0.000 | 0.033 | 0.070 | 0.111 | 0.157 | 0.153 |
| 6 | Ni | 0.617 | 0.646 | 0.679 | 0.714 | 0.754 | 0.799 |
|   | Nb | 0.383 | 0.321 | 0.253 | 0.178 | 0.094 | 0.000 |
|   | Ta | 0.000 | 0.000 | 0.000 | 0.000 | 0.000 | 0.000 |
|   | Dy | 0.000 | 0.033 | 0.068 | 0.108 | 0.152 | 0.201 |

Example 25

ODHE over NiNbSr/NiNbCs Oxide Catalysts. (# 16892)

Catalyst compositions comprising various NiNbSr and NiNbCs oxides were prepared in small (~100 mg) quantities dispensing various amounts of aqueous metal solutions (nickel nitrate ([Ni]=1.0M), niobium oxalate ([Nb]=0.569M, excess oxalic acid [H$^+$]=0.346M), strontium nitrate ([Sr]=1.0M), and cesium nitrate ([Cs]=1.00M) with an automated liquid handling robot into an array of glass vials in an aluminum substrate. Magnetic stirbars were added to each of the glass vials, and the precursor solutions were heated at 120° C. on a hot place with vigorous magnetic stirring, such that the water in the solutions boiled off after about 2 hours. The dried materials were then calcined by heating to 320° C. at 5° C./min and are dwelling at 320° C. for 8 hours in air, and subsequently cooled to 25° C. The compositions and amounts of the various NiNbSr and NiNbCs oxide catalyst compositions are shown in Table 25A.

The NiNbSr and NiNbCs oxide catalysts (~50 mg) were screened in the fixed bed parallel reactor for oxidative ethane dehydrogenation at 300° C. with flowrates of ethane:oxygen of 0.42:0.058 sccm. Ethane conversion values for the NiNbSr oxide compositions ranged from 17.4% (with ethylene selectivity of 84.4%) to 22.0% (with ethylene selectivity of 87.5%), and ethylene selectivity values ranged from 82.3% (with ethane conversion of 18.1%) to 89.6% (with ethane conversion of 21.2%). Ethane conversion (C) and ethylene selectivity (S) values for the NiNbCs oxide compositions ranged from 5.2% C, 15.2% S to 21.7% C, 87.5% S.

The NiNbSr and NiNbCs oxide catalysts (~50 mg) were screened again in the fixed bed parallel reactor for oxidative ethane dehydrogenation at a different temperature and different flowrates (275° C.; ethane:oxygen flow of 0.42:0.033 sccm). Ethane conversion values for the NiNbSr oxide compositions ranged from 10.6% (with ethylene selectivity of 84.5%) to 15.5% (with ethylene selectivity of 91.4%), and ethylene selectivity values ranged from 83.7% (with ethane conversion of 11.2%) to 91.4% (with ethane conversion of 15.5%). Ethane conversion (C) and ethylene selectivity (S) values for the NiNbCs oxide compositions ranged from 3.3% C, 14.4% S to 14.4% C, 90.1% S.

TABLE 25A

Catalyst compositions (mole fractions) of NiNbSr/NiNbCs oxide catalysts used in parallel fixed bed reactor screen.

| Row | Column | 1 | 2 | 3 | 4 | 5 | 6 |
|---|---|---|---|---|---|---|---|
| 1 | Ni | 0.898 | 0.883 | 0.867 | 0.850 | 0.832 | 0.812 |
|   | Nb | 0.102 | 0.106 | 0.110 | 0.114 | 0.118 | 0.123 |
|   | Sr | 0.000 | 0.000 | 0.000 | 0.000 | 0.000 | 0.000 |
|   | Cs | 0.000 | 0.011 | 0.023 | 0.036 | 0.050 | 0.065 |
|   | mass (mg) | 51.2 | 51.5 | 51.4 | 50.0 | 48.3 | 54.2 |
| 2 | Ni | 0.883 | 0.823 | 0.806 | 0.788 | 0.769 | 0.748 |
|   | Nb | 0.106 | 0.177 | 0.183 | 0.190 | 0.197 | 0.204 |
|   | Sr | 0.011 | 0.000 | 0.000 | 0.000 | 0.000 | 0.000 |
|   | Cs | 0.000 | 0.000 | 0.011 | 0.022 | 0.035 | 0.048 |
|   | mass (mg) | 53.2 | 50.1 | 50.9 | 51.8 | 51.3 | 47.5 |
| 3 | Ni | 0.867 | 0.806 | 0.753 | 0.734 | 0.714 | 0.693 |
|   | Nb | 0.110 | 0.183 | 0.247 | 0.256 | 0.264 | 0.273 |
|   | Sr | 0.023 | 0.011 | 0.000 | 0.000 | 0.000 | 0.000 |
|   | Cs | 0.000 | 0.000 | 0.000 | 0.010 | 0.021 | 0.033 |
|   | mass (mg) | 52.4 | 52.1 | 51.6 | 49.500 | 48.300 | 51.100 |
| 4 | Ni | 0.850 | 0.788 | 0.734 | 0.687 | 0.667 | 0.646 |
|   | Nb | 0.114 | 0.190 | 0.256 | 0.313 | 0.323 | 0.333 |
|   | Sr | 0.036 | 0.022 | 0.010 | 0.000 | 0.000 | 0.000 |
|   | Cs | 0.000 | 0.000 | 0.000 | 0.000 | 0.010 | 0.021 |
|   | mass (mg) | 52.2 | 50.6 | 53.8 | 51.5 | 52.300 | 54.400 |
| 5 | Ni | 0.832 | 0.769 | 0.714 | 0.667 | 0.626 | 0.605 |
|   | Nb | 0.118 | 0.197 | 0.264 | 0.323 | 0.374 | 0.385 |
|   | Sr | 0.050 | 0.035 | 0.021 | 0.010 | 0.000 | 0.000 |
|   | Cs | 0.000 | 0.000 | 0.000 | 0.000 | 0.000 | 0.010 |
|   | mass (mg) | 46.4 | 51.1 | 49.2 | 51.5 | 49.9 | 54.200 |
| 6 | Ni | 0.812 | 0.748 | 0.693 | 0.646 | 0.605 | 0.569 |
|   | Nb | 0.123 | 0.204 | 0.273 | 0.333 | 0.385 | 0.431 |
|   | Sr | 0.065 | 0.048 | 0.033 | 0.021 | 0.010 | 0.000 |
|   | Cs | 0.000 | 0.000 | 0.000 | 0.000 | 0.000 | 0.000 |
|   | mass (mg) | 52.3 | 53.6 | 50.0 | 48.8 | 50.5 | 54.4 |

Example 26

Lifetime Tests for ODHE over Ni(Nb, Ta, Ti, Zr)-based Oxide Catalysts

In a first set of experiments, long-term stability and performance characteristics of various Ni(Nb, Ta, Ti, Zr)(Ce, Dy, Er, Nd, Sm, Yb, Pr, Gd, Sb, Bi) oxide catalysts were evaluated in a 200 hour lifetime test. In a second set of experiments, long-term stability and performance characteristics of various Ni(Nb, Ta, Ti)(Sm, Sn, Co, Cs, Sb, Ag)(Mg, Ca, Li) oxide catalysts were evaluated in a 400 hour lifetime test. As described below, compositions and preparation methods were varied in the lifetime tests. Test conditions were, in the 200 hour test, also varied (data not shown).

200 Hour Lifetime Test

In the 200 hour lifetime test, forty-two different Ni(Nb, Ta, Ti, Zr)(Ce, Dy, Er, Nd, Sm, Yb, Pr, Gd, Sb, Bi) oxide catalysts were prepared according to one of the following methods, designated as Method A through Method F. The various catalyst compositions and their method of preparation are shown in Table 26A.

Method A: Catalysts were prepared by precipitation with tetramethylammonium hydroxide to the mixed metal nitrate or oxalate solution. After centrifugation, the solid materials obtained were dried at 60° C. under vacuum, and then calcined to 300° C. at 2° C./min and dwelled at 300° C. for 8 hrs.

Method B: Catalysts were prepared by precipitation with tetramethylammonium hydroxide to the mixed metal nitrate or oxalate solution. After centrifugation, the solid materials obtained were dried at 60° C. under vacuum, and then calcined to 300° C. at 2° C./min and dwelled at 300° C. for 8 hrs. After cooling down to 25 CC, those catalysts were calcined again to 400° C. at 2° C./min and dwell at 400° C. for 8 hrs.

Method C: Catalysts were prepared by precipitation with ammonium carbonate to the mixed metal nitrate or oxalate solution. After centrifugation, the solid materials obtained were dried at 60° C. under vacuum, and then calcined to 300° C. at 2° C./min and dwelled at 300° C. for 8 hrs.

Method D: Catalysts were prepared by precipitation with ammonium carbonate to the mixed metal nitrate or oxalate solution. After centrifugation, the solid materials obtained were dried at 60° C. under vacuum, and then calcined to 300° C. at 2° C./min and dwelled at 300° C. for 8 hrs. After cooling down to 25° C., those catalysts were calcined again to 400° C. at 2° C./min and dwell at 400° C. for 8 hrs.

Method E: $TiO_2$ support in pellet form was dried at 100° C. for over 8 hrs. After cooling to 25° C., $TiO_2$ support was impregnated with the mixed metal nitrate or oxalate solution. After centrifugation, the solid materials obtained were dried at 60° C. under vacuum, and then calcined to 300° C. at 2° C./min and dwelled at 300° C. for 8 hrs.

Method F: Catalysts were prepared by precipitation with tetramethylammonium hydroxide to the mixed metal nitrate or oxalate solution. After centrifugation, the solid materials obtained are dried at 60° C. under vacuum, and then calcined to 400° C. at 2° C./min and dwelled at 400° C. for 8 hrs.

The forty-two catalysts of Table 26A (~50 mg), together with six blanks, were screened simulanteously in the 48-channel parallel fixed bed reactor for oxidative ethane dehydrogenation at 300° C. with ethane:nitrogen:oxygen flow of 0.42:0.54:0.088 sccm. Table 26B summarizes the amount of catalyst screened, as well as the ethane conversion (C) and ethylene selectivity (S) for each of the catalysts, measured after various times during the test.

Table 26A: Catalyst composition and preparation methods for catalysts screened in 200 hour lifetime test.

TABLE 26A

Catalyst composition and preparation methods for catalysts screened in 200 hour lifetime test.

| Catalyst Composition | Preparation Method |
|---|---|
| $Ni_{0.86}Ta_{0.14}O_x$ | A |
| $Ni_{0.65}Ta_{0.31}Ce_{0.04}O_x$ | A |
| $Ni_{0.62}Nb_{0.19}Ta_{0.19}Ce_{0.01}O_x$ | A |
| $Ni_{0.73}Ta_{0.24}Dy_{0.03}O_x$ | A |
| $Ni_{0.68}Nb_{0.25}Dy_{0.07}O_x$ | A |
| $Ni_{0.68}Nb_{0.26}Er_{0.06}O_x$ | A |
| Blank | n/a |
| $Ni_{0.62}Nb_{0.38}O_x$ | A |
| $Ni_{0.71}Ta_{0.23}Nd_{0.06}O_x$ | A |
| $Ni_{0.63}Nb_{0.34}Sm_{0.03}O_x$ | A |
| $Ni_{0.54}Ta_{0.45}Sm_{0.01}O_x$ | A |
| $Ni_{0.72}Ti_{0.28}O_x$ | A |
| $Ni_{0.66}Ti_{0.29}Yb_{0.05}O_x$ | A |
| blank | n/a |
| $Ni_{0.62}Nb_{0.34}Ce_{0.04}O_x$ | B |
| $Ni_{0.62}Ta_{0.34}Ce_{0.04}O_x$ | B |
| $Ni_{0.76}Nb_{0.17}Er_{0.06}O_x$ | B |
| $Ni_{0.68}Ta_{0.25}Dy_{0.07}O_x$ | B |
| $Ni_{0.60}Nb_{0.19}Ta_{0.18}Sm_{0.03}O_x$ | B |
| $Ni_{0.64}Nb_{0.34}Pr_{0.02}O_x$ | B |
| blank | n/a |
| $Ni_{0.63}Nb_{0.37}O_x$ | B |
| $Ni_{0.51}Ta_{0.42}Zr_{0.07}O_x$ | B |
| $Ni_{0.73}Ti_{0.27}O_x$ | B |
| $Ni_{0.58}Ta_{0.34}Gd_{0.07}O_x$ | B |
| $Ni_{0.68}Nb_{0.24}Gd_{0.08}O_x$ | B |
| $Ni_{0.80}Nb_{0.19}Sb_{0.01}O_x$ | B |
| blank | n/a |
| $Ni_{0.82}Nb_{0.14}Sb_{0.04}O_x$ | B |
| $Ni_{0.60}Nb_{0.39}Sb_{0.01}O_x$ | A |
| $Ni_{0.72}Nb_{0.27}Bi_{0.01}O_x$ | B |
| $Ni_{0.73}Ta_{0.25}Bi_{0.02}O_x$ | B |
| $Ni_{0.63}Nb_{0.33}Yb_{0.04}O_x$ | B |
| $Ni_{0.59}Ta_{0.37}Yb_{0.04}O_x$ | B |
| blank | n/a |
| $Ni_{0.65}Nb_{0.33}Ce_{0.02}O_x$ | C |
| $Ni_{0.71}Nb_{0.27}Sb_{0.02}O_x$ | C |
| $Ni_{0.65}Nb_{0.33}Ce_{0.02}O_x$ | D |
| $Ni_{0.63}Nb_{0.19}Ta_{0.18}O_x/TiO_2$ | E |
| $Ni_{0.71}Nb_{0.27}Sb_{0.02}O_x$ | D |
| $Ni_{0.65}Nb_{0.33}Ce_{0.02}O_x$ | F |
| blank | n/a |
| $Ni_{0.74}Nb_{0.08}Ta_{0.17}Ce_{0.01}O_x$ | F |
| $Ni_{0.75}Nb_{0.24}Ce_{0.01}O_x$ | F |
| $Ni_{0.53}Ta_{0.40}Gd_{0.07}O_x$ | A |
| $Ni_{0.74}Nb_{0.08}Ta_{0.17}Ce_{0.01}O_x$ | A |
| $Ni_{0.74}Ta_{0.22}Yb_{0.04}O_x$ | A |
| $Ni_{0.65}Ta_{0.36}Bi_{0.01}O_x$ | A |

TABLE 26B

Catalyst composition, sample mass (mg) and ethane conversion (C) and ethylene selectivity (S) measured at various times on stream during screening in 200 hour lifetime test.

| | | Time on stream hour | | | |
|---|---|---|---|---|---|
| | Mass | 5.34 | | 62.37 | |
| Library | (mg) | C (%) | S (%) | C (%) | S (%) |
| | | Part A1 | | | |
| $Ni_{0.86}Ta_{0.14}O_x$ | 49.4 | 18.1 | 83.5 | 18.2 | 83.3 |
| $Ni_{0.65}Ta_{0.31}Ce_{0.04}O_x$ | 50 | 17.8 | 82.4 | 18.5 | 82.8 |
| $Ni_{0.62}Nb_{0.19}Ta_{0.19}Ce_{0.01}O_x$ | 50.4 | 16.4 | 84.3 | 14.3 | 84.6 |
| $Ni_{0.73}Ta_{0.24}Dy_{0.03}O_x$ | 50.5 | 19.1 | 83.8 | 18.9 | 84.2 |
| $Ni_{0.68}Nb_{0.25}Dy_{0.07}O_x$ | 49.8 | 18.6 | 83.6 | 18.9 | 83.6 |
| $Ni_{0.68}Nb_{0.26}Er_{0.06}O_x$ | 49.8 | 19.0 | 83.0 | 18.1 | 83.1 |

TABLE 26B-continued

| | | | | | |
|---|---|---|---|---|---|
| Blank | n/a | 0.1 | 46.0 | 0.1 | 46.7 |
| $Ni_{0.62}Nb_{0.38}O_x$ | 49.2 | 19.6 | 85.2 | 18.2 | 85.5 |
| $Ni_{0.71}Ta_{0.23}Nd_{0.06}O_x$ | 49.6 | 17.3 | 81.5 | 17.0 | 81.8 |
| $Ni_{0.63}Th_{0.34}Sm_{0.03}O_x$ | 50.4 | 21.1 | 85.0 | 20.3 | 85.2 |
| $Ni_{0.54}Ta_{0.45}Sm_{0.01}O_x$ | 49.5 | 17.4 | 84.5 | 16.2 | 84.2 |
| $Ni_{0.72}Ti_{0.28}O_x$ | 50 | 18.7 | 85.0 | 18.3 | 85.5 |
| $Ni_{0.66}Ti_{0.29}Yb_{0.05}O_x$ | 49.5 | 17.5 | 82.6 | 17.5 | 81.4 |
| blank | n/a | 0.1 | 45.6 | 0.1 | 45.2 |
| $Ni_{0.62}Nb_{0.34}Ce_{0.04}O_x$ | 42.6 | 15.7 | 81.0 | 14.9 | 81.8 |
| $Ni_{0.62}Ta_{0.34}Ce_{0.04}O_x$ | 47.6 | 14.7 | 81.7 | 14.9 | 82.3 |
| $Ni_{0.76}Nb_{0.17}Er_{0.06}O_x$ | 45 | 13.4 | 84.8 | 12.6 | 84.7 |
| $Ni_{0.68}Ta_{0.25}Dy_{0.07}O_x$ | 44.2 | 13.2 | 83.3 | 11.9 | 83.2 |
| $Ni_{0.60}Nb_{0.19}Ta_{0.18}Sm_{0.03}O_x$ | 45.6 | 15.3 | 84.2 | 14.8 | 83.4 |
| $Ni_{0.64}Nb_{0.34}Pr_{0.02}O_x$ | 48.1 | 15.5 | 84.6 | 14.6 | 83.9 |
| blank | n/a | 0.1 | 44.3 | 0.1 | 42.6 |
| $Ni_{0.63}Nb_{0.37}O_x$ | 45.9 | 12.8 | 86.4 | 11.5 | 86.3 |
| $Ni_{0.51}Ta_{0.42}Zr_{0.07}O_x$ | 44.5 | 15.0 | 83.3 | 13.9 | 82.6 |
| $Ni_{0.73}Ti_{0.27}O_x$ | 45.8 | 12.6 | 83.7 | 11.2 | 83.5 |
| $Ni_{0.58}Ta_{0.34}Gd_{0.07}O_x$ | 45.6 | 10.4 | 83.5 | 9.4 | 83.2 |
| $Ni_{0.68}Nb_{0.24}Gd_{0.08}O_x$ | 55.2 | 14.0 | 79.5 | 13.2 | 78.0 |
| $Ni_{0.80}Nb_{0.19}Sb_{0.01}O_x$ | 48.6 | 14.0 | 85.6 | 12.4 | 85.5 |
| blank | n/a | 0.1 | 38.5 | 0.1 | 37.9 |
| $Ni_{0.82}Nb_{0.14}Sb_{0.04}O_x$ | 49.6 | 12.0 | 83.7 | 10.2 | 82.7 |
| $Ni_{0.60}Nb_{0.39}Sb_{0.01}O_x$ | 51.8 | 17.9 | 83.9 | 16.5 | 83.7 |
| $Ni_{0.72}Nb_{0.27}Bi_{0.01}O_x$ | 54.7 | 15.4 | 85.9 | 15.1 | 85.8 |
| $Ni_{0.73}Ta_{0.25}Bi_{0.02}O_x$ | 50 | 10.9 | 86.0 | 10.2 | 85.9 |
| $Ni_{0.63}Nb_{0.33}Yb_{0.04}O_x$ | 41.1 | 13.9 | 83.3 | 12.7 | 82.7 |
| $Ni_{0.59}Ta_{0.37}Yb_{0.04}O_x$ | 47.1 | 10.8 | 84.9 | 7.2 | 85.1 |
| blank | n/a | 0.1 | 40.0 | 0.1 | 48.2 |
| $Ni_{0.65}Nb_{0.33}Ce_{0.02}O_x$ | 48.3 | 16.5 | 82.6 | 15.4 | 79.8 |
| $Ni_{0.71}Nb_{0.27}Sb_{0.02}O_x$ | 49.1 | 16.5 | 82.6 | 14.9 | 77.8 |
| | | Part A2 | | | |
| $Ni_{0.65}Nb_{0.33}Ce_{0.02}O_x$ | 49.3 | 13.0 | 82.5 | 12.5 | 80.4 |
| $Ni_{0.63}Nb_{0.19}Ta_{0.18}O_x/TiO_2$ | 145.9 | 7.9 | 89.1 | 5.9 | 89.8 |
| $Ni_{0.71}Nb_{0.27}Sb_{0.02}O_x$ | 51.5 | 11.2 | 81.5 | 8.8 | 77.6 |
| $Ni_{0.65}Nb_{0.23}Ce_{0.02}O_x$ | 49.7 | 16.7 | 85.2 | 16.2 | 85.1 |
| blank | n/a | 0.1 | 37.4 | 0.1 | 43.1 |
| $Ni_{0.74}Nb_{0.08}Ta_{0.17}Ce_{0.01}O_x$ | 50 | 16.1 | 84.3 | 16.8 | 84.9 |
| $Ni_{0.75}Nb_{0.24}Ce_{0.01}O_x$ | 50.2 | 19.4 | 85.8 | 19.1 | 86.4 |
| $Ni_{0.53}Ta_{0.40}Gd_{0.07}O_x$ | 48.9 | 16.8 | 78.8 | 16.2 | 77.4 |
| $Ni_{0.74}Nb_{0.08}Ta_{0.17}Ce_{0.01}O_x$ | 50.9 | 17.3 | 84.3 | 15.6 | 85.0 |
| $Ni_{0.74}Ta_{0.22}Yb_{0.04}O_x$ | 50.7 | 17.8 | 84.2 | 17.5 | 84.6 |
| $Ni_{0.65}Ta_{0.36}Bi_{0.01}O_x$ | 50.4 | 16.3 | 82.6 | 15.3 | 82.1 |

| | 108.24 | | 189.3 | | 207.98 | |
|---|---|---|---|---|---|---|
| Library # | C (%) | S (%) | C (%) | S (%) | C (%) | S (%) |
| | | Part B1 | | | | |
| $Ni_{0.86}Ta_{0.14}O_x$ | 17.0 | 83.2 | 17.4 | 83.1 | 18.0 | 83.1 |
| $Ni_{0.65}Ta_{0.31}Ce_{0.04}O_x$ | 17.8 | 82.5 | 16.6 | 82.0 | 17.8 | 82.1 |
| $Ni_{0.62}Nb_{0.19}Ta_{0.19}Ce_{0.01}O_x$ | 13.3 | 84.6 | 11.8 | 84.2 | 12.8 | 84.6 |
| $Ni_{0.73}Ta_{0.24}Dy_{0.03}O_x$ | 18.4 | 84.2 | 18.0 | 84.0 | 18.7 | 84.2 |
| $Ni_{0.68}Nb_{0.25}Dy_{0.07}O_x$ | 18.1 | 83.5 | 17.6 | 82.9 | 18.1 | 82.9 |
| $Ni_{0.68}Nb_{0.26}Er_{0.06}O_x$ | 17.9 | 83.0 | 17.2 | 82.4 | 18.2 | 82.3 |
| Blank | 0.1 | 48.3 | 0.1 | 44.1 | 0.1 | 45.3 |
| $Ni_{0.62}Nb_{0.38}O_x$ | 17.5 | 85.1 | 16.3 | 84.7 | 16.9 | 84.9 |
| $Ni_{0.71}Ta_{0.23}Nd_{0.06}O_x$ | 16.4 | 81.4 | 16.3 | 81.4 | 16.7 | 81.3 |
| $Ni_{0.63}Nb_{0.34}Sm_{0.03}O_x$ | 19.4 | 85.0 | 18.8 | 84.5 | 17.3 | 84.5 |
| $Ni_{0.54}Ta_{0.45}Sm_{0.01}O_x$ | 15.3 | 83.9 | 14.5 | 83.5 | 14.8 | 83.6 |
| $Ni_{0.72}Ti_{0.28}O_x$ | 17.7 | 85.2 | 17.4 | 85.1 | 17.4 | 85.0 |
| $Ni_{0.66}Ti_{0.29}Yb_{0.05}O_x$ | 17.0 | 80.5 | 16.5 | 79.1 | 15.6 | 79.0 |
| blank | 0.1 | 43.8 | 0.1 | 42.2 | 0.1 | 39.9 |
| $Ni_{0.62}Nb_{0.34}Ce_{0.04}O_x$ | 14.7 | 81.6 | 14.5 | 81.5 | 14.4 | 81.5 |
| $Ni_{0.62}Ta_{0.34}Ce_{0.04}O_x$ | 13.9 | 82.3 | 13.2 | 82.2 | 12.7 | 82.1 |
| $Ni_{0.76}Nb_{0.17}Er_{0.06}O_x$ | 11.4 | 84.5 | 11.5 | 84.3 | 11.4 | 84.2 |
| $Ni_{0.68}Ta_{0.25}Dy_{0.07}O_x$ | 11.8 | 82.7 | 11.7 | 82.3 | 11.8 | 82.4 |
| $Ni_{0.60}Nb_{0.19}Ta_{0.18}Sm_{0.03}O_x$ | 14.1 | 82.8 | 13.7 | 82.2 | 13.7 | 82.4 |
| $Ni_{0.64}Nb_{0.34}Pr_{0.02}O_x$ | 13.7 | 82.9 | 12.7 | 81.0 | 12.8 | 81.4 |
| blank | 0.1 | 44.0 | 0.1 | 43.2 | 0.1 | 44.8 |
| $Ni_{0.63}Nb_{0.37}O_x$ | 10.4 | 86.1 | 9.9 | 85.3 | 10.1 | 85.6 |
| $Ni_{0.51}Ta_{0.42}Zr_{0.07}O_x$ | 12.9 | 82.3 | 12.5 | 82.0 | 12.6 | 82.1 |
| $Ni_{0.73}Ti_{0.27}O_x$ | 10.6 | 83.7 | 10.1 | 83.7 | 9.6 | 83.6 |
| $Ni_{0.58}Ta_{0.34}Gd_{0.07}O_x$ | 9.0 | 83.1 | 8.5 | 82.5 | 8.5 | 82.7 |
| $Ni_{0.68}Nb_{0.24}Gd_{0.08}O_x$ | 12.5 | 76.5 | 11.6 | 74.0 | 11.7 | 74.6 |
| $Ni_{0.80}Nb_{0.19}Sb_{0.01}O_x$ | 11.9 | 85.5 | 11.2 | 85.0 | 11.1 | 85.3 |

TABLE 26B-continued

| | Part B2 | | | | | |
|---|---|---|---|---|---|---|
| blank | 0.1 | 40.0 | 0.1 | 40.6 | 0.1 | 41.1 |
| $Ni_{0.82}Nb_{0.14}Sb_{0.04}O_x$ | 9.5 | 82.3 | 8.6 | 81.0 | 8.9 | 81.7 |
| $Ni_{0.60}Nb_{0.39}Sb_{0.01}O_x$ | 16.0 | 83.4 | 15.4 | 82.9 | 15.5 | 83.2 |
| $Ni_{0.72}Nb_{0.27}Bi_{0.01}O_x$ | 14.4 | 85.9 | 13.6 | 85.2 | 14.1 | 85.5 |
| $Ni_{0.73}Ta_{0.25}Bi_{0.02}O_x$ | 9.8 | 85.7 | 8.9 | 85.5 | 9.3 | 85.7 |
| $Ni_{0.63}Nb_{0.33}Yb_{0.04}O_x$ | 12.6 | 82.2 | 10.8 | 80.4 | 12.0 | 81.3 |
| $Ni_{0.59}Ta_{0.37}Yb_{0.04}O_x$ | 6.2 | 85.1 | 5.4 | 85.0 | 5.9 | 85.0 |
| blank | 0.1 | 48.6 | 0.1 | 47.5 | 0.1 | 47.1 |
| $Ni_{0.65}Nb_{0.33}Ce_{0.02}O_x$ | 14.6 | 78.1 | 12.7 | 72.3 | 13.5 | 73.6 |
| $Ni_{0.71}Nb_{0.27}Sb_{0.02}O_x$ | 14.2 | 73.4 | 11.4 | 62.3 | 12.3 | 64.8 |
| $Ni_{0.65}Nb_{0.33}Ce_{0.02}O_x$ | 12.4 | 78.4 | 10.2 | 70.3 | 10.8 | 73.1 |
| $Ni_{0.63}Nb_{0.19}Ta_{0.18}O_x/TiO_2$ | 6.1 | 89.0 | 4.9 | 89.2 | 5.3 | 89.2 |
| $Ni_{0.71}Nb_{0.27}Sb_{0.02}O_x$ | 9.6 | 76.8 | 7.9 | 71.4 | 8.8 | 74.1 |
| $Ni_{0.65}Nb_{0.33}Ce_{0.02}O_x$ | 17.0 | 85.6 | 16.0 | 85.4 | 17.6 | 85.9 |
| blank | 0.1 | 47.9 | 0.1 | 47.3 | 0.1 | 47.8 |
| $Ni_{0.74}Nb_{0.08}Ta_{0.17}Ce_{0.01}O_x$ | 15.7 | 84.7 | 15.3 | 84.3 | 15.5 | 84.2 |
| $Ni_{0.75}Nb_{0.24}Ce_{0.01}O_x$ | 18.6 | 86.3 | 18.2 | 86.1 | 18.4 | 86.3 |
| $Ni_{0.53}Ta_{0.40}Gd_{0.07}O_x$ | 16.1 | 77.3 | 14.7 | 74.4 | 15.0 | 75.2 |
| $Ni_{0.74}Nb_{0.08}Ta_{0.17}Ce_{0.01}O_x$ | 16.0 | 85.3 | 14.3 | 84.8 | 14.8 | 83.5 |
| $Ni_{0.74}Ta_{0.22}Yb_{0.04}O_x$ | 17.8 | 85.1 | 16.6 | 84.7 | 17.4 | 84.9 |
| $Ni_{0.65}Ta_{0.36}Bi_{0.01}O_x$ | 14.9 | 82.9 | 12.6 | 83.0 | 14.4 | 83.7 |

400 Hour Lifetime Test

In the 400 hour lifetime test, forty-eight different Ni(Nb, Ta, Ti)(Sm, Sn, Co, Cs, Sb, Ag) (Mg, Ca, Li) oxide catalysts were prepared by precipitation using the metal salt precursors substantially as described in earlier examples herein. The various catalyst compositions, post-precipitation treatment (if any) and calcination conditions are indicated in Table 26C.

Figure 2A:
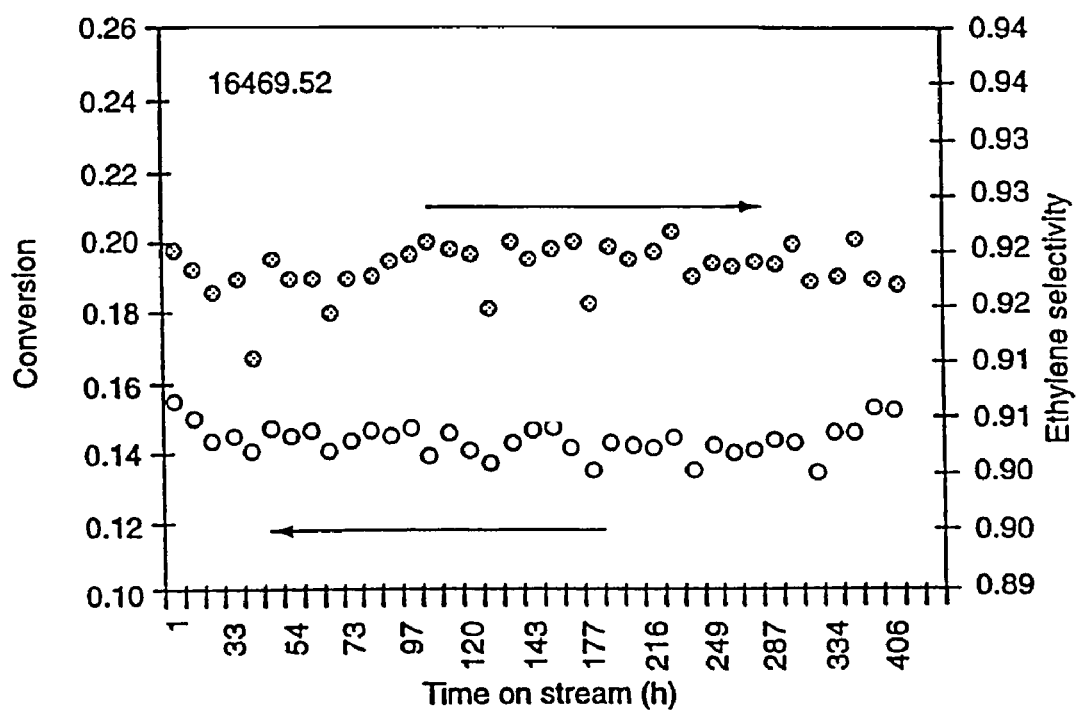
FIG. 2A and FIG. 2B are graphs showing ethane conversion (open circles) and ethylene selectivity (closed circles) data versus time on stream during the 400 hour lifetime test in the parallel fixed bed reactor at 275° C. for $Ni_{0.75}Ta_{0.28}Sn_{0.03}O_x$ (FIG. 2A) and $Ni_{0.71}Nb_{0.27}Co_{0.02}O_x$ (FIG. 2B).
Figure 2B:
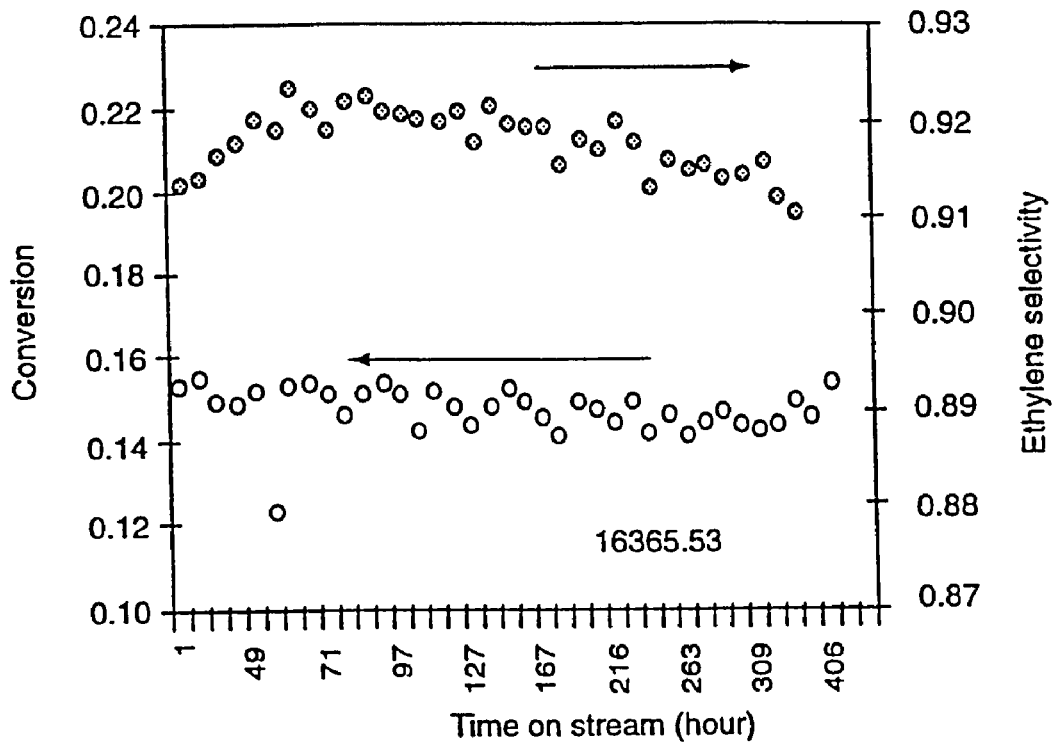

The forty-eight catalysts of Table 26C (~50 mg) were screened simultanteously in the 48-channel parallel fixed bed reactor for oxidative ethane dehydrogenation at 275° C. with ethane:oxygen flow of 0.42:0.033 sccm. Table 26D summarizes the amount of catalyst screened, as well as the ethane conversion (C) and ethylene selectivity (S) for each of the catalysts, measured after various times during the test. These data show that, after 48 hours on stream, the 48 catalysts lost, on average, less than about 13% in conversion and less than about 2% in selectivity. Several of the catalysts had no substantial loss of activity or selectivity over the 400 hour test. FIGS. 2A and 2B show ethane conversion and ethylene selectivity data versus time on stream during the 400 hour lifetime test for $Ni_{0.75}Ta_{0.28}Sn_{0.03}O_x$ (FIG. 2A) and $Ni_{0.71}Nb_{0.27}CO_{0.02}O_x$ (FIG. 2B).

TABLE 26C

Catalyst composition, library reference #, and preparation methods for catalysts screened in 400 hour lifetime test.

| | Library # | Composition | Remarks* |
|---|---|---|---|
| | | Part A | |
| (1,1) | 16693.1A | $Ni_{0.68}Nb_{0.10}Ti_{0.10}Ta_{0.10}Sm_{0.02}O_x$ | 5/320/8/air |
| (1,2) | 16693.1B | $Ni_{0.68}Nb_{0.10}Ti_{0.10}Ta_{0.10}Sm_{0.02}O_x$ | PGS, >300 μm |
| (1,3) | 16693.1C | $Ni_{0.68}Nb_{0.10}Ti_{0.10}Ta_{0.10}Sm_{0.02}O_x$ | PGS, >150 <300 μm |
| (1,4) | 16693.2 | $Ni_{0.68}Nb_{0.10}Ti_{0.10}Ta_{0.10}Sm_{0.02}O_x$ | 5/320/8/$N_2$ |
| (1,5) | 16693.3 | $Ni_{0.68}Nb_{0.10}Ti_{0.10}Ta_{0.10}Sm_{0.02}O_x$ | 5/320/8/air&5/320/8/$H_2$/Ar |
| (1,6) | 16693.4 | $Ni_{0.68}Nb_{0.10}Ti_{0.10}Ta_{0.10}Sm_{0.02}O_x$ | 5/320/8/$H_2$/Ar |
| (2,1) | 16693.5 | $Ni_{0.68}Nb_{0.10}Ti_{0.10}Ta_{0.10}Sm_{0.02}O_x$ | 5/320/8/$N_2$&5/320/8/air |
| (2,2) | 16693.6 | $Ni_{0.68}Nb_{0.10}Ti_{0.10}Ta_{0.10}Sm_{0.02}O_x$ | 5/320/8/$H_2$/Ar&5/320/8/air |
| (2,3) | 16777.31 | $Ni_{0.75}Nb_{0.25}O_x$ | 5/320/8/air |
| (2,4) | 16777.14 | $Ni_{0.66}Nb_{0.34}O_x$ | 5/320/8/air |
| (2,5) | 16777.35 | $Ni_{0.71}Nb_{0.26}Sm_{0.03}O_x$ | 5/320/8/air |
| (2,6) | 16777.53 | $Ni_{0.71}Nb_{0.26}Sm_{0.03}O_x$ | 5/320/8/air |
| (3,1) | 16467.54 | $Ni_{0.67}Nb_{0.32}Sn_{0.01}O_x$ | 5/320/8/air |
| (3,2) | 16469.52 | $Ni_{0.75}Ta_{0.28}Sn_{0.03}O_x$ | 5/320/8/air |
| (3,3) | 16469.64 | $Ni_{0.62}Ta_{0.37}Sn_{0.01}O_x$ | 5/320/8/air |
| (3,4) | 16505.53 | $Ni_{0.75}Zr_{0.23}Sn_{0.02}O_x$ | 5/320/8/air |
| (3,5) | 16470.31 | $Ni_{0.85}Ti_{0.13}Sn_{0.02}O_x$ | 5/320/8/air |
| (3,6) | 16470.53 | $Ni_{0.67}Ti_{0.31}Sn_{0.02}O_x$ | 5/320/8/air |
| (4,1) | 16470.63 | $Ni_{0.65}Ti_{0.32}Sn_{0.03}O_x$ | 5/320/8/air |
| (4,2) | 16650.14A | $Ni_{0.68}Nb_{0.10}Ti_{0.10}Ta_{0.10}Sm_{0.02}O_x$ | 5/320/8/air |
| (4,3) | 16650.14B | $Ni_{0.68}Nb_{0.10}Ti_{0.10}Ta_{0.10}Sm_{0.02}O_x$ | 5/320/8/air |
| (4,4) | 16650.42 | $Ni_{0.68}Nb_{0.10}Ti_{0.10}Ta_{0.10}Sm_{0.02}O_x$ | 5/320/8/air |
| (4,5) | 11525 | $Ni_{0.63}Nb_{0.19}Ta_{0.18}O_x$ | 5/400/8/air |
| (4,6) | 16610.3 | $Ni_{0.63}Nb_{0.19}Ta_{0.18}O_x$ | 5/320/8/$N_2$ |
| (5,1) | 16365.31 | $Ni_{0.85}Nb_{0.14}Co_{0.01}O_x$ | 5/320/8/air |
| (5,2) | 16365.42 | $Ni_{0.78}Nb_{0.20}Co_{0.02}O_x$ | 5/320/8/air |
| (5,3) | 16365.53 | $Ni_{0.71}Nb_{0.27}Co_{0.02}O_x$ | 5/320/8/air |
| (5,4) | 16298.11 | $Ni_{0.75}Nb_{0.22}Sm_{0.03}O_x$ | 5/320/8/air |

TABLE 26C-continued

Catalyst composition, library reference #, and preparation methods for catalysts screened in 400 hour lifetime test.

| | Library # | Composition | Remarks* |
|---|---|---|---|
| (5,5) | 16298.13 | $Ni_{0.74}Nb_{0.21}Sm_{0.03}Cs_{0.02}O_x$ | 5/320/8/air |
| (5,6) | 16298.41 | $Ni_{0.75}Nb_{0.21}Sm_{0.03}Sb_{0.01}O_x$ | 5/320/8/air |
| (6,1) | 16298.42 | $Ni_{0.74}Nb_{0.21}Sm_{0.03}Sb_{0.02}O_x$ | 5/320/8/air |
| (6,2) | 16298.71 | $Ni_{0.74}Nb_{0.21}Ti_{0.02}Sm_{0.03}O_x$ | 5/320/8/air |
| (6,3) | 16297.11 | $Ni_{0.67}Ti_{0.30}Sm_{0.03}O_x$ | 5/320/8/air |
| (6,4) | 16297.21 | $Ni_{0.66}Ti_{0.30}Sm_{0.03}Mg_{0.01}O_x$ | 5/320/8/air |
| | | Part B | |
| (6,5) | 16297.24 | $Ni_{0.64}Ti_{0.30}Sm_{0.03}Mg_{0.03}O_x$ | 5/320/8/air |
| (6,6) | 16297.33 | $Ni_{0.65}Ti_{0.30}Sm_{0.03}Ca_{0.02}O_x$ | 5/320/8/air |
| (7,1) | 16297.83 | $Ni_{0.62}Ti_{0.28}Ta_{0.07}Sm_{0.03}O_x$ | 5/320/8/air |
| (7,2) | 16160.14 | $Ni_{0.51}Nb_{0.14}Ti_{0.19}Ta_{0.15}O_x$ | 5/320/8/air |
| (7,3) | 16160.43 | $Ni_{0.58}Nb_{0.15}Ti_{0.11}Ta_{0.16}O_x$ | 5/320/8/air |
| (7,4) | 16790.13 | $Ni_{0.55}Ta_{0.44}Ag_{0.01}O_x$ | 5/320/8/air |
| (7,5) | 16790.23 | $Ni_{0.63}Ta_{0.36}Ag_{0.01}O_x$ | 5/320/8/air |
| (7,6) | 16790.36 | $Ni_{0.71}Ti_{0.28}Ag_{0.01}O_x$ | 5/320/8/air |
| (8,1) | 16685.32 | $Ni_{0.60}Ta_{0.38}Co_{0.02}O_x$ | 5/320/8/air |
| (8,2) | 16687.33 | $Ni_{0.66}Ti_{0.33}Co_{0.01}O_x$ | 5/320/8/air |
| (8,3) | 16687.43 | $Ni_{0.65}Ti_{0.33}Co_{0.02}O_x$ | 5/320/8/air |
| (8,4) | 16828.14 | $Ni_{0.71}Nb_{0.27}Co_{0.02}O_x$ | 5/320/8/air |
| (8,5) | 16828.34 | $Ni_{0.70}Nb_{0.27}Co_{0.02}Li_{0.01}O_x$ | 5/320/8/air |
| (8,6) | 16828.62 | $Ni_{0.77}Nb_{0.20}Co_{0.02}Mg_{0.01}O_x$ | 5/320/8/air |

*Calcination conditions = ramp rate (° C./min)/level (° C.)/dwell time (h)/environment.
*PGS = pressed, ground and sieved.

TABLE 26D

Catalyst library reference #, sample mass (mg) and ethane conversion (C) and ethylene selectivity (S) measured at various times on stream during screening in 400 hour lifetime test.

| Time on stream (hour) | | 0.9 | | 4.9 | | 167.4 | | 248.8 | | 406.2 | |
|---|---|---|---|---|---|---|---|---|---|---|---|
| Library # | Mass (mg) | C (%) | S (%) | C (%) | S (%) | C (%) | S (%) | C (%) | S (%) | C (%) | S (%) |
| | | | | | Part A | | | | | | |
| 16693.1 | 50.2 | 13.1 | 89.3 | 12.8 | 89.5 | 10.9 | 88.9 | 10.7 | 88.1 | 11.8 | 87.0 |
| 16693.1 | 51.2 | 14.0 | 90.1 | 13.9 | 90.5 | 12.2 | 90.1 | 12.1 | 89.0 | 13.1 | 88.4 |
| 16693.1 | 50.8 | 14.1 | 90.2 | 14.2 | 90.3 | 12.7 | 90.2 | 12.4 | 89.0 | 13.2 | 87.7 |
| 16693.2 | 50.9 | 4.9 | 0.2 | 13.0 | 62.6 | 12.5 | 87.7 | 12.3 | 86.3 | 9.9 | 85.9 |
| 16693.3 | 51.0 | 12.0 | 86.7 | 13.4 | 89.1 | 11.8 | 88.3 | 11.6 | 87.1 | 12.0 | 86.5 |
| 16693.4 | 50.0 | 7.8 | 64.1 | 10.9 | 84.6 | 9.4 | 86.6 | 9.2 | 85.1 | 9.7 | 83.2 |
| 16693.5 | 50.4 | 12.9 | 90.0 | 12.6 | 89.4 | 11.2 | 88.2 | 10.4 | 87.5 | 11.3 | 85.8 |
| 16693.6 | 49.8 | 11.5 | 87.9 | 9.1 | 87.3 | 9.0 | 85.2 | 8.7 | 84.3 | 9.2 | 82.9 |
| 16777.31 | 48.0 | 14.2 | 90.1 | 14.2 | 90.2 | 12.9 | 90.2 | 12.7 | 89.7 | 13.4 | 88.4 |
| 16777.14 | 53.6 | 15.0 | 90.6 | 15.0 | 90.9 | 13.0 | 89.4 | 12.6 | 88.7 | 11.8 | 88.3 |
| 16777.35 | 50.7 | 14.3 | 90.3 | 14.3 | 90.5 | 12.8 | 89.7 | 12.4 | 89.2 | 12.9 | 88.3 |
| 16777.53 | 48.0 | 14.8 | 90.5 | 14.5 | 90.6 | 12.7 | 89.8 | 12.4 | 89.0 | 13.0 | 87.4 |
| 16467.54 | 50.0 | 14.7 | 91.9 | 14.9 | 92.0 | 13.1 | 90.8 | 12.2 | 90.2 | 12.1 | 88.8 |
| 16469.52 | 52.0 | 15.5 | 92.1 | 15.0 | 91.9 | 14.1 | 92.1 | 14.1 | 91.9 | 15.1 | 91.7 |
| 16469.64 | 48.0 | 15.9 | 92.6 | 15.9 | 92.6 | 12.9 | 92.1 | 12.4 | 91.7 | 12.5 | 90.7 |
| 16505.53 | 52.6 | 12.8 | 86.5 | 12.7 | 86.3 | 11.3 | 84.4 | 9.9 | 83.8 | 9.3 | 83.3 |
| | | | | | Part B | | | | | | |
| 16470.31 | 51.0 | 13.2 | 87.8 | 12.9 | 87.4 | 11.0 | 85.3 | 10.6 | 84.8 | 11.1 | 84.3 |
| 16470.53 | 48.7 | 16.1 | 92.6 | 15.5 | 92.7 | 14.6 | 92.7 | 14.6 | 92.5 | 11.4 | 91.8 |
| 16470.63 | 51.0 | 15.4 | 92.3 | 15.6 | 92.4 | 13.5 | 92.2 | 13.8 | 91.9 | 13.8 | 90.7 |
| 16650.14 | 49.1 | 14.4 | 90.8 | 14.0 | 90.8 | 12.1 | 89.2 | 11.7 | 88.4 | 12.1 | 87.4 |
| 16650.14 | 22.5 | 11.3 | 88.9 | 11.0 | 88.5 | 8.7 | 86.5 | 8.3 | 85.6 | 8.5 | 84.0 |
| 16650.42 | 54.8 | 14.9 | 90.3 | 14.6 | 90.6 | 11.9 | 89.7 | 10.7 | 89.0 | 12.3 | 88.4 |
| 11525 | 54.3 | 5.7 | 86.8 | 5.7 | 87.1 | 5.0 | 86.3 | 4.8 | 85.5 | 4.7 | 84.9 |
| 16610.3 | 52.0 | 15.4 | 91.5 | 14.8 | 91.9 | 12.2 | 91.6 | 12.3 | 91.1 | 10.4 | 89.9 |
| 16365.31 | 50.0 | 14.9 | 91.8 | 14.8 | 91.9 | 13.4 | 92.5 | 13.8 | 92.6 | 14.4 | 91.9 |
| 16365.42 | 50.2 | 15.1 | 91.7 | 15.2 | 91.9 | 14.6 | 92.5 | 14.6 | 92.3 | 15.5 | 91.9 |
| 16365.53 | 49.8 | 15.3 | 91.4 | 15.5 | 91.5 | 14.5 | 92.0 | 14.6 | 91.6 | 15.2 | 90.4 |
| 16298.11 | 50.4 | 15.1 | 90.9 | 14.7 | 90.9 | 13.3 | 90.7 | 12.3 | 90.4 | 12.9 | 89.6 |
| 16298.13 | 50.0 | 15.3 | 91.3 | 15.2 | 91.3 | 14.2 | 91.1 | 14.2 | 91.0 | 14.5 | 90.4 |
| 16298.41 | 50.1 | 14.8 | 91.4 | 13.7 | 91.3 | 12.8 | 91.3 | 10.3 | 90.8 | 10.2 | 92.4 |
| 16298.42 | 49.8 | 15.5 | 92.3 | 15.3 | 92.4 | 13.6 | 92.9 | 14.0 | 92.5 | 14.2 | 91.6 |

TABLE 26D-continued

Catalyst library reference #, sample mass (mg) and ethane conversion (C) and ethylene selectivity (S) measured at various times on stream during screening in 400 hour lifetime test.

| Time on stream (hour) | | 0.9 | | 4.9 | | 167.4 | | 248.8 | | 406.2 | |
|---|---|---|---|---|---|---|---|---|---|---|---|
| Library # | Mass (mg) | C (%) | S (%) | C (%) | S (%) | C (%) | S (%) | C (%) | S (%) | C (%) | S (%) |
| 16298.71 | 50.4 | 14.6 | 90.8 | 14.7 | 90.9 | 13.5 | 90.3 | 12.6 | 89.6 | 13.8 | 88.3 |
| 16297.11 | 49.6 | 14.2 | 91.8 | 15.7 | 91.9 | 14.0 | 91.8 | 14.2 | 91.3 | 14.5 | 90.0 |
| 16297.21 | 49.6 | 15.7 | 91.7 | 15.4 | 91.9 | 13.8 | 91.5 | 13.1 | 91.0 | 12.8 | 90.3 |
| 16297.24 | 49.7 | 15.5 | 91.7 | 15.3 | 91.9 | 14.0 | 91.2 | 13.8 | 90.8 | 13.9 | 89.9 |
| 16297.33 | 49.9 | 15.8 | 91.4 | 15.4 | 91.4 | 13.5 | 91.4 | 12.9 | 91.0 | 12.7 | 91.5 |
| 16297.83 | 49.6 | 15.8 | 91.1 | 15.2 | 91.5 | 12.9 | 91.0 | 13.1 | 90.3 | 12.9 | 88.5 |
| 16160.14 | 49.9 | 15.0 | 92.1 | 15.0 | 92.2 | 11.6 | 90.4 | 10.4 | 89.8 | 10.9 | 88.7 |
| 16160.43 | 50.1 | 15.0 | 92.1 | 13.7 | 92.0 | 11.6 | 90.4 | 11.4 | 89.9 | 11.4 | 88.6 |
| 16790.13 | 50.0 | 14.7 | 91.6 | 14.4 | 91.7 | 11.6 | 90.3 | 11.3 | 90.0 | 11.3 | 89.6 |
| 16790.23 | 50.2 | 14.8 | 91.8 | 14.4 | 91.9 | 11.2 | 90.6 | 11.0 | 90.5 | 10.8 | 90.0 |
| 16790.36 | 50.2 | 15.2 | 90.8 | 14.8 | 91.2 | 12.5 | 90.4 | 12.6 | 91.2 | 12.2 | 90.3 |
| 16685.32 | 49.9 | 14.3 | 91.3 | 14.2 | 91.4 | 11.0 | 90.5 | 10.5 | 89.8 | 9.8 | 88.4 |
| 16687.33 | 49.5 | 13.5 | 91.0 | 15.2 | 91.2 | 13.9 | 90.5 | 12.8 | 89.9 | 13.7 | 88.3 |
| 16687.43 | 49.9 | 15.1 | 90.9 | 15.1 | 91.3 | 14.0 | 90.9 | 13.7 | 90.3 | 14.0 | 88.6 |
| 16828.14 | 50.2 | 15.1 | 90.5 | 15.0 | 90.8 | 13.8 | 90.9 | 13.5 | 90.6 | 13.9 | 89.8 |
| 16828.34 | 49.7 | 15.0 | 90.0 | 14.9 | 90.3 | 13.5 | 89.1 | 13.3 | 88.3 | 13.3 | 86.9 |
| 16828.62 | 50.6 | 14.8 | 91.2 | 14.0 | 91.4 | 13.3 | 91.7 | 12.8 | 91.9 | 13.6 | 91.7 |

Example 27

ODHE over Ni(Nb, Ta, Ti, Zr)(Ce, Dy, Er, Nd, Sm, Yb, Pr, Gd, Sb, Bi) Oxide Catalysts with Ethylene Co-Feed Catalyst compositions comprising various Ni(Nb, Ta, Ti, Zr)(Ce, Dy, Er, Nd, Sm, Yb, Pr, Gd, Sb, Bi) oxides were prepared as described in connection with Example 26 (see Table 26A), and screened in the parallel fixed bed reactor for oxidative dehydrogenation with an ethane and ethylene cofeed. Specifically, these catalysts were screened at 300° C. with an ethane (49.5%) and ethylene (50.5%) mixed feed at a ratio of ethane/ethylene mixed feed:nitrogen:oxygen was 0.42:0.54:0.088 sccm.

Table 27A shows the catalyst compositions, the sample mass thereof screened, the amount of ethane loss/ethylene gain resulting from the reaction, and the calculated ethylene selectivity of the reaction. These data demonstrate that the oxydehydrogenation activity of the catalysts are not substantially product inhibited, and that ethane dehydrogenation can be effected using feed streams having ~50% ethylene product.

TABLE 27A

Ethane loss, ethylene gain and ethylene selectivity for a mixed feed (ethane (49.5%) and ethylene (50.5%) screen in the parallel fixed bed reactors. Test condition: $(C_2H_4/C_2H_6):N_2:O_2$ flow of 0.42: 0.54: 0.088 sccm at 300° C.

| | Catalyst | Mass (mg) | Ethylene Gain (%) | Ethane loss (%) | Ethylene Selectivity (%) |
|---|---|---|---|---|---|
| | Part A | | | | |
| 1 | $Ni_{0.86}Ta_{0.14}O_x$ | 49.4 | 5.6 | −7.9 | 59.9 |
| 2 | $Ni_{0.65}Ta_{0.31}Ce_{0.04}O_x$ | 50.0 | 2.5 | −5.8 | 38.0 |
| 3 | $Ni_{0.62}Nb_{0.19}Ta_{0.19}Ce_{0.01}O_x$ | 50.4 | 0.4 | −3.3 | 11.4 |
| 4 | $Ni_{0.73}Ta_{0.24}Dy_{0.03}O_x$ | 50.5 | 0.5 | −3.8 | 10.7 |
| 5 | $Ni_{0.68}Nb_{0.25}Dy_{0.07}O_x$ | 49.8 | 2.0 | −5.0 | 35.0 |
| 6 | $Ni_{0.68}Nb_{0.26}Er_{0.06}O_x$ | 49.8 | 2.8 | −5.8 | 42.3 |

TABLE 27A-continued

Ethane loss, ethylene gain and ethylene selectivity for a mixed feed (ethane (49.5%) and ethylene (50.5%) screen in the parallel fixed bed reactors. Test condition: $(C_2H_4/C_2H_6):N_2:O_2$ flow of 0.42: 0.54: 0.088 sccm at 300° C.

| | Catalyst | Mass (mg) | Ethylene Gain (%) | Ethane loss (%) | Ethylene Selectivity (%) |
|---|---|---|---|---|---|
| 7 | Blank | 1.0 | 2.1 | −1.8 | * |
| 8 | $Ni_{0.62}Nb_{0.38}O_x$ | 49.2 | 3.2 | −6.0 | 46.0 |
| 9 | $Ni_{0.71}Ta_{0.23}Nd_{0.06}O_x$ | 49.6 | 0.8 | −4.0 | 16.9 |
| 10 | $Ni_{0.63}Nb_{0.34}Sm_{0.03}O_x$ | 50.4 | 1.0 | −4.5 | 19.9 |
| 11 | $Ni_{0.54}Ta_{0.45}Sm_{0.01}O_x$ | 49.5 | 2.0 | −4.6 | 38.0 |
| 12 | $Ni_{0.72}Ti_{0.28}O_x$ | 50.0 | 2.7 | −5.5 | 43.5 |
| 13 | $Ni_{0.66}Ti_{0.29}Yb_{0.05}O_x$ | 49.5 | 5.0 | −7.3 | 58.5 |
| 14 | blank | 1.0 | 0.8 | −0.7 | * |
| 15 | $Ni_{0.62}Nb_{0.34}Ce_{0.04}O_x$ | 42.6 | −0.7 | −2.9 | 0.0 |
| 16 | $Ni_{0.62}Ta_{0.34}Ce_{0.04}O_x$ | 47.6 | −0.9 | −2.5 | 0.0 |
| 17 | $Ni_{0.76}Nb_{0.17}Er_{0.06}O_x$ | 45.0 | 1.0 | −3.1 | 27.3 |
| 18 | $Ni_{0.68}Ta_{0.25}Dy_{0.07}O_x$ | 44.2 | 2.1 | −4.0 | 45.4 |
| 19 | $Ni_{0.60}Nb_{0.19}Ta_{0.18}Sm_{0.03}O_x$ | 45.6 | 5.3 | −6.9 | 64.7 |
| 20 | $Ni_{0.64}Nb_{0.34}Pr_{0.02}O_x$ | 48.1 | 2.7 | −5.0 | 46.8 |
| 21 | blank | 1.0 | −1.0 | 0.8 | * |
| 22 | $Ni_{0.63}Nb_{0.37}O_x$ | 45.9 | −0.2 | −1.9 | 0.0 |
| 23 | $Ni_{0.51}Ta_{0.42}Zr_{0.07}O_x$ | 44.5 | 2.5 | −4.6 | 46.4 |
| 24 | $Ni_{0.73}Ti_{0.27}O_x$ | 45.8 | 1.3 | −3.4 | 34.6 |
| 25 | $Ni_{0.58}Ta_{0.34}Gd_{0.07}O_x$ | 45.6 | 3.7 | −4.9 | 65.2 |
| 26 | $Ni_{0.68}Nb_{0.24}Gd_{0.08}O_x$ | 55.2 | 2.7 | −4.9 | 47.5 |
| 27 | $Ni_{0.80}Nb_{0.19}Sb_{0.01}O_x$ | 48.6 | 0.6 | −2.8 | 19.9 |
| | Part B | | | | |
| 28 | blank | 1.0 | −1.5 | 1.3 | * |
| 29 | $Ni_{0.82}Nb_{0.14}Sb_{0.04}O_x$ | 49.6 | 1.5 | −3.2 | 40.9 |
| 30 | $Ni_{0.60}Nb_{0.39}Sb_{0.01}O_x$ | 51.8 | 2.4 | −5.2 | 40.5 |
| 31 | $Ni_{0.72}Nb_{0.27}Bi_{0.01}O_x$ | 54.7 | 5.1 | −6.8 | 63.6 |
| 32 | $Ni_{0.73}Ta_{0.25}Bi_{0.02}O_x$ | 50.0 | 1.9 | −3.5 | 47.9 |
| 33 | $Ni_{0.63}Nb_{0.33}Yb_{0.04}O_x$ | 41.1 | 0.5 | −3.0 | 14.5 |
| 34 | $Ni_{0.59}Ta_{0.37}Yb_{0.04}O_x$ | 47.1 | −0.7 | −1.2 | 0.0 |
| 35 | blank | 1.0 | −0.4 | 0.3 | * |
| 36 | $Ni_{0.65}Nb_{0.33}Ce_{0.02}O_x$ | 48.3 | 2.6 | −5.1 | 44.1 |
| 37 | $Ni_{0.71}Nb_{0.27}Sb_{0.02}O_x$ | 49.1 | 6.0 | −8.0 | 64.1 |
| 38 | $Ni_{0.65}Nb_{0.33}Ce_{0.02}O_x$ | 49.3 | 2.7 | −4.8 | 49.3 |
| 39 | $Ni_{0.63}Nb_{0.19}Ta_{0.18}O_x/TiO_2$ | 145.9 | −1.0 | −0.8 | 0.0 |
| 40 | $Ni_{0.71}Nb_{0.27}Sb_{0.02}O_x$ | 51.5 | −0.1 | −2.0 | 0.0 |
| 41 | $Ni_{0.65}Nb_{0.33}Ce_{0.02}O_x$ | 49.7 | 2.3 | −4.9 | 41.1 |

TABLE 27A-continued

Ethane loss, ethylene gain and ethylene selectivity for a mixed feed (ethane (49.5%) and ethylene (50.5%) screen in the parallel fixed bed reactors. Test condition: $(C_2H_4/C_2H_6):N_2:O_2$ flow of 0.42: 0.54: 0.088 sccm at 300° C.

| | Catalyst | Mass (mg) | Ethylene Gain (%) | Ethane loss (%) | Ethylene Selectivity (%) |
|---|---|---|---|---|---|
| 42 | blank | 1.0 | −0.1 | 0.1 | * |
| 43 | $Ni_{0.74}Nb_{0.08}Ta_{0.17}Ce_{0.01}O_x$ | 50.0 | 5.0 | −7.2 | 59.3 |
| 44 | $Ni_{0.75}Nb_{0.24}Ce_{0.01}O_x$ | 50.2 | 3.2 | −6.1 | 46.1 |
| 45 | $Ni_{0.53}Ta_{0.40}Gd_{0.07}O_x$ | 48.9 | 0.6 | −4.2 | 13.3 |
| 46 | $Ni_{0.74}Nb_{0.08}Ta_{0.17}Ce_{0.01}O_x$ | 50.9 | 0.3 | −3.5 | 8.9 |
| 47 | $Ni_{0.74}Ta_{0.22}Yb_{0.04}O_x$ | 50.7 | 2.1 | −5.1 | 35.6 |
| 48 | $Ni_{0.65}Ta_{0.36}Bi_{0.01}O_x$ | 50.4 | 2.3 | −4.9 | 41.1 |

Example 28

Figure 1B:
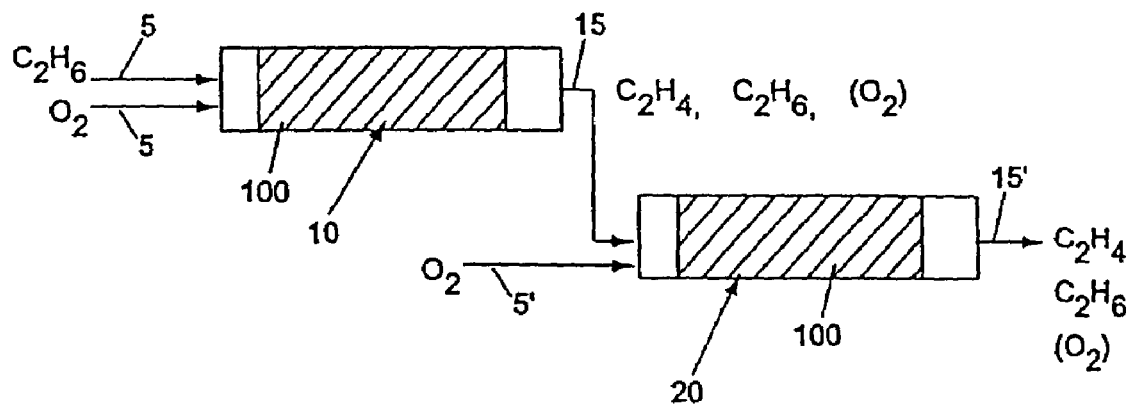

ODHE over NiNbTa Oxide Catalyst with Multi-Stage Fixed Bed Reactor and Multiple Oxygen Feed A NiNbTa oxide catalyst, $Ni_{0.63}Nb_{0.19}Ta_{0.18}O_x$, prepared from nickel nitrate, niobium oxalate and tantalum oxalate by precipitation with tetramethylammonium hydroxide and with a maximum calcination temperature of 320° C. was screened in a three-stage fixed bed reactor having multiple oxygen feeds, substantially as shown and described in connection with FIG. 1B.

Briefly, about 50 mg of the catalyst was loaded into each of the reactor stages. Ethane, oxygen and nitrogen were fed as initial feed to the first stage of the multi-stage reactor, wherein ethane was oxidatively dehydrogenated to form ethylene. The exhaust from the first stage was fed to the second stage, together with additional oxygen and nitrogen feed, and further oxidative dehydrogenation of ethane was effected in the second stage. Similarly, exhaust from the second stage was fed to the third stage, together with additional oxygen and nitrogen feed, and further oxidative dehydrogenation of ethane was effected in the third stage. The reaction exhaust from the third stage was analyzed by gas chromatograph.

Nine different experimental cases were considered with variations in (1) the relative flowrates of nitrogen:oxygen: ethane in the initial (first-stage) feed, (2) the relative flowrates of nitrogen:oxygen used as additional feed in the second and third stages, and/or (3) the reaction temperatures of the three reaction zones (300° C. or 275° C.).

For comparison, the NiNbTa oxide catalyst was also screened, in each of the nine experimental cases, under similar reaction conditions in a single-stage, single-feed fixed bed reactor, substantially as shown and described in connection with FIG. 1A.

Table 28A shows the reaction temperature, amount of catalyst, initial feed rates (sccm of nitrogen:oxygen:ethane), additional feed rates (sccm of nitrogen:ethane), and performance data (conversion, selectivity) for each of the nine different experimental cases shows—for the multi-stage reactor and the single-stage reactor configurations. These data demonstrate that overall ethane conversion can be substantially improved (e.g., C of not less than about 30% C, and ranging from about 30% to about 45%) while maintaining relatively high ethylene selectivities (e.g., S of not less than about 70% S, and ranging from about 70% to about 85%).

TABLE 28A

Ethane conversion and ethylene selectivity for $Ni_{0.63}Nb_{0.19}Ta_{0.18}O_x$ in multi-stage and single-stage reactor configurations at various flowrates and temperatures.

| | Reactor Configuration | Reaction T (C) | mass (mg) | Initial feed N2:O2:C2H6 (sccm) | addition feed N2:O2 (sccm) | C (%) | S (%) |
|---|---|---|---|---|---|---|---|
| | | | | Part A | | | |
| | SF | 300 C | 52.9 | 0.32: 0.088: 0.42 | n/a | 18.2 | 85.4 |
| Case I | MF1 | 300 C | 51.6 | 0.32: 0.088: 0.42 | | | |
| | MF2 | 300 C | 49.0 | | 0.32: 0.088 | | |
| | MF3 | 300 C | 51.4 | | 0.32: 0.088 | 33.6 | 74.5 |
| | SF | 300 C | 52.9 | 0.25: 0.066: 0.42 | n/a | 17.4 | 87.7 |
| Case II | MF1 | 300 C | 51.6 | 0.25: 0.066: 0.42 | | | |
| | MF2 | 300 C | 49.0 | | 0.25: 0.066 | | |
| | MF3 | 300 C | 51.4 | | 0.25: 0.066 | 32.0 | 76.9 |
| | SF | 300 C | 52.9 | 0.16: 0.044: 0.42 | n/a | 16.5 | 90.8 |
| | | | | Part B | | | |
| Case III | MF1 | 300 C | 51.6 | 0.16: 0.044: 0.42 | | | |
| | MF2 | 300 C | 49.0 | | 0.16: 0.044 | | |
| | MF3 | 300 C | 51.4 | | 0.16: 0.044 | 31.1 | 81.3 |
| | SF | 300 C | 52.9 | 0.082: 0.022: 0.42 | n/a | 11.4 | 93.6 |
| Case IV | MF1 | 300 C | 51.6 | 0.082: 0.022: 0.42 | | | |
| | MF2 | 300 C | 49.0 | | 0.082: 0.022 | | |
| | MF3 | 300 C | 51.4 | | 0.082: 0.022 | 26.1 | 85.8 |
| | SF | 300 C | 52.9 | 0.16: 0.044: 0.208 | n/a | 22.0 | 85.9 |
| Case V | MF1 | 300 C | 51.6 | 0.16: 0.044: 0.208 | | | |
| | MF2 | 300 C | 49.0 | | 0.16: 0.044 | | |
| | MF3 | 300 C | 51.4 | | 0.16: 0.044 | 44.6 | 73.9 |

TABLE 28A-continued

Ethane conversion and ethylene selectivity for $Ni_{0.63}Nb_{0.19}Ta_{0.18}O_x$ in multi-stage and single-stage reactor configurations at various flowrates and temperatures.

|  | Reactor Configuration | Reaction T (C) | mass (mg) | Initial feed N2:O2:C2H6 (sccm) | addition feed N2:O2 (sccm) | C (%) | S (%) |
|---|---|---|---|---|---|---|---|
|  | SF | 300 C | 52.9 | 0.082: 0.022: 0.208 | n/a | 18.2 | 91.2 |
| Case VI | MF1 | 300 C | 51.6 | 0.082: 0.022: 0.208 |  |  |  |
|  | MF2 | 300 C | 49.0 |  | 0.082: 0.022 |  |  |
|  | MF3 | 300 C | 51.4 |  | 0.082: 0.022 | 39.3 | 78.4 |
|  | SF | 300 C | 52.9 | 0.041: 0.011: 0.208 | n/a | 12.1 | 89.9 |
| Case VII | MF1 | 300 C | 51.6 | 0.041: 0.011: 0.208 |  |  |  |
|  | MF2 | 300 C | 49.0 |  | 0.041: 0.011 |  |  |
|  | MF3 | 300 C | 51.4 |  | 0.041: 0.011 | 29.0 | 84.8 |
|  | SF | 275 C | 52.9 | 0.206: 0.055: 1.04 | n/a | 7.6 | 93.1 |
| Case VIII | MF1 | 275 C | 51.6 | 0.206: 0.055: 1.04 |  |  |  |
|  | MF2 | 275 C | 49.0 |  | 0.206: 0.055 |  |  |
|  | MF3 | 275 C | 51.4 |  | 0.206: 0.055 | 15.8 | 86.7 |
|  | SF | 275 C | 52.9 | 0.082: 0.022: 0.42 | n/a | 10.7 | 93.7 |
| Case IX | MF1 | 275 C | 51.6 | 0.082: 0.022: 0.42 |  |  |  |
|  | MF2 | 275 C | 49.0 |  | 0.079: 0.021 |  |  |
|  | MF3 | 275 C | 51.4 |  | 0.079: 0.021 | 23.2 | 86.0 |

SF = single feed; MF1 = multi-feed, $1^{st}$ stage; MF2 = multifeed, $2^{nd}$ stage; MF3 = multifeed, $3^{rd}$ stage; C = ethane conversion; S = ethylene selectivity.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

I claim

1. A method for preparing acetic acid from substituted or unsubstituted ethane, the method comprising:

providing substituted or unsubstituted ethane and a gaseous oxidant to a reaction zone containing a catalyst and a co-catalyst, the catalyst consisting essentially of Ni, a Ni oxide, a Ni salt, or mixtures thereof and one or more components chosen from the group consisting of Ti, Ta, Nb, Co, Hf, W, Zn, Zr, Al, oxides thereof and salts thereof, or mixtures thereof, and the co-catalyst having activity to oxidize ethylene to acetic acid, and dehydrogenating the substituted or unsubstituted ethane to form substituted or unsubstituted ethylene; and oxidizing the unsubstituted or substituted ethylene to form substituted or unsubstituted acetic acid wherein the catalyst and co-catalyst are in separated phases.

2. The method according to claim 1, further comprising providing an integrated catalyst composition comprising the catalyst and co-catalyst to the reaction zone.

* * * * *